US012806231B2

(12) United States Patent
Toda et al.

(10) Patent No.: US 12,806,231 B2
(45) Date of Patent: Nov. 24, 2026

(54) THERAPEUTIC AGENT USING GENOME-EDITED PLURIPOTENT STEM CELL

(71) Applicant: KEIO UNIVERSITY, Tokyo (JP)

(72) Inventors: Masahiro Toda, Tokyo (JP); Hideyuki Okano, Tokyo (JP); Ryota Tamura, Tokyo (JP); Mizuto Sato, Tokyo (JP); Masahiro Yo, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 907 days.

(21) Appl. No.: 17/915,844

(22) PCT Filed: Mar. 31, 2021

(86) PCT No.: PCT/JP2021/013834
§ 371 (c)(1),
(2) Date: Sep. 29, 2022

(87) PCT Pub. No.: WO2021/201100
PCT Pub. Date: Oct. 7, 2021

(65) Prior Publication Data

US 2024/0226175 A1 Jul. 11, 2024

(30) Foreign Application Priority Data

Mar. 31, 2020 (JP) ................................ 2020-063477
Sep. 30, 2020 (JP) ................................ 2020-165847
Dec. 28, 2020 (JP) ................................ 2020-219455

(51) Int. Cl.
*A61K 35/30* (2015.01)
*A61P 35/00* (2006.01)
*C12N 5/0797* (2010.01)
*C12Q 1/6886* (2018.01)

(52) U.S. Cl.
CPC .............. *A61K 35/30* (2013.01); *A61P 35/00* (2018.01); *C12N 5/0623* (2013.01); *C12Q 1/6886* (2013.01); *C12N 2506/45* (2013.01); *C12N 2510/00* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

2002/0039990 A1 4/2002 Stanton, Jr.
2006/0068496 A1 3/2006 Kelly
2012/0083454 A1* 4/2012 Vescovi ............... A61K 38/177 514/19.3
2019/0030083 A1 1/2019 Anversa
2021/0369785 A1 12/2021 Toda et al.

FOREIGN PATENT DOCUMENTS

EP 3 622 961 A1 3/2020
JP 2002-520072 A 7/2002
JP 2008-507981 A 3/2008
JP 2019-508502 A 3/2019
WO WO 2007/141974 A1 12/2007
WO WO-2019098361 A1 * 5/2019 ........... A61K 31/513

OTHER PUBLICATIONS

Lee JY, Lee DH, Kim HA, Choi SA, Lee HJ, Park CK, Phi JH, Wang KC, Kim SU, Kim SK. Double suicide gene therapy using human neural stem cells against glioblastoma: double safety measures. J Neurooncol. Jan. 2014; 116(1):49-57. doi: 10.1007/s11060-013-1264-6. Epub Oct. 11, 2013. PMID: 24113876. (Year: 2013).*
Zhang L, Hua Q, Tang K, Shi C, Xie X, Zhang R. CXCR4 activation promotes differentiation of human embryonic stem cells to neural stem cells. Neuroscience. Nov. 19, 2016;337:88-97. doi: 10.1016/j.neuroscience.2016.09.001. Epub Sep. 9, 2016. PMID: 27615032. (Year: 2016).*
Martin RM, Fowler JL, Cromer MK, Lesch BJ, Ponce E, Uchida N, Nishimura T, Porteus MH, Loh KM. Improving the safety of human pluripotent stem cell therapies using genome-edited orthogonal safeguards. Nat Commun. Jun. 1, 2020;11(1):2713. doi: 10.1038/s41467-020-16455-7. PMID: 32483127; PMCID: PMC7264334. (Year: 2020).*
International Search Report for PCT/JP2021/013834 (PCT/ISA/210) mailed on May 25, 2021.
Morisaka et al., "CRISPR-Cas3 induces broad and unidirectional genome editing in human cells", Nature Communications, 2019, vol. 10, No. 5302, pp. 1-13.
Nizzardo et al., "iPSC-derived LewisX+CXCR4+β1-integrin+ neural stem cells improve the amyotrophic lateral sclerosis phenotype by preserving motor neurons and muscle innervation in human and rodent models", Human Molecular Genetics, 2016, vol. 25, No. 15, pp. 3152-3163.
Nomura et al., "EphB Signaling Controls lineage Plasticity of Adult Neural Stem Cell Niche Cells", Cell Stem Cell, Dec. 3, 2010, vol. 7, pp. 730-743.
Nomura et al., "EphB/ephrin-B signaling controls continuous proliferation of the adult spinal cord neural stem cells", Neuroscience Research, 2011, vol. 71, Suppl., p. e51.
Van Der Meulen et al., "The role of CXC chemokine ligand (CXCL)12-CXC chemokine receptor (CXCR)4 signalling in the migration of neural stem cells towards a brain tumour", Neuropathology and Applied Neurobiology, 2009, vol. 35, pp. 579-591.
Written Opinion of the International Searching Authority for PCT/JP2021/013834 (PCT/ISA/237) mailed on May 25, 2021.

(Continued)

*Primary Examiner* — Christopher M Babic
*Assistant Examiner* — Alyssa G Weston
(74) *Attorney, Agent, or Firm* — Birch, Stewart, Kolasch & Birch, LLP

(57) ABSTRACT

To treat brain dysfunctions, brain diseases or tumors, the present invention provides a cell preparation comprising neural stem cells differentiated from pluripotent stem cells into which a suicide gene has been introduced.

11 Claims, 67 Drawing Sheets

Specification includes a Sequence Listing.

(56) References Cited

OTHER PUBLICATIONS

Araki et al., "Site-directed integration of the cre gene mediated by Cre recombinase using a combination of mutant lox sites," Nucleic Acids Research, vol. 30, No. 19, e103, 2002, pp. 1-8.

International Preliminary Report on Patentability dated Sep. 29, 2022, and English translation of the Written Opinion of the International Searching Authority for International Application No. PCT/JP2021/013834, dated May 25, 2021.

Extended European Search Report for European Application No. 21778965.0, dated May 10, 2024.

* cited by examiner

Day 14

Control yCD-NSCs transplanted

| Ligand | Receptor |
|---|---|
| CXCL12 | CXCR4 |
| CXCL12 | ACKR4 |
| TGFA | ERBB4 |
| SHBG | SLC37A1 |
| NTS | NGFR |
| MMP9 | EPHB2 |
| MFNG | NOTCH1 |
| COL1A1 | FLT4 |

Positions of primers for hiPS-yCD-Puro-Venus

Positions of primers for hiPS-yCD (removed by Cre protein)

Figure 16F

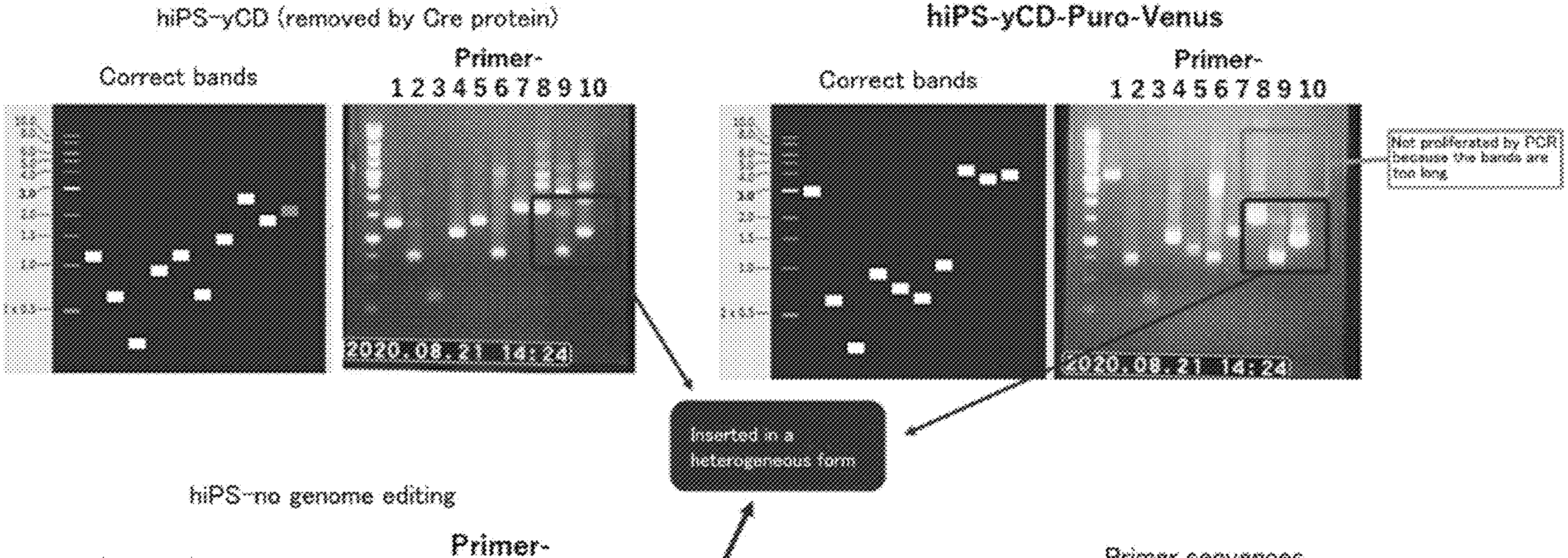

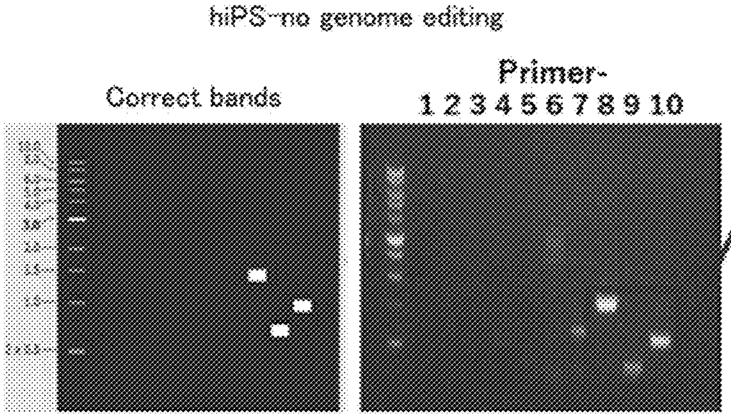

Primer sequences

| | | | |
|---|---|---|---|
| SEQ ID NO. 5 | GACGTGGAGGAAAATCCCG | SEQ ID NO. 6 | GGGTCGGATCCATAACTTCG |
| SEQ ID NO. 7 | CCCTGGAGAAGAGCTACGAG | SEQ ID NO. 8 | CGGGATTTTCCTCCACGTCA |
| SEQ ID NO. 9 | AAGTCTTCTAACATGCGGTGAC | SEQ ID NO. 10 | GGTGTACAGAGTGGTGTCCT |
| SEQ ID NO. 11 | CAGCCATGTACGTTGCTATC | SEQ ID NO. 12 | ATTTTCCTCCACGTCACCGC |
| SEQ ID NO. 13 | AGGAAGTCTTCTAACATGCGGT | SEQ ID NO. 14 | GGTCGGATCCATAACTTCGT |
| SEQ ID NO. 15 | TTCTAACATGCGGTGACGTGG | SEQ ID NO. 16 | GTCAGTCTCCACAATCTGCTT |
| SEQ ID NO. 17 | GCAGAGGAAGTCTTCTAACATGC | SEQ ID NO. 18 | AAGGGACTTCCTGTAACAACG |
| SEQ ID NO. 19 | CTGGCATCGTGATGGACTC | SEQ ID NO. 20 | ACACTTGGCCTCATTTTTAAGGT |
| SEQ ID NO. 21 | AAGTACTCCGTGTGGATCGG | SEQ ID NO. 22 | GTCACACTTGGCCTCATTTTTAAG |
| SEQ ID NO. 23 | TCCATCATGAAGTGTGACGTG | SEQ ID NO. 24 | TCACACCTTGGCCTCATTTTTAAGG |

Figure 25A

Positions and sequences of primers

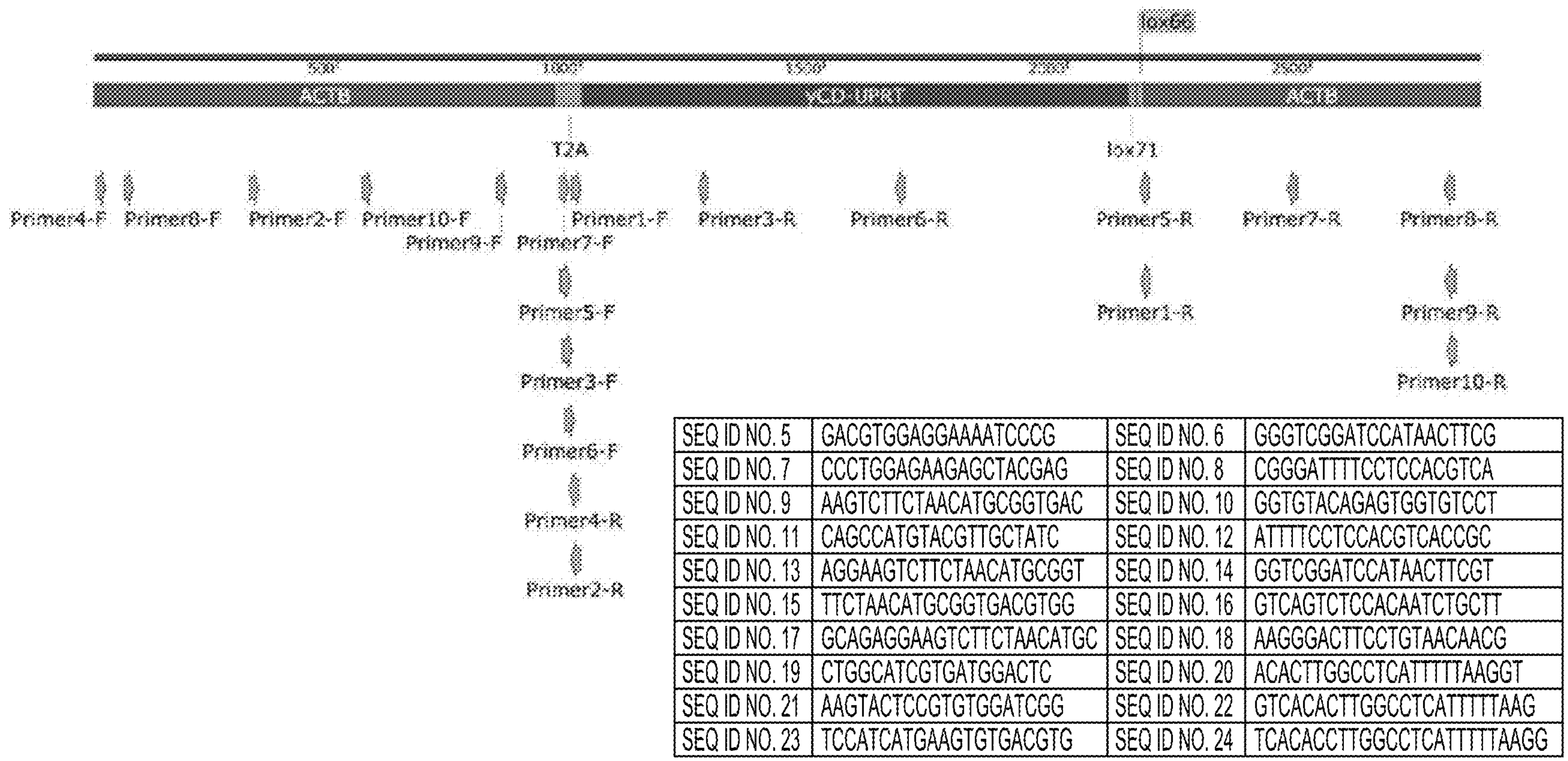

| | | | |
|---|---|---|---|
| SEQ ID NO. 5 | GACGTGGAGGAAAATCCCG | SEQ ID NO. 6 | GGGTCGGATCCATAACTTCG |
| SEQ ID NO. 7 | CCCTGGAGAAGAGCTACGAG | SEQ ID NO. 8 | CGGGATTTTCCTCCACGTCA |
| SEQ ID NO. 9 | AAGTCTTCTAACATGCGGTGAC | SEQ ID NO. 10 | GGTGTACAGAGTGGTGTCCT |
| SEQ ID NO. 11 | CAGCCATGTACGTTGCTATC | SEQ ID NO. 12 | ATTTTCCTCCACGTCACCGC |
| SEQ ID NO. 13 | AGGAAGTCTTCTAACATGCGGT | SEQ ID NO. 14 | GGTCGGATCCATAACTTCGT |
| SEQ ID NO. 15 | TTCTAACATGCGGTGACGTGG | SEQ ID NO. 16 | GTCAGTCTCCACAATCTGCTT |
| SEQ ID NO. 17 | GCAGAGGAAGTCTTCTAACATGC | SEQ ID NO. 18 | AAGGGACTTCCTGTAACAACG |
| SEQ ID NO. 19 | CTGGCATCGTGATGGACTC | SEQ ID NO. 20 | ACACTTGGCCTCATTTTTAAGGT |
| SEQ ID NO. 21 | AAGTACTCCGTGTGGATCGG | SEQ ID NO. 22 | GTCACACTTGGCCTCATTTTTAAG |
| SEQ ID NO. 23 | TCCATCATGAAGTGTGACGTG | SEQ ID NO. 24 | TCACACCTTGGCCTCATTTTTAAGG |

Positions and sequences of primers

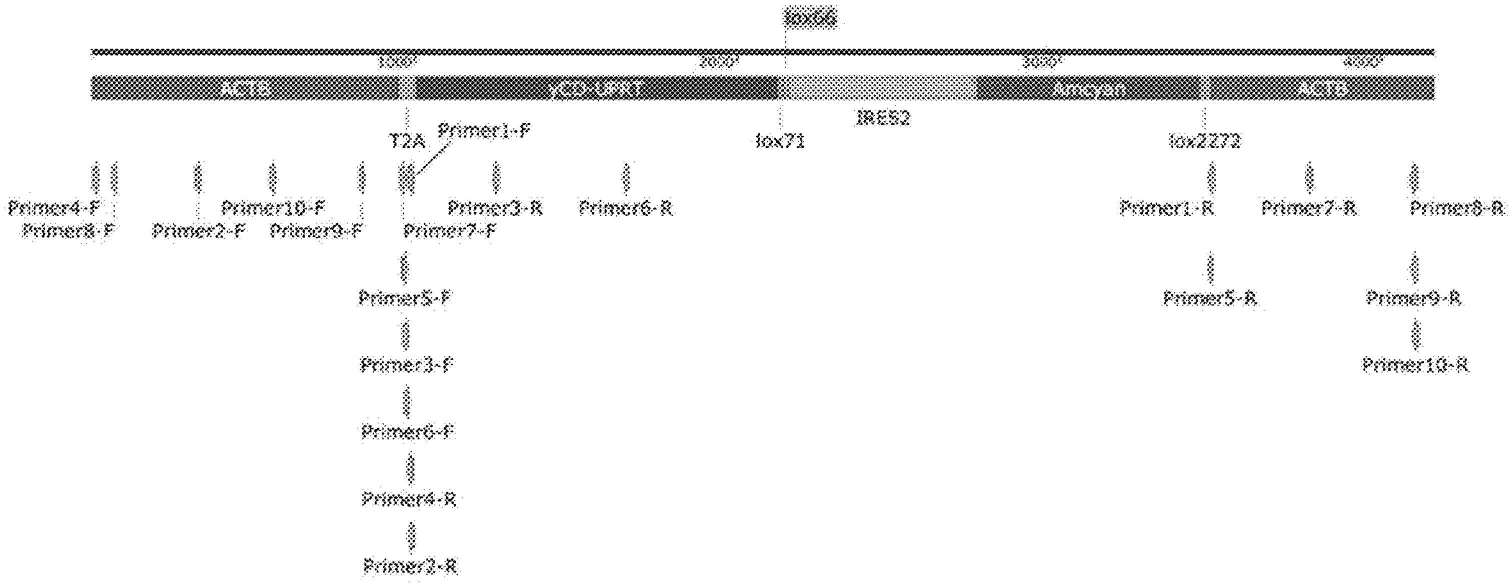

| | | | | | |
|---|---|---|---|---|---|
| SEQ ID NO. 5 | Primer1-F | GACGTGGAGGAAAATCCCG | SEQ ID NO.6 | Primer1-R | GGGTCGGATCCATAACTTCG |
| SEQ ID NO.7 | Primer2-F | CCCTGGAGAAGAGCTACGAG | SEQ ID NO.8 | Primer2-R | CGGGATTTTCCTCCACGTCA |
| SEQ ID NO.9 | Primer3-F | AAGTCTTCTAACATGCGGTGAC | SEQ ID NO.10 | Primer3-R | GGTGTACAGAGTGGTGTCCT |
| SEQ ID NO.11 | Primer4-F | CAGCCATGTACGTTGCTATC | SEQ ID NO.12 | Primer4-R | ATTTTCCTCCACGTCACCGC |
| SEQ ID NO.13 | Primer5-F | AGGAAGTCTTCTAACATGCGGT | SEQ ID NO.14 | Primer5-R | GGTCGGATCCATAACTTCGT |
| SEQ ID NO.15 | Primer6-F | TTCTAACATGCGGTGACGTGG | SEQ ID NO.16 | Primer6-R | GTCAGTCTCCACAATCTGCTT |
| SEQ ID NO.17 | Primer7-F | GCAGAGGAAGTCTTCTAACATGC | SEQ ID NO.18 | Primer7-R | AAGGGACTTCCTGTAACAACG |
| SEQ ID NO.19 | Primer8-F | CTGGCATCGTGATGGACTC | SEQ ID NO.20 | Primer8-R | ACACTTGGCCTCATTTTTAAGGT |
| SEQ ID NO.21 | Primer9-F | AAGTACTCCGTGTGGATCGG | SEQ ID NO.22 | Primer9-R | GTCACACTTGGCCTCATTTTTAAG |
| SEQ ID NO.23 | Primer10-F | TCCATCATGAAGTGTGACGTG | SEQ ID NO.24 | Primer10-R | TCACACTTGGCCTCATTTTTAAGG |

Fig. 27A

Results of genomic PCR

Figure 33A

Subcutaneous transplantation of NS/PCs into the back

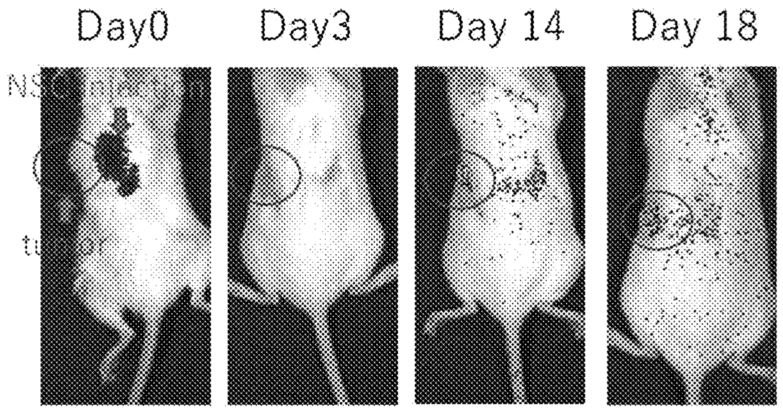

Clearly strong accumulation is observed at the site of tumor.

* Day 0 is defined as the day of transplantation of NS/PCs.

Figure 33B

Administration to the caudal vein

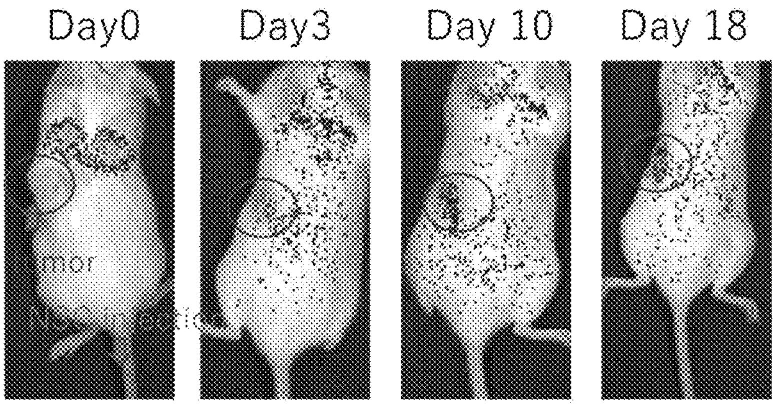

Clearly strong accumulation is gradually observed at the site of tumor after cells were initially trapped in the lungs.

* Day 0 is defined as the day of transplantation of NS/PCs.

THERAPEUTIC AGENT USING GENOME-EDITED PLURIPOTENT STEM CELL

CROSS-REFERENCE TO RELATED APPLICATIONS

This application is the National Phase of PCT International Application No. PCT/JP2021/013834 filed Mar. 31, 2021, which claims priority under 35 U.S.C. § 119(a) to Patent Application Nos. 2020-063477, 2020-165847, and 2020-219455, filed in Japan on Mar. 31, 2020; Sep. 30, 2020, and Dec. 28, 2020, respectively, all of which are hereby expressly incorporated by reference into the present application.

REFERENCE TO SEQUENCE LISTING SUBMITTED VIA EFS-WEB

The application contains a Sequence Listing which has been submitted electronically in .txt format and is hereby incorporated by reference in its entirety. Said .txt copy, created on Jul. 13, 2026, is named "2026-07-13 3749-0187PUS1_ST25.txt" and is 9,545 bytes in size. The sequence listing contained in this .txt file is part of the specification and is hereby incorporated by reference herein in its entirety.

TECHNICAL FIELD

The present invention relates to a cell preparation for treating central nervous system diseases/damages and a cell preparation for treating tumors. These cell preparations are used for the treatment of central nervous system diseases/damages, such as, for example, brain dysfunctions, traumatic brain damages, spinal cord damages, and neurodegenerative diseases, as well as brain tumors and other tumors. When a cell preparation is used as a therapeutic cell preparation, in particular, when it is used for the treatment of central nervous system diseases/damages, tumorigenesis of cells becomes of concern. However, the cell preparation of the present invention is a highly safe cell preparation because cells can be killed by a suicide gene.

BACKGROUND ART

Because cerebral contusion, which is a traumatic brain damage, is caused primarily by fall or traffic injury, the frequency of cerebral contusion still remains high among broad populations from younger people to elderly people. Brain parenchymal cells, such as nerve cells and various glial cells, are necrotized by physical injury, leading to destruction and damage of the neural network, and serious neurological symptoms occur, resulting in a fatal outcome in the worst case. Treatment of cerebral contusion is performed for contusion edema, which develops within 48 hours, especially during the first 24 hours, after injury (i.e., early massive edema), but early massive edema is resistant to conservative treatment such as use of a hyperosmotic diuretic. If disturbance of consciousness progresses after conservative treatment is performed, necrotic tissues caused by contusion are removed by craniotomy. Although a surgery can be expected to improve vital prognosis, functional prognosis still remains poor (Vella M A. Surg Clin North Am. 2017).

Cerebrovascular disorder (cerebral infarction, cerebral hemorrhage, or subarachnoid hemorrhage) is a disease which can be referred to as a Japan's national disease and used to be the leading cause of death in Japan. In cerebral infarction, brain parenchymal cells, such as nerve cells and various glial cells, are necrotized by impaired blood flow. The neural network is destroyed or damaged, and severe neurological symptoms occur, leading to a fatal outcome in the worst case (Lindvall O. Stroke. 2011). Advancement of preventive medicine, including new therapies such as administration of tissue plasminogen activator (tPA) during the hyperacute phase of cerebral infarction and management of risk factors, and improvement of public health have reduced the number of deaths due to cerebrovascular disorder, which has become the third most common cause of death. However, it still remains a disease with high mortality.

Neurodegenerative diseases are higher brain dysfunction diseases in which nerve cells are degenerated and lost by various causes. Many studies have been conducted to find methods for preventing and treating the diseases, but no therapeutic drug is available to restore the degenerated and lost cerebral nervous system.

All current therapies for impaired nervous functions are prophylactic treatment or prevention of exacerbation. Although functional recovery can be achieved to some extent by rehabilitation from dysfunction or the like, it is difficult to repair damages of the neural network, which characterizes the central nerve, and achieve complete functional recovery by existing therapies. Therefore, there is an unmet need for treatment methods that can achieve complete repair of the neural network, aiming at functional recovery, in particular, recovery from higher brain dysfunction. Stem cells are thought to be very useful because of the role played by them in reconstruction of the damaged neural network. The methods using stem cells include (1) activation of endogenous neural stem cells existing in the lateral subventricular zone in the brain and infragranular layers of the hippocampus and (2) transplantation of stem cells. However, the viability of new neurons in (1) is very low, and the neural network cannot be reconstructed with this method alone. Therefore, (2) is required as means to reconstruct the damaged neural network.

In stem cell transplantation, what donor cell is used for transplantation is important. Various cells have been proposed so far as candidate donor cells for transplantation. To date, effects of improving functions using neural stem cells (NSCs) derived from ES cells and mesenchymal stem cells (MSCs) have been reported in animal models of cerebral contusion (Non Patent Literatures 1 to 6), and bone marrow-derived MSCs (SB623) were transplanted into patients with chronic cerebral contusion in 2014 (Non Patent Literature 7). MSCs have been used in the majority of studies, including currently ongoing clinical studies (NCT02210624). However, the effect of MSCs is not aiming at reconstruction of the network in a strict sense, and the therapies are based on the theory that transplanted cells secret humoral factors which have neurotrophic/neuroprotective effects and proangiogenic. effects, thus promoting regeneration indirectly.

It has been reported that neuroepithelial stem cells are excellent as donor cells for transplantation because of the high neuronal differentiation ability thereof (Non Patent Literature 8). When neural stem cells are used as donor cells, there have been ethical and practical problems. However, neural stem cells derived from human iPS cells are ideal donor cells to solve those problems. Since iPS cells also have concerns about tumorigenicity, as seen in other cell transplantation therapies, preparation methods not using c-Myc, one of the causes of tumorigenicity, or the like are being studied. However, the tumorigenicity cannot be completely ruled out, and it has been reported that, in order to prevent tumorigenesis, the proliferating ability of stem cells themselves is reduced, and pluripotency is lost (Nakagawa M. Nat Biotechnol 2008; Stadtfeld M. Science. 2008).

Chemical compounds with various mechanisms against various target molecules have been developed as therapeutic drugs for tumors. However, there are always problems of adverse drug reactions as nature of chemical substances, and development of safe therapeutic drugs for tumors remains an urgent issue.

CITATION LIST

Non Patent Literature

[Non Patent Literature 1]
Riess P. J Neurotrauma. 2007
[Non Patent Literature 2]
Tajiri N. Front Syst. Neurosci. 2014
[Non Patent Literature 3]
Tian C. Exp Clin Transplant. 2013
[Non Patent Literature 4]
Qi L. J Craniofac Surg. 2018
[Non Patent Literature 5]
Zanier E R. Crit Care Med. 2011
[Non Patent Literature 6]
Turtzo L C. PLoS One. 2015
[Non Patent Literature 7]
Steinberg G K. Stroke. 2016
[Non Patent Literature 8]
Uchida K. Neurosci Res. 2005

SUMMARY OF INVENTION

Technical Problem

In consideration of clinical application, neural stem cells derived from human iPS cells, which can solve ethical and practical problems, are ideal as donor cells. As described above, however, iPS cells have a problem of tumorigenicity as seen in other cell transplantation therapies. The first object of the present invention is to provide neural stem cells derived from human iPS cells which have solved such a problem of tumorigenicity.

Furthermore, the present inventors successfully prepared a cell preparation for treating brain tumors by introducing a suicide gene (a gene coding for an enzyme that converts a prodrug to a substance having cytotoxicity) into a human iPS cell, and then inducing differentiation of the cell into a neural stem cell (WO 2018/207808 and WO 2019/098361). The second object of the present invention is to provide means for expressing such a suicide gene introduced into a human iPS cell constitutively in a stable manner.

Furthermore, if the therapeutic effect of the above-described cell preparation can be predicted beforehand, unnecessary treatment can be prevented, and efficient treatment can be given. The third object of the present invention is to provide means for predicting the therapeutic effect of the above-described cell preparation.

Furthermore, neural stem cells have a migratory property and an anisotropic property for tumors, but molecules involved in the properties have not been elucidated. If these molecules are elucidated, neural stem cells with enhanced migratory property and anisotropic property for tumors can be prepared, and neural stem cells with high migratory property and anisotropic property can be selected efficiently. The fourth object of the present invention is to identify molecules that impart such a migratory property or an anisotropic property to neural stem cells and to provide means for preparing neural stem cells with enhanced migratory property and anisotropic property and means for efficiently selecting neural stem cells with high migratory property and anisotropic property.

Furthermore, neural stem cells used in a cell preparation are required to be highly safe. However, genome editing techniques used to introduce a suicide gene, such as CRISPR/Cas9, have a problem of off-target effect, with which a mutation is introduced into an unintended site. Additionally, when neural stem cells harboring a suicide gene are prepared, a selection marker gene, such as a drug resistance gene, is inserted together with the suicide gene to select cells, but it is desirable to remove such a foreign gene in view of safety. The fifth object of the present invention is to provide means for preparing highly safe neural stem cells.

Solution to Problem

The present inventors have earnestly examined repeatedly to solve the above-described problems and consequently found the followings.

1) It has been found that, when neural stem cells derived from iPS cells are used as donor cells for transplantation, the above-described problem of tumorigenicity can be solved by introducing a suicide gene into iPS cells beforehand, so that cells which have been transplanted and transformed to form tumors can be killed by administering a prodrug. Furthermore, it has been found that, when a prodrug is administered at a specific time after transplantation of neural stem cells, the therapeutic effect of transplanted cells is sustained while undifferentiated cells with a risk of tumorigenesis are killed.
2) It has been found that the susceptibility of a suicide gene to a prodrug is increased by inserting the suicide gene immediately 3' to a translation region of R-actin gene in an iPS cell.
3) It has been found that the antitumor effect of therapeutic stem cells into which a suicide gene targeting a tumor cell has been introduced can be estimated by measuring the expression levels of thymidylate synthase gene and dihydropyrimidine dehydrogenase gene in the tumor cell.
4) It has been found that a ligand-receptor pair of ephrin B and ephrin B receptor (EphB) and a ligand-receptor pair of CXC motif chemokine 12 (CXCL12) and CXC motif chemokine receptor 4 (CXCR4) are associated with the migratory property and anisotropic property for tumors of neural stem cells.
5) It has been found that highly safe neural stem cells can be prepared by a genome editing technique using CRISPR/Cas3, which causes off-target effect infrequently, instead of CRISPR/Cas9, and removing an inserted selection marker gene using the Cre/loxP system. It has also been found that thus prepared neural stem cells have therapeutic effects comparable to those of neural stem cells prepared by conventional methods. Furthermore, it has been found that the safety of neural stem cells can be increased by replacing the loxP sequence in the Cre/loxP system with a loxP sequence having a mutation. It has also been found that not only a selection marker gene can be removed, but also a second gene can be inserted into the genome of a pluripotent stem cell by using the Cre/loxP system comprising this loxP sequence having a mutation and a homologous recombination vector in combination.

6) It has been found that neural stem cells differentiated from pluripotent stem cells exhibit strong anisotropic property and migratory property for tumors including brain tumors and damaged brain.

The present invention has been completed based on the above knowledge.

That is, the present invention provides the following [1] to [38].

[1]A cell preparation for treating central nervous system diseases/damages, which comprises neural stem cells differentiated from pluripotent stem cells into which a suicide gene has been introduced.

[2] The cell preparation for treating central nervous system diseases/damages according to [1], for use in treatment of brain dysfunctions.

[3] The cell preparation for treating central nervous system diseases/damages according to [1], for use in treatment of traumatic brain damages.

[4] The cell preparation for treating central nervous system diseases/damages according to [1], for use in treatment of spinal cord damages.

[5] The cell preparation for treating central nervous system diseases/damages according to [1], for use in treatment of neurodegenerative diseases.

[6] The cell preparation for treating central nervous system diseases/damages according to [1], for use in treatment of brain tumors.

[7] The cell preparation for treating central nervous system diseases/damages according to [1] to [6], wherein the suicide gene is inserted immediately 3' to a translation region of V-actin gene in the pluripotent stem cell.

[8] The cell preparation for treating central nervous system diseases/damages according to [7], wherein a sequence coding for 2A peptide is linked immediately 3' to the translation region of β-actin gene in the pluripotent stem cell, and the suicide gene is linked 3' to the sequence coding for 2A peptide.

[9] The cell preparation for treating central nervous system diseases/damages according to [1] to [8], wherein the neural stem cells do not comprise a selection marker gene in the genome thereof.

[10] The cell preparation for treating central nervous system diseases/damages according to [9], wherein the neural stem cells are obtained by a method comprising the following steps (A) to (D):

(A) inserting a gene construct into the genome of pluripotent stem cells by genome editing, wherein the gene construct is a gene construct which comprises a suicide gene, a selection marker gene, and two target sequences of Cre protein, and in which the selection marker gene is flanked by the two target sequences of Cre protein;

(B) selecting pluripotent stem cells in which the suicide gene has been inserted into the genome thereof from the pluripotent stem cells obtained in the step (A) using the selection marker gene;

(C) removing the selection marker gene from the genome of the pluripotent stem cells obtained in the step (B) by using Cre protein; and (D) differentiating the pluripotent stem cells obtained in the step (C) into neural stem cells.

[11] The cell preparation for treating central nervous system diseases/damages according to [10], wherein the target sequences of Cre protein are loxP sequences.

[12] The cell preparation for treating central nervous system diseases/damages according to [10], wherein the two target sequences of Cre protein included in the gene construct are a mutant loxP sequence having a mutation in an upstream repetitive sequence and a mutant loxP sequence having a mutation in a downstream repetitive sequence, the mutant loxP sequence having a mutation in the upstream repetitive sequence is located upstream of the selection marker gene, and the mutant loxP sequence having a mutation in the downstream repetitive sequence is located downstream of the selection marker gene in the gene construct.

[13] The cell preparation for treating central nervous system diseases/damages according to [9], wherein the neural stem cells are obtained by a method comprising the following steps (a) to (d):

(a) inserting the gene construct into the genome of pluripotent stem cells by genome editing, wherein the gene construct is a gene construct which comprises a suicide gene, a selection marker gene, a mutant loxP sequence having a mutation in a repetitive sequence, and a mutant loxP sequence having a mutation in a spacer sequence, and in which the selection marker gene is flanked by the two mutant loxP sequences;

(b) selecting pluripotent stem cells in which the suicide gene has been inserted in the genome from the pluripotent stem cells obtained in the step (a) by using the selection marker gene;

(c) removing the selection marker gene from the genome of the pluripotent stem cells obtained in the step (b) by using Cre protein and a homologous recombination vector and inserting a second gene into the genome, wherein the homologous recombination vector comprises the second gene, the mutant loxP sequence having a mutation in a repetitive sequence, and the mutant loxP sequence having a mutation in a spacer sequence, and the second gene is flanked by the two mutant loxP sequences; and (d) differentiating the pluripotent stem cells obtained in the step (c) into neural stem cells.

[14] The cell preparation for treating central nervous system diseases/damages according to [10] to [13], wherein the genome editing uses CRISPR/Cas3.

[15] The cell preparation for treating central nervous system diseases/damages according to [1] to [14], wherein the suicide gene is cytosine deaminase gene and uracil phosphoribosyltransferase gene.

[16] The cell preparation for treating central nervous system diseases/damages according to [15], which is used in combination with a prodrug that is converted to 5-fluorouracil by cytosine deaminase.

[17] The cell preparation for treating central nervous system diseases/damages according to [1] to [16], wherein the neural stem cells are neural stem cells in which the expression level of at least one selected from ephrin A receptor, ephrin A, ephrin B receptor, ephrin B, and CXC motif chemokine receptor 4 has been increased.

[18] The cell preparation for treating central nervous system diseases/damages according to [17], wherein the neural stem cells are neural stem cells in which the expression levels of ephrin A, ephrin A receptor, ephrin B receptor, ephrin B, and CXC motif chemokine receptor 4 have been increased.

[19] The cell preparation for treating central nervous system diseases/damages according to [1] to [16], wherein the neural stem cells are selected by using the expression level of at least one selected from ephrin A, ephrin A receptor, ephrin B receptor, ephrin B and CXC motif chemokine receptor 4 as an indicator.

[20] The cell preparation for treating central nervous system diseases/damages according to [19], wherein the neural stem cells are selected by using ephrin A, ephrin A receptor, ephrin B receptor, ephrin B, and CXC motif chemokine receptor 4 as indicators.

[21]A method for preparing neural stem cells, comprising the following steps (1) and (2):

(1) inserting a suicide gene immediately 3' to a translation region of β-actin gene in pluripotent stem cells by genome editing; and (2) differentiating the pluripotent stem cells obtained in the step (1) into neural stem cells.

[22] The method for preparing neural stem cells according to [21], wherein the suicide gene is inserted immediately 3' to the translation region of β-actin gene in the pluripotent stem cells, so that a sequence coding for 2A peptide is linked immediately 3' to the translation region of β-actin gene, and the suicide gene is linked 3' to the sequence coding for 2A peptide in the step (1).

[23] The method for preparing neural stem cells according to [21] or [22], wherein the step (1) comprises the following steps (1-A) to (1-C):

(1-A) inserting a gene construct immediately 3' to a translation region of β-actin gene in pluripotent stem cells by genome editing, wherein the gene construct is a gene construct which comprises a suicide gene, a selection marker gene, and two target sequences of Cre protein, and in which the selection marker gene is flanked by the two target sequences of Cre protein;

(1-B) selecting pluripotent stem cells in which the suicide gene has been inserted into the genome from the pluripotent stem cells obtained in the step (1-A) by using the selection marker gene; and (1-C) removing the selection marker gene from the genome of the pluripotent stem cells obtained in the step (1-B) by using Cre protein.

[24] The method for preparing neural stem cells according to [23], wherein the target sequences of Cre protein are loxP sequences.

[25] The method for preparing neural stem cells according to [23], wherein the two target sequences of Cre protein included in the gene construct are a mutant loxP sequence having a mutation in an upstream repetitive sequence and a mutant loxP sequence having a mutation in a downstream repetitive sequence, the mutant loxP sequence having a mutation in the upstream repetitive sequence is located upstream of the selection marker gene, and the mutant loxP sequence having a mutation in the downstream repetitive sequence is located downstream of the selection marker gene in the gene construct.

[26] The method for preparing neural stem cells according to [21] or [22], wherein the step (1) comprises the following steps (1-a) to (1-c):

(1-a) inserting the gene construct immediately 3' to a translation region of β-actin gene in pluripotent stem cells by genome editing, wherein the gene construct is a gene construct which comprises a suicide gene, a selection marker gene, a mutant loxP sequence having a mutation in a repetitive sequence, and a mutant loxP sequence having a mutation in a spacer sequence, and in which the selection marker gene is flanked by the two mutant loxP sequences;

(1-b) selecting pluripotent stem cells in which the suicide gene has been inserted into the genome from the pluripotent stem cells obtained in the step (1-a) by using the selection marker gene; and (1-c) removing the selection marker gene from the genome of the pluripotent stem cells obtained in the step (1-b) by using Cre protein and a homologous recombination vector and inserting a second gene into the genome, wherein the homologous recombination vector is a homologous recombination vector which comprises the second gene, a mutant loxP sequence having a mutation in a repetitive sequence, and a mutant loxP sequence having a mutation in a spacer sequence, and in which the second gene is flanked by the two mutant loxP sequences.

[27] The method for preparing neural stem cells according to [23] to [26], wherein the genome editing uses CRISPR/Cas3.

[28] The method for preparing neural stem cells according to [21] to [27], wherein the suicide gene is cytosine deaminase gene and uracil phosphoribosyltransferase gene.

[29]A method for estimating the antitumor effect of the cell preparation for treating central nervous system diseases/damages on brain tumor cells according to [15], comprising a step of measuring the expression levels of thymidylate synthase gene and dihydropyrimidine dehydrogenase gene in the brain tumor cells.

[30]A method for selecting neural stem cells with high migratory property and/or anisotropic property for a tumor or damage site, wherein the expression level of at least one selected from ephrin A, ephrin A receptor, ephrin B receptor, ephrin B, and CXC motif chemokine receptor 4 is used as an indicator.

[31] The selecting method according to [30], wherein the expression levels of ephrin A, ephrin A receptor, ephrin B receptor, ephrin B, and CXC motif chemokine receptor 4 are used as indicators.

[32]A cell preparation for treating tumors, comprising neural stem cells prepared by the method according to [21] to [28], the neural stem cells differentiated from pluripotent stem cells into which a suicide gene has been introduced.

[33] The cell preparation for treating tumors according to [32], wherein the neural stem cells do not comprise a selection marker gene in the genome thereof.

[34] The cell preparation for treating tumors according to [32] or [33], wherein the neural stem cells are neural stem cells in which the expression level of at least one selected from ephrin A receptor, ephrin A, ephrin B receptor, ephrin B, and CXC motif chemokine receptor 4 has been increased.

[35] The cell preparation for treating tumors according to [34], wherein the neural stem cells are neural stem cells in which the expression levels of ephrin A, ephrin A receptor, ephrin B receptor, ephrin B, and CXC motif chemokine receptor 4 have been increased.

[36] The cell preparation for treating tumors according to [32] or [33], wherein neural stem cells are selected using the expression level of at least one selected from ephrin A, ephrin A receptor, ephrin B receptor, ephrin B, and CXC motif chemokine receptor 4 as an indicator.

[37] The cell preparation for treating tumors according to [34], wherein the neural stem cells are selected using ephrin A, ephrin A receptor, ephrin B receptor, ephrin B, and CXC motif chemokine receptor 4 as indicators.

[38] The cell preparation for treating tumors according to [32] to [37], wherein the tumors include pancreatic cancer.

The present specification includes the contents described in the description and/or the drawings of Japanese Patent Application Nos. 2020-063477, 2020-165847, and 2020-219455, which are the bases of the priority of the present application.

Advantageous Effects of Invention

The present invention provides a novel preparation for treating tumors and cell preparation for treating central nervous system diseases/damages. In particular, when a cell preparation is used for the treatment of traumatic brain damages including cerebral contusion and brain dysfunctions due to cerebral infarction and the like or for the treatment of neurodegenerative diseases resulting from loss of nerve cells due to nerve degeneration, tumorigenesis of cells becomes of concern. However, the cell preparation of the present invention is a highly safe cell preparation because cells can be killed by a suicide gene.

BRIEF DESCRIPTION OF DRAWINGS

FIG. 16F shows the results of the genomic PCR in Example 3 (4).

FIG. 25A shows a method for removing the drug resistance or fluorescence gene (2).

FIG. 27A shows a method for inserting the second gene (2).

FIG. 33A shows the anisotropic property and migratory property of neural stem cells for pancreatic cancer (1).

FIG. 33B shows the anisotropic property and migratory property of neural stem cells for pancreatic cancer (2).

DESCRIPTION OF EMBODIMENTS

Figure 1A:
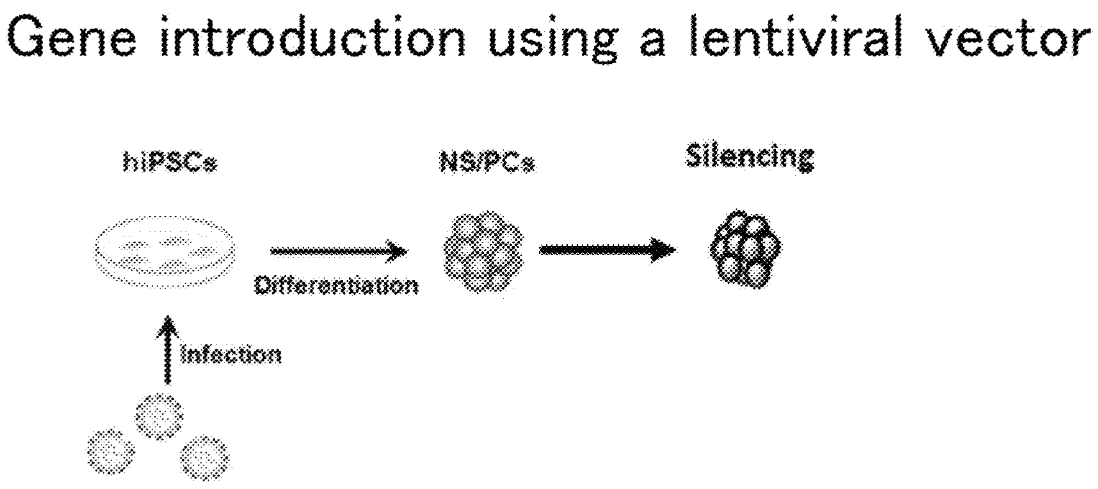
FIG. 1A shows the expression of a suicide gene and establishment of therapeutic neural stem cells (NSCs) (1).

The present invention will be described in detail hereinafter.

(A) Cell Preparation

The preparation for treating tumors and cell preparation for treating central nervous system diseases/damages of the present invention comprise neural stem cells differentiated from pluripotent stem cells into which a suicide gene has been introduced.

Examples of suicide genes include herpes simplex virus thymidine kinase (HSVtk) gene, carboxylesterase gene, deoxycytidine kinase gene and cytosine arabinoside gene, and cytosine deaminase (CD) gene and uracil phosphoribosyltransferase (UPRT) gene (CD-UPRT gene). In the present invention, preferred examples thereof include cytosine deaminase (CD) gene and uracil phosphoribosyltransferase (UPRT) gene (CD-UPRT gene).

The "cell preparation for treating central nervous system diseases/damages" in the present invention means a cell preparation for treating central nervous system diseases and central nervous system damages, more specifically, a cell preparation used for treating diseases and damages in the central nervous system (for example, brain and spinal cord). Diseases and damages to be treated are not particularly limited, and examples thereof include brain tumors, neurodegenerative diseases, brain dysfunctions, and spinal cord damages, preferably brain tumors and brain dysfunctions. Brain dysfunctions to be treated are not particularly limited, and examples thereof include dysfunctions caused by physical injuries such as, for example, dysfunctions due to cerebral contusion and dysfunctions caused by cerebrovascular disorders (for example, cerebral infarction, cerebral hemorrhage, subarachnoid hemorrhage). The "neurodegenerative diseases" means diseases caused by the loss of nerve cells due to nerve degeneration, and specific examples thereof include Parkinson's disease, Alzheimer's disease, Huntington's disease, and frontotemporal lobar degeneration. Examples of brain tumors include glioma (neuroglioma), medulloblastoma, neuroblastoma, meningioma, pituitary gland adenoma, neurilemmoma, primary central nervous system lymphoma and sarcoma, and spinal cord tumor. In the present invention, all of these brain tumors can be treated, but glioma is preferably treated. To be note, when the cell preparation of the present invention is used to treat brain tumors, "treatment" includes not only killing tumor cells, but also reducing the number of tumor cells and inhibiting proliferation of tumor cells.

The "cell preparation for treating tumors" in the present invention means a cell preparation used for the treatment of tumors. The cell preparation of the present invention allows a suicide gene to act on tumor tissue by making use of the migratory property and anisotropic property for tumor tissue, which are characteristic to neural stem cells. The term "treatment" used herein includes not only killing tumor cells, but also reducing the number of tumor cells and inhibiting proliferation of tumor cells. Because of the characteristics of neural stem cells, examples of tumors to be treated include not only brain tumors and pancreatic cancer mentioned in the examples, but also many tumors such as, for example, breast cancer, stomach cancer and lung cancer.

The "pluripotent stem cells" in the present invention can be interpreted as a meaning which those skilled in the art usually use, and include, for example, iPS cells and ES cells. Although ES cells can also be used as pluripotent stem cells, it is preferable to use iPS cells. As long as iPS cells to be used can be differentiated into neural stem cells, the origin thereof, a reprogramming factor to be introduced, a method for introducing the reprogramming factor, and the like are not particularly limited. Since the cell preparation of the present invention is used mainly for treating diseases and damages in the human brain, it is preferable to use human-derived iPS cells in these cases. In this case, iPS cells derived from a patient to whom the cell preparation is to be administered may be used, and iPS cells derived from a human other than the patient may be used. Although iPS cells to be used may be prepared in accordance with a known method, iPS cells can also be obtained from research institutions such as the Center for iPS Cell Research and Application (CiRA), Kyoto University.

The "neural stem cells" in the present invention means stem cells having the capability to supply cells which differentiate into neurons and glia cells. The cell preparation of the present invention comprises these neural stem cells. As long as the cell preparation does not exert a great adverse influence on the effect of treating brain damages and brain diseases, the cell preparation may contain cells other than neural stem cells. When neural stem cells are prepared from iPS cells in accordance with a method described in below-mentioned Sugai K. Mol Brain, 2016, not only neural stem cells but also neural precursor cells are produced. For this reason, the cell preparation of the present invention may contain both neural stem cells and neural precursor cells.

When neural stem cells have higher migratory property and anisotropic property for tumors, more neural stem cells can be accumulated at a disease or damage site, and high therapeutic effects can be expected. Therefore, it is preferable to increase the expression levels of ligand-receptor pairs associated with the above-described migratory property and anisotropic property which are expressed in neural stem cells, specifically, ephrin A, ephrin A receptor, ephrin B, ephrin B receptor, and CXC motif chemokine receptor 4 in neural stem cells. It is preferable to increase the expression levels of all these five, i.e., ephrin A, ephrin A receptor, ephrin B, ephrin B receptor, and CXC motif chemokine receptor 4, but the expression levels of only three of them, ephrin B, ephrin B receptor, and CXC motif chemokine receptor 4, can be increased, or the expression level of at least one selected from these three can be increased. The expression levels of these ligands and receptors can be increased in accordance with known methods. For example, they can be increased by a method for introducing the genes of these ligands and receptors into neural stem cells (may be introduced together with a regulatory region for increasing the gene expression levels, such as an enhanced expression promoter, if necessary), a method using a substance having an effect of increasing the expression levels of these ligands and receptors, or the like.

Furthermore, since high therapeutic effects can also be expected by using neural stem cells having high migratory property and anisotropic property for tumors by nature, neural stem cells selected by the selecting method of the present invention described later may be used as neural stem cells.

Carboxylesterase converts CPT-11 to highly toxic 7-ethyl-10-hydroxycamptothecin and inhibits topoisomerase I potently. Cytosine arabinoside is phosphorylated by the deoxycytidine kinase gene and exhibits antitumor effects. The CD gene and the UPRT gene are suicide genes induced by prodrugs 5-fluorocytosine (5-FC) and 5-fluorouracil (5-FU), respectively. These vectors that express suicide genes are commercially available, and pluripotent stem cells and neural stem cells in which these suicide genes are expressed can be prepared by using such vectors. The CD gene and the UPRT gene each have antitumor effects solely, but approximately 100 times higher antitumor effects can be obtained by introducing these two genes into a cell, compared with when the CD gene alone is introduced.

A suicide gene may be introduced into a pluripotent stem cell by using a viral vector, but it is preferable to perform genome editing. This is because, when a suicide gene is inserted into the genome of a pluripotent stem cell by using a viral vector such as lentiviral vector, the suicide gene is inserted into the chromosome randomly, thus raising concerns about gene mutation at the insertion site, activation of surrounding genes and inactivation of the suicide gene due to positional effect. It is considered that such problems can be avoided not by using a viral vector, but by performing genome editing.

The genome can be edited using ZFN, TALEN, CRISPR/Cas9, CRISPR/Cas3, Cre/loxP or the like. Among these, it is preferable to edit the genome using CRISPR/Cas9 or CRISPR/Cas3, and it is particularly preferable to edit the genome using CRISPR/Cas3. Since the recognition target sequence of CRISPR/Cas3 is longer than that of CRISPR/Cas9, off-target effect occurs infrequently, and neural stem cells with higher safety can be prepared. By genome editing, a suicide gene can be inserted into a housekeeping gene region or a safe harbor region AAVS1 in a pluripotent stem cell. Examples of housekeeping genes include β-actin gene, glyceraldehyde-3-phosphate dehydrogenase (GAPDH) gene, cyclophilin gene, and α-tubulin gene. In the present invention, it is preferable to insert a suicide gene immediately 3' to a translation region of β-actin gene. Furthermore, at this time, the suicide gene is preferably inserted immediately 3' to the translation region of β-actin gene, so that a sequence coding for 2A peptide is linked immediately 3' to the translation region of β-actin gene, and that the suicide gene is linked 3' to the sequence coding for 2A peptide.

When a suicide gene is introduced into a pluripotent stem cell, usually, a foreign selection marker gene, such as a drug resistance gene or a fluorescence gene, is also introduced together to select cells. However, it is not desirable in view of safety that a foreign gene such as a selection marker gene remains in the genome of a neural stem cell differentiated from a pluripotent stem cell. Therefore, it is preferable to remove the selection marker gene. Means for removing the selection marker gene are not particularly limited, but it is preferable to use a combination of Cre protein and a target sequence of Cre protein, such as the Cre/loxP system. The term "target sequence of Cre protein" used herein refers to the loxP sequence (SEQ ID NO: 1), a loxP sequence having a mutation (mutant loxP sequence), or the like. The loxP sequence consists of an upstream repetitive sequence, a spacer sequence, and a downstream repetitive sequence, and a mutation in a mutant loxP sequence can exist in any of these sequences. Specific examples of mutant loxP sequences having a mutation in the upstream repetitive sequence include lox71 (SEQ ID NO: 2). Specific examples of mutant loxP sequences having a mutation in the spacer sequence include lox2272 (SEQ ID NO: 4). Specific examples of mutant loxP sequences having a mutation in the downstream repetitive sequence include lox66 (SEQ ID NO: 3).

Examples of methods comprising removing the selection marker gene by using the Cre/loxP system include a method comprising preparing a gene construct which comprises a suicide gene, a selection marker gene, and two loxP sequences, and in which the selection marker gene is flanked by the two loxP sequences, inserting this gene construct into the genome of a pluripotent stem cell, and then removing the selection marker gene from the genome of the pluripotent stem cell by Cre protein. However, this method has a risk that one loxP sequence may remain in the genome of a pluripotent stem cell and react with Cre protein. Accordingly, it is preferable to replace the loxP sequence included in the gene construct with a mutant loxP sequence, so that the loxP sequence remaining in the genome is a mutant loxP sequence that hardly reacts with Cre protein. Specific examples of the method include a method comprising preparing a gene construct in which the two loxP sequences included in the gene construct are replaced with a mutant loxP sequence having a mutation in the upstream repetitive sequence and a mutant loxP sequence having a mutation in the downstream repetitive sequence, the mutant loxP sequence having a mutation in the upstream repetitive sequence is located upstream of the selection marker gene, and the mutant loxP sequence having a mutation in the downstream repetitive sequence is located downstream of the selection marker gene; inserting this gene construct into the genome of a pluripotent stem cell; and then removing the selection marker gene from the genome of the pluripotent stem cell by using Cre protein. In this method, mutant loxP sequences having mutations in the upstream repetitive sequence and the downstream repetitive sequence remain in the genome, and thus a risk of reaction with Cre protein can be reduced.

By using a homologous recombination vector in addition to the above-described gene construct, not only the selection marker gene can be removed from the genome, and but also a second gene can be inserted into the genome at the same time. In this case, the gene construct used is a gene construct which comprises a suicide gene, a selection marker gene, a mutant loxP sequence having a mutation in the repetitive sequence, and a mutant loxP sequence having a mutation in the spacer sequence, and in which the selection marker gene is flanked by the two mutant loxP sequences. Furthermore, the homologous recombination vector used is a homologous recombination vector which comprises a second gene, a mutant loxP sequence having a mutation in the repetitive sequence, and a mutant loxP sequence having a mutation in the spacer sequence, and in which the second gene is flanked by the two mutant loxP sequences. As the second gene, a gene involved in treatment which is not a suicide gene can be used.

Figure 22:
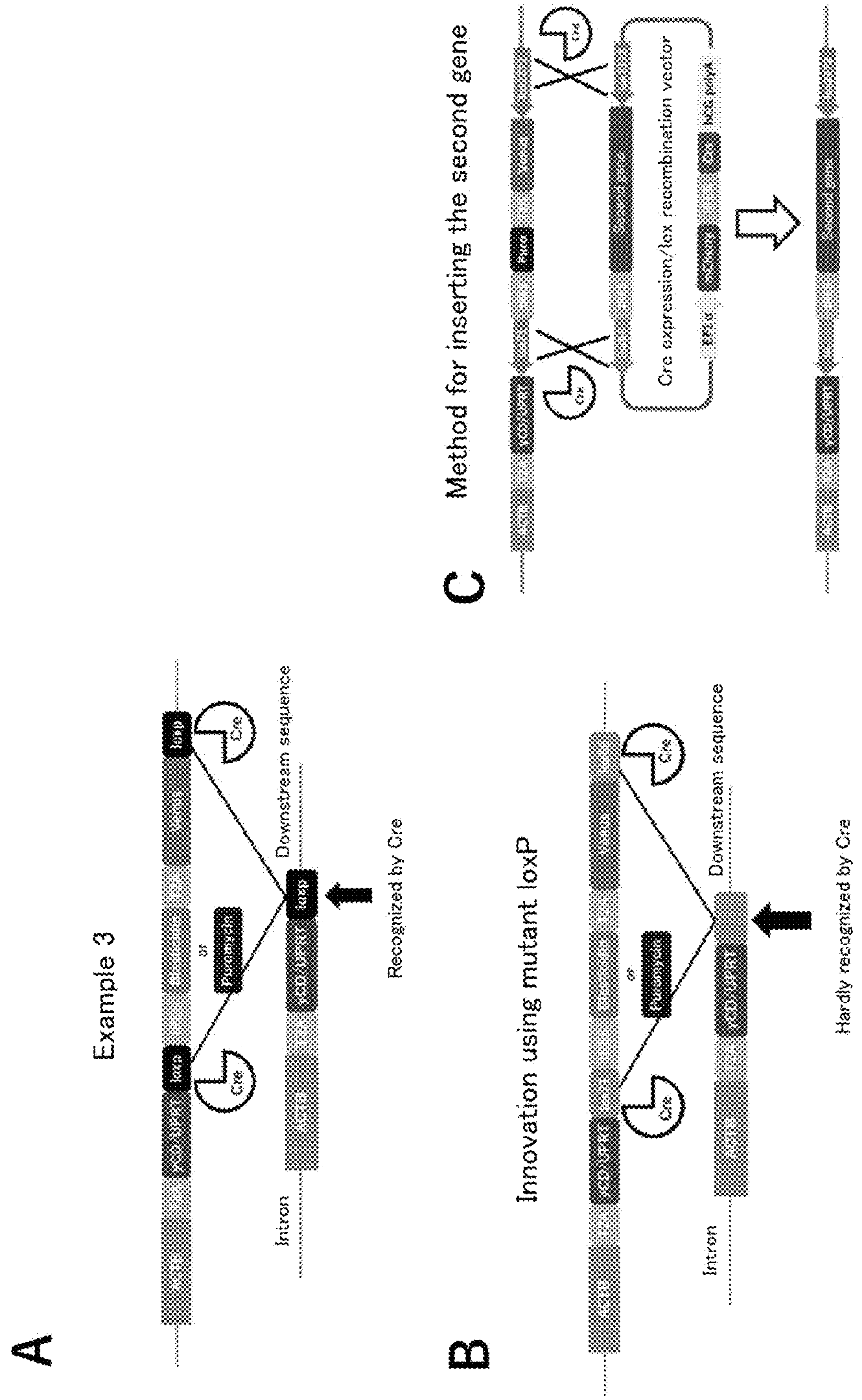
FIG. 22 shows a method for removing an antibiotic resistance gene using the Cre/mutant lox system and a method for inserting the second gene using the Cre/mutant lox system schematically.

Positions of the mutant loxP sequences in the gene construct are not particularly limited. As shown in FIG. 22C, the mutant loxP sequence having a mutation in the repetitive sequence may be positioned upstream of the selection marker gene, and the mutant loxP sequence having a mutation in the spacer sequence may be positioned downstream of the selection marker gene, or the other way round. However, when the mutant loxP sequence having a mutation in the repetitive sequence is positioned upstream of the selection marker gene, it is preferable that the mutant loxP sequence has a mutation in the upstream repetitive sequence. Conversely, when the mutant loxP sequence having a mutation in the repetitive sequence is positioned downstream of the selection marker gene, it is preferable that the mutant loxP sequence has a mutation in the downstream repetitive sequence. Consequently, the mutant loxP sequences remain in the genome.

The positions of the mutant loxP sequences in the homologous recombination vector should be similar to those of the mutant loxP sequences in the gene construct. Specifically, when the mutant loxP sequence having a mutation in the repetitive sequence is positioned upstream of the selection marker gene, and the mutant loxP sequence having a mutation in the spacer sequence is positioned downstream of the selection marker gene in the gene construct, the mutant loxP sequence having a mutation in the repetitive sequence should be positioned upstream of the second gene in the homologous recombination vector, and the mutant loxP sequence having a mutation in the spacer sequence should be positioned downstream of the second gene. When the positions of the mutant loxP sequences in the gene construct are opposite to the above-described positions, the positions of the mutant loxP sequences in the homologous recombination vector should also be opposite to the above-described positions.

When Cre protein and the above-described homologous recombination vector are allowed to act on the genome into which the above-described gene construct has been inserted, homologous recombination occurs, the selection marker gene is removed from the genome, and the second gene is inserted into the genome at the same time. The gene coding for Cre protein may be inserted into the homologous recombination vector beforehand to allow Cre protein and the homologous recombination vector to act at the same time.

Differentiation from pluripotent stem cells into neural stem cells may be performed in accordance with either of well-known methods of a method for preparation through embryoid bodies and a method for preparation without forming embryoid bodies. When differentiation from iPS cells is performed, the differentiation from the iPS cells can be performed, for example, in accordance with the method described in Stem Cell Reports. 2017 Nov. 14; 9(5):1675-1691. According to the above-mentioned method, embryoid bodies can be formed from iPS cells using a well-known embryoid-forming medium, and the embryoid medium contains a TGFβ family inhibitor (for example, SB431542) and a BMP inhibitor (for example, LDN-193189). Differentiation from the embryoid bodies into neural stem cells can be performed using a well-known neurosphere medium. For example, the neurosphere medium contains an epithelial growth factor, a fibroblast growth factor-2, a leukemia inhibitory factor, a B-27 supplement, and the like. Culturing the embryoid bodies in the neurosphere medium forms cell aggregates called neurospheres and containing neural stem cells. The formed neurospheres are collected and dissociated into single cells. The single cells are cultured in neurosphere medium to form neurospheres again. Such operation is repeated several times, and neural stem cells can be obtained by collecting neurospheres.

As described above, "neural stem cells," which are a "product," are not specified by structure or properties but specified by a preparation method herein. This is because since cells are part of the living body, the structure and properties thereof are very complicated, and markedly excessive economic expenditure and time are taken to work to specify them.

The cell preparation of the present invention may contain other pharmaceutically acceptable components besides neural stem cells. Examples of such other components include carriers, excipients, disintegrators, buffers, emulsifiers, suspending agents, soothing agents, stabilizers, preservatives, antiseptics, and physiological saline solutions. Dimethyl sulfoxide, serum albumin or the like may be contained to protect cells at the time of freeze storage, and an antibiotics and the like may be contained to prevent the contamination and proliferation of bacteria.

The number of neural stem cells contained in the cell preparation of the present invention can be optionally determined in view of the type of the disease, such as a tumor, brain disease, or brain damage, sex, age, or weight of a subject, the state of the affected part, the state of cells to be used or the like to obtain desired effects in the treatment of tumors, brain diseases, and brain damages.

The cell preparation of the present invention may be administered a plurality of times (for example, 2 to 10 times) at intervals (for example, twice per day, once per day, twice per week, once per week, once per two week). Although the dose can be optionally determined in view of the type of the disease or damage, sex, age, or weight of a subject, the state of an affected area, the state of cells to be used or the like, the administration is preferably $1\times10^6$ to $1\times10^{10}$ stem cells per individual (human) 1 to ten times.

The administration sites and the administration methods of the cell preparation of the present invention are not particularly limited. Examples of the administration methods include local administration to the brain or tumor tissue, intracarotid administration, and intravenous administration.

The cell preparation of the present invention may be used in combination with a prodrug activated by a suicide gene. The prodrug can be selected depending on the type of the suicide gene. For example, when the CD-UPRT gene is used as a suicide gene, a prodrug converted to 5-fluorouracil by cytosine deaminase (for example, 5-FC) can be used. By using such a prodrug, cell death can be induced in cells having a suicide gene. Whether a prodrug is used or not can be decided depending on the disease or damage to be treated. For example, when brain dysfunction is treated, use of the prodrug is not necessarily required because induction of cell death by using a prodrug is not directly associated with therapeutic effects, but aims to kill tumor cells or kill cells with potential tumorigenesis. In contrast, when brain tumor is treated, use of a prodrug is essential because induction of cell death by using a prodrug is directly associated with therapeutic effects.

The administration sites and administration methods of a prodrug are not particularly limited. Examples of administration methods include intraperitoneal administration in addition to oral administration, local administration to the brain or tissue, intracarotid administration, and intravenous administration.

The timing for administering a prodrug can be selected depending on the disease or damage to be treated. For example, when a brain damage is treated, the prodrug may be administered at the timepoint when tumor cells develop, or administration of the cell preparation of the present invention may be started after a specific time elapses to prevent tumor cells from developing. The timings for starting such prophylactic administration are not particularly limited as long as they are timings when therapeutic effects of neural stem cells are not lost, and undifferentiated cells having a risk of tumorigenesis can be killed. For example, the prodrug may be administered at 3 to 60 days or 5 to 20 days after administration of the cell preparation of the present invention. Furthermore, when a brain tumor is treated, the prodrug may be administered before, during, or after administration of the cell preparation of the present invention, but is usually divided into multiple doses and administered after administration of the cell preparation. The prodrug is similarly administered for other tumors.

The dose of the prodrug can be optionally determined in view of the type of the prodrug used, the type of the disease or damage, sex, age, and weight of a subject, the state of an affected area or the like. When 5-FC is administered, it is preferable to administer a dose of 50 to 200 mg/kg per day per individual (human) divided into 4 doses per day.

(B) Method for Preparing Neural Stem Cells

The method for preparing the neural stem cells of the present invention is characterized by comprising the following steps (1) and (2).

In the step (1), a suicide gene is inserted immediately 3' to a translation region of V-actin gene in pluripotent stem cells by genome editing. This step can be performed in a similar manner to introduction of a suicide gene into pluripotent stem cells described in "(A) Cell preparation."

In the step (2), the pluripotent stem cells obtained in the step (1) are differentiated into neural stem cells. This step can be performed in a similar manner to differentiation of pluripotent stem cells into neural stem cells described in "(A) Cell preparation."

(C) Method for Estimating Antitumor Effects

The method for estimating antitumor effects of the present invention is a method for estimating the antitumor effect of the above-described cell preparation for treating central nervous system diseases/damages of the present invention on brain tumor cells, which comprises a step of measuring the expression levels of thymidylate synthase gene and dihydropyrimidine dehydrogenase gene in the brain tumor cells.

The expression level of a gene can be measured by known methods such as, for example, RT-qPCR technique.

If the measurement result shows that the expression levels of thymidylate synthase gene and dihydropyrimidine dehydrogenase gene are high, it can be estimated that the antitumor effect of the cell preparation for treating central nervous system diseases/damages of the present invention on the brain tumor cells subjected to measurement is low. When the expression levels of the above-mentioned genes are low, it can be estimated that the antitumor effect of the cell preparation for treating central nervous system diseases/damages of the present invention on the brain tumor cells subjected to measurement is high.

(D) Method for Selecting Neural Stem Cells with High Migratory Property and Anisotropic Property The selecting method of the present invention is a method for selecting neural stem cells with high migratory property and/or anisotropic property for a tumor or damage site, wherein the cells are selected by using the expression level of at least one selected from ephrin A, ephrin A receptor, ephrin B receptor, ephrin B, and CXC motif chemokine receptor 4 as an indicator.

It is preferable that the cells are selected by using the expression levels of all five of ephrin A, ephrin A receptor, ephrin B, ephrin B receptor, and CXC motif chemokine receptor 4 as indicators, but the cells may be selected by using the expression levels of only three of them, ephrin B, ephrin B receptor, and CXC motif chemokine receptor 4 as indicators or by using the expression level of at least one selected from these three as an indicator.

Specific examples of the selecting methods include a method comprising the following steps (1) and (2):

(1) measuring the expression level of at least one selected from ephrin A, ephrin A receptor, ephrin B receptor, ephrin B, and CXC motif chemokine receptor 4; and (2) selecting the neural stem cells measured in the step (1) whose expression level is higher than the reference value as "neural stem cells with high migratory property and/or anisotropic property for a tumor or damage site."

Here, the reference values used for selection are not particularly limited. For example, the expression level of ephrin A, ephrin A receptor, ephrin B receptor, ephrin B, or CXC motif chemokine receptor 4 in neural stem cells that are commonly used (for example, commercially available neural stem cells) can be measured beforehand and used as a reference value.

EXAMPLES

The present invention will be described in more detail hereinafter by giving examples, but the present invention is not limited to these examples. "NSC" usually refers to "neural stem/progenitor cell (NS/PC)" in the following examples.

Example 1

(A) Method

<Human iPS cells>

The human iPS cells (1210B2) used were obtained from the Center for iPS Cell Research and Application (CiRA), Kyoto University. 1210B2 was established by a method for introducing a reprogramming factor using an episomal vector for human peripheral blood mononuclear cells (Okita K, Yamakawa T, Matsumura Y, Sato Y, Amano N, Watanabe A, Goshima N, Yamanaka S. An efficient nonviral method to generate integration-free human-induced pluripotent stem cells from cord blood and peripheral blood cells. Stem Cells. 2013 March; 31(3):458-66.). Human iPS cells were inoculated on a plastic culture dish coated with iMatrix-511 (produced by Nippi, Incorporated) and subjected to maintenance culture using Stem Fit AK03 or AK03N medium (produced by Ajinomoto Co., Inc.) by a known feeder-free method.

<Differentiation Induction from Human iPS Cells into Neural Stem/Precursor Cells (NSCs)>

Differentiation induction from human iPS cells into NSCs was performed by a known method (Sugai K. Mol Brain. 2016). First, a 10 M ROCK inhibitor Y276352 (produced by Wako Pure Chemical Industries, Ltd.) was added to a medium of iPS cells, the iPS cells were incubated for 1 to 3 hours, then washed with PBS, and dissociated into single cells using TrypLE Select (produced by Life Technologies Corporation). The human iPS cells dissociated into single cells were suspended in an EB (embryoid body)-forming medium to which a 10 M ROCK inhibitor Y276352 was added (10 M SB431542 and 100 nM LDN-193189 were added to Stem Fit medium not containing C liquid), inoculated at a concentration of $9.0\times10^3$ cells/75 μl per well of a low adhesive 96-well culture plate (Prime Surface 96V, manufactured by Sumitomo Bakelite Co., Ltd.) and cultured. Then, 75 μl of an EB-forming medium was added 1 day later, a half amount of the EB-forming medium was replaced every day thereafter, and the human iPS cells were cultured for 13 to 14 days to obtain EBs. The EBs were collected from each well and cultured in a neurosphere (NS) medium (to D-MEM/Ham's F-12 medium (containing HEPES) (produced by Wako Pure Chemical Industries, Ltd.) were added a 20 ng/ml recombination human epidermal growth factor (produced by PeproTech, Inc.), a 20 ng/ml recombination human fibroblast growth factor-2 (produced by PeproTech, Inc.), a $10^3$ units/ml recombination human leukemia inhibitory factor (produced by NACALAI TESQUE, INC.), a 2% B-27 supplement (produced by Thermo Fisher Scientific K.K.), and 1 unit/ml heparin sodium (produced by AY PHARMACEUTICALS CO., LTD.)) for 7 days. The medium was replaced once every 3 or 4 days during culture. Cell aggregates were collected by centrifugation, dissociated into single cells using TrypLE Select, and then suspended in an NS medium. The single cells were inoculated into a low adhesive flask (manufactured by Corning Incorporated) at a concentration of $1\times10^5$ cells/ml, and cultured for 10 days, with the medium replaced every 3 to 4 days, to obtain primary NSCs. Similarly, the primary NSCs were collected by centrifugation, dissociated into single cells using TrypLE Select, and suspended in an NS medium. The single cells were inoculated into a low adhesive flask at a concentration of $1\times10^5$ cells/ml and cultured for 7 to 10 days, with the medium replaced every 3 to 4 days, to obtain secondary, tertiary, quaternary, and quinary NSCs.

<Introduction of yCD-UPRT Gene into GAPDH, ACTB and AAVS1 Gene Regions with CRISPR/Cas9—Preparation of Therapeutic Stem Cells yCD-NSCs>

Preparation of iPS Cells in which yCD-UPRT Gene has been Introduced into Each Gene Region iPS cells were prepared in which the yCD-UPRT fusion suicide gene had been inserted into housekeeping gene regions GAPDH (glyceraldehyde-3-phosphate dehydrogenase) and ACTB (β-actin) and a safe harbor region AAVS1 (PPP1R12C) by using the CRISPR/Cas9 genome editing technique. As DNA constructs for genome editing, a construct for homologous recombination (HR-GAPDH-2A-yCD-UPRT-2A-Bsd) in which GAPDH (glyceraldehyde-3-phosphate dehydrogenase), yCD-UPRT, and Bsd (blasticidin resistance gene) were inserted, being connected by 2A peptide sequences, and an expression vector construct (U6-GAPDH-gRNA4-Cas9) of a gRNA which targets the vicinity to the stop codon of GAPDH and Cas9 were prepared to incorporate yCD-UPRT into the GAPDH gene region. For β-actin, a gRNA expression vector targeting the vicinity of the stop codon of β-actin was constructed as for GAPDH, and a homologous recombination construct (β-actin-2A-yCD-UPRT-2A-Bsd) was constructed so that β-actin, yCD-UPRT, and Bsd were inserted, being connected by 2A peptide sequences. The construct for homologous recombination for the AAVS1 region was constructed so that yCD-UPRT-2A-Bsd was expressed under the EF-1 promoter, and an insulator sequence was added to either end. These genes, yCD-UPRT, and Bsd were inserted, being connected by 2A peptide sequences.

These constructs were introduced into a human iPS cell line 1210B2 by electroporation, and the culture was performed in the presence of blasticidin S, and the cloning was performed. The homologous recombination in the iPS cell line was confirmed by nucleotide sequence confirmation by the genomic PCR and genomic sequencing of clones.

Preparation of yCD-UPRT-Expressing NSCs (yCD-NSCs)

Differentiation induction from iPS cells in which yCD-UPRT had been incorporated into each gene region into NSCs was performed to obtain secondary to quinary NSCs (yCD-NSCs). Culture was performed with 1 g/ml of blasticidin S always added to the medium. It was confirmed that cell death of yCD-UPRT-expressing NSCs was induced by adding 1 to 5 g/ml 5-FC to the medium.

Supplementary Information

Migratory and Antitumor Effects of yCD-NSCs on Malignant Neuroglioma yCD-NSCs (labelled with hKO1) was transplanted to 1 mm above a tumor mass of human glioma cell line U87 (ffLuc), and the migratory property thereof was assessed quantitatively by using a brain section culture (Tamura R. Mol Brain. 2019). Adipose tissue-derived and bone marrow-derived human mesenchymal stem cell lines (labelled with hKO1) were used as comparators. The migratory property in the brain was assessed quantitatively by creating Rose Diagram Maps (Angular histogram) using the direction and the migratory distance as parameters. The antitumor effects of yCD-NSCs were assessed by transplanting yCD-NSCs and administering 5-FC to a mouse model of U87 glioma.

Safety of yCD-NSCs

In the same manner as described above, $5\times10^5$ yCD-NSCs (ffLuc) were transplanted into the right striatum of the normal brain, and 5-FC was administered for 2 weeks from 7 days thereafter. A group untreated with 5-FC was also prepared as controls. Mice were decapitated at 150 days thereafter, and their brain tissues were assessed. 5-FU converted from 5-FC is, in theory, considered not to affect cells in the brain occupied by terminally differentiated cells, but can affect neural precursor cells existing in the vicinity of the cerebral ventricles and slightly divided cells in the vascular endothelium and the like. Therefore, histological assessment was performed by using a vascular endothelial cell marker (CD31) and a neural stem cell/precursor cell marker (Nestin). Furthermore, administration of 5-FC was started at 35 days after transplantation of yCD-NSCs, and the loss of engrafted yCD-NSCs was confirmed with IVIS.

Biomarkers for yCD-NSCs

The susceptibility of 5-FU to U87, U251, SF126, hG008, hG021, GL261, and TSG was assessed (CCK-8 assay). Comparison was made using TMZ as a control. Additionally, the activities of thymidylate synthase (TS) and dihydropyrimidine dehydrogenase (DPD) in each cell line and yCD-NSCs were analyzed quantitively by RT-qPCR and western blotting.

Differentiation of yCD-UPRT-Expressing NSCs into Neurons and Susceptibility of Differentiated Cells to 5-FU yCD-UPRT-expressing NSCs were differentiated into neurons in vitro. Differentiation was confirmed by the expression and morphology of βIII tubulin and NeuN. Remaining proliferated cells that were undifferentiated were confirmed by the expressions of Ki-67, PCNA, and Nestin. Cell deaths were assessed by the expression of cleaved caspase 3. 5-FC was added, and changes in these differentiated cells and undifferentiated cells caused by 5-FU released by the introduced yCD-UPRT were assessed.

Preparation of ffLuc-Expressing yCD-NSCs

The prepared yCD-NSCs were infected with the ffLuc (a fusion gene of Venus fluorescence protein and Luc2 firefly luciferase) expression lentiviral vector (CSII-EF-ffLuc) (Takahashi Y, Tsuji O, Kumagai G, Hara C M, Okano H J, Miyawaki A, Toyama Y, Okano H, Nakamura M. Comparative study of methods for administering neural stem/progenitor cells to treat spinal cord injury in mice. Cell Transplant. 2011; 20(5):727-39.) to obtain yCD-NSCs which express ffLuc highly and steadily.

<Examination of Therapeutic Effects of yCD-NSCs in Cerebral Contusion Mouse Model>

Craniotomy was performed in a circle shape with a diameter of 1.25 mm outer left and 1.25 mm rostal from the anterior fontanel of a T cell-deficient mouse (female BALB/c nude mouse, 20 g, 10 w) subjected to general anesthesia. The bone flap was protected to return it later. The surface of the brain was exposed, and cerebral contusion was created by cooling the surface of the brain (60° C. 30 sec×10 sets) using ACU22XT Amoiros cryosurgical apparatus (Keeler & y.na Ltd.) and a 2.5 mm probe. Subsequently, $1\times10^5$ yCD-NSCs were transplanted from the anterior fontanel to directly under the same contusion site (2.5 mm outer left, 1.25 mm rostal, and 2 mm deep). The isolated bone flap was returned, and skin suture was completed.

To assess the behavior of mice, first, tests were performed preoperatively twice using RotaRod (manufactured by Ugo Basile) and once using Smart Grip Strength Meter for Rats and Mice MK-380Si (manufactured by Muromachi Kikai Co., Ltd.), so that the mice would be skilled for the instruments. RotaRod was used while increasing the rotation speed from 2 rpm through 20 rpm over 300 seconds, and the time to a fall from the rod or appearance of an unstable walk of the mouse was measured. A rota rod test was performed 3 times on each measurement day, and the mean time was obtained. This method was implemented as previously reported (Tabuse J Clin Neurosci. 2010). The grip strength was measured for one limb alone by placing a plastic cover on top of a net attached to the measuring instrument to limit the area of the net that can be gripped. The grip strength was measured for all 4 limbs. When the net was gripped with 5 fingers, the tail was pulled horizontally, and the peak value before the limbs came off from the net was measured. The grip strength was measured 7 times for each limb, and the mean values of 5 measurements, excluding the maximum and minimum values, were compared (Alamri F F. Behav Brain Res. 2018).

Motor function was assessed by the above-described method at 3, 5, 7, 14, 21, 28, 35, and 42 days after the surgery. In the identical animals, changes with time in yCD-NSCs were observed by the in vivo imaging system (IVIS) every week. For IVIS imaging, 200 µl of 30 mg/ml VivoGlo™ Luciferin was administered intraperitoneally under anesthesia by isoflurane inhalation, and imaging was performed for 5 minutes until the peak was reached.

At 7, 14, 28, and 42 days after creation of cerebral contusion, 4 mice each were decapitated, and perfusion fixation was performed to obtain brain tissues. For decapitation, 0.2 ml of a 2% Evans blue (produced by Sigma-Aldrich) solution (the solvent is sterile physiological saline solution) was injected into the caudal vein of each animal at 2 hours before decapitation, and then mice were decapitated.

Furthermore, $1\times10^5$ yCD-NSCs were transplanted, aiming at approximately 1 mm below the contusion (3 mm deep from the surface of the brain), on the same day. Then, the mice were decapitated at day 42, and tissues were assessed. The transplanted yCD-NSCs were assessed using STEM121, an antibody to specific human cells.

<Examination of Safety of yCD-NSCs in Cerebral Contusion Mouse Model>

In the same manner as described above, contusion was created, and yCD-NSCs were transplanted. Then, 5 mg/day of 5-FC was administered intraperitoneally every day for 2 weeks from 7 days thereafter. Motor function (grip strength) was compared with controls of both a group untreated with 5-FC and a group in which yCD-NSCs were not transplanted. Thus, it was confirmed that the release of 5-FU did not have adverse influence on brain functions.

(B) Results

<Establishment of NSCs for Suicide Gene Expression and Treatment>

Figure 1B:
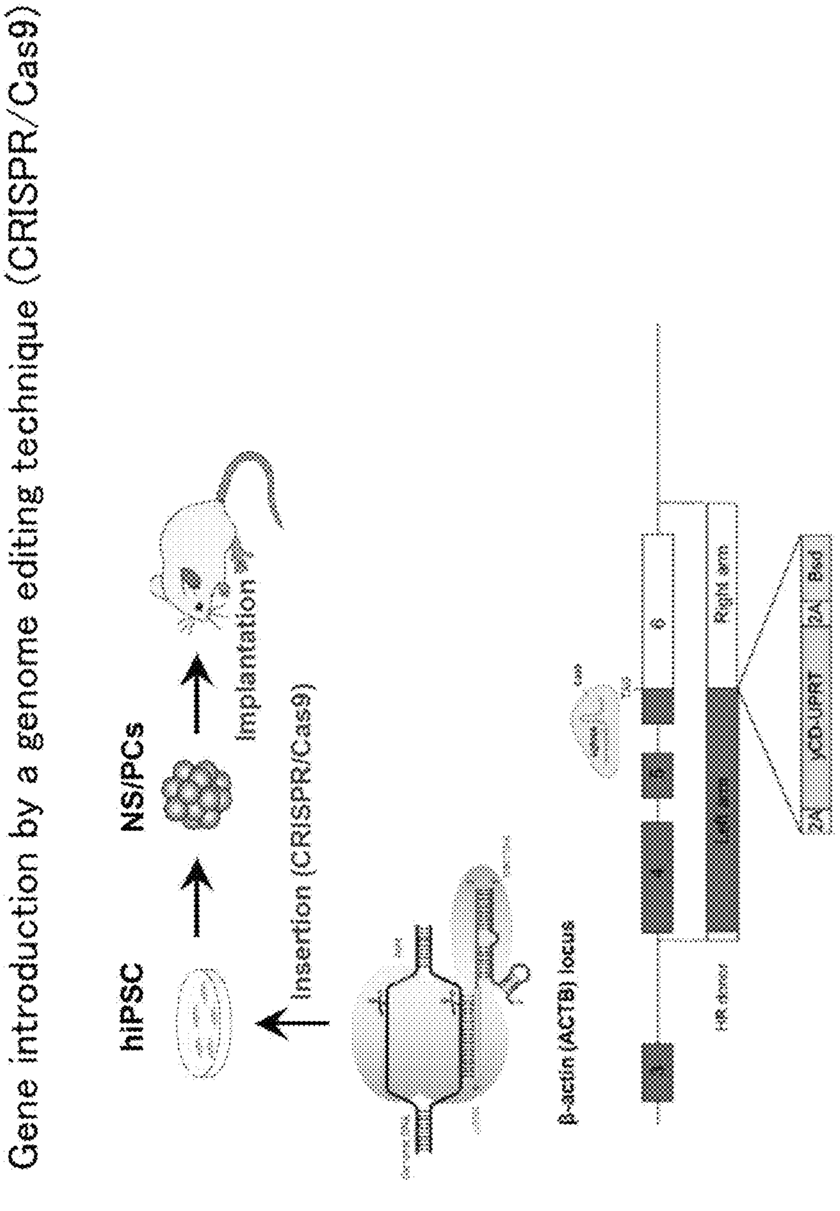
FIG. 1B shows the expression of a suicide gene and establishment of therapeutic NSCs (2).
Figure 1C:
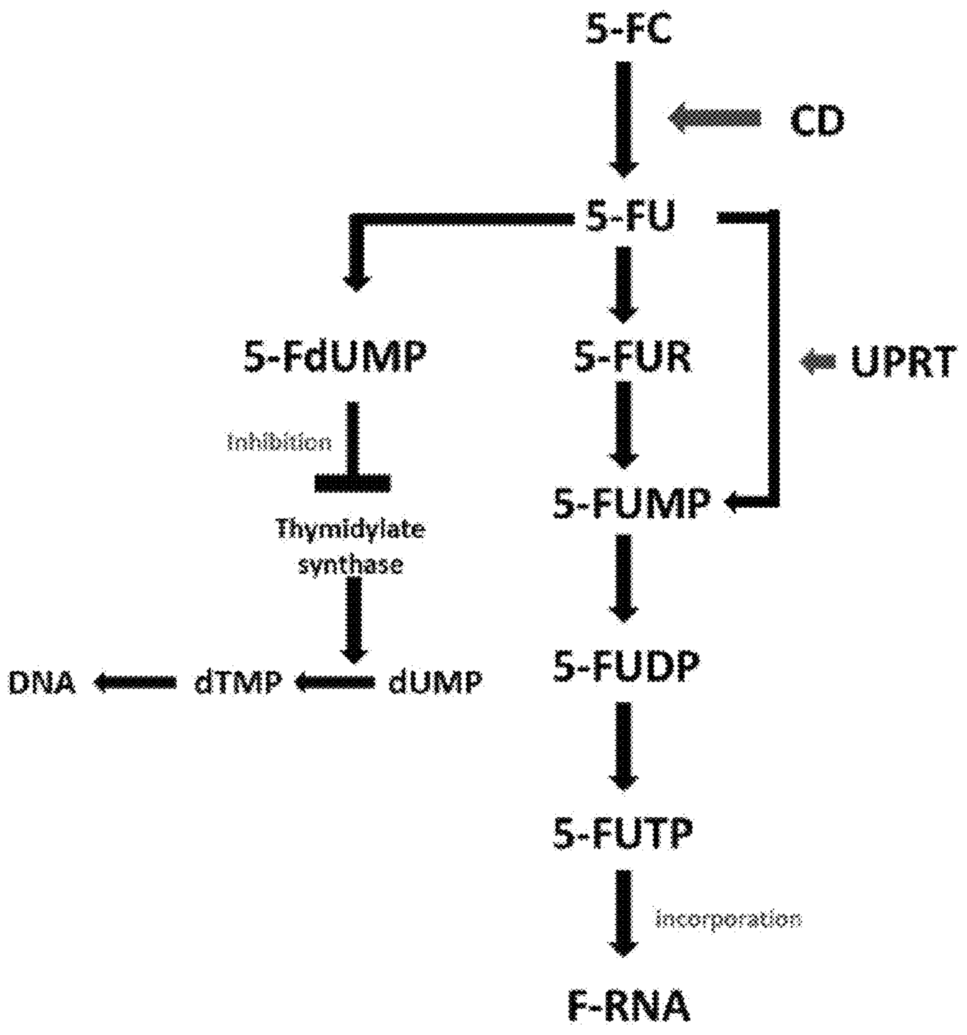
FIG. 1C shows the expression of a suicide gene and establishment of therapeutic NSCs (3).

In the introduction of the suicide gene (yCD-UPRT) into human iPS cells using a lentiviral vector, gene silencing occurred during the process of differentiation induction into neural stem cells/precursor cells (NSCs) (FIG. 1A). Accordingly, the present inventors successfully realized a constantly stable expression of yCD-UPRT by inserting it into the housekeeping gene region β actin (ACTB) using the genome editing technique with CRISPR/Cas9 (FIG. 1B). yCD-UPRT induces cell death by converting an anti-fungal agent 5-FC, which is a prodrug, to an anti-cancer agent 5-FU (FIG. 1C).

Figure 1D:
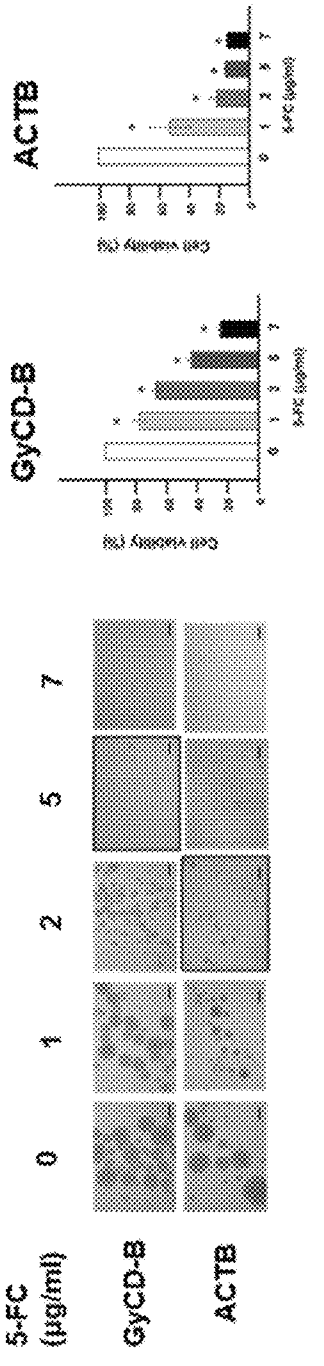
FIG. 1D shows the expression of a suicide gene and establishment of therapeutic NSCs (4).

To optimize the insertion site of a suicide gene, the present inventors also introduced the yCD-UPRT gene into another housekeeping gene GAPDH and a safe harbor region AAVS1 with CRISPR/Cas9. In the AAVS1 region, silencing occurred as seen with the viral vector. In the GAPDH region, the susceptibility to the prodrug 5-FC was less than in the β actin region (FIG. 1D). Accordingly, the present inventors determined that β actin was the optimal gene introduction region for yCD-UPRT. The susceptibility to 5-FC was analyzed quantitatively by CCK-8 assay.

<Antitumor Effects of Therapeutic NSCs (yCD-NSCs) in Malignant Glioma Mouse Model>

Figure 2A:
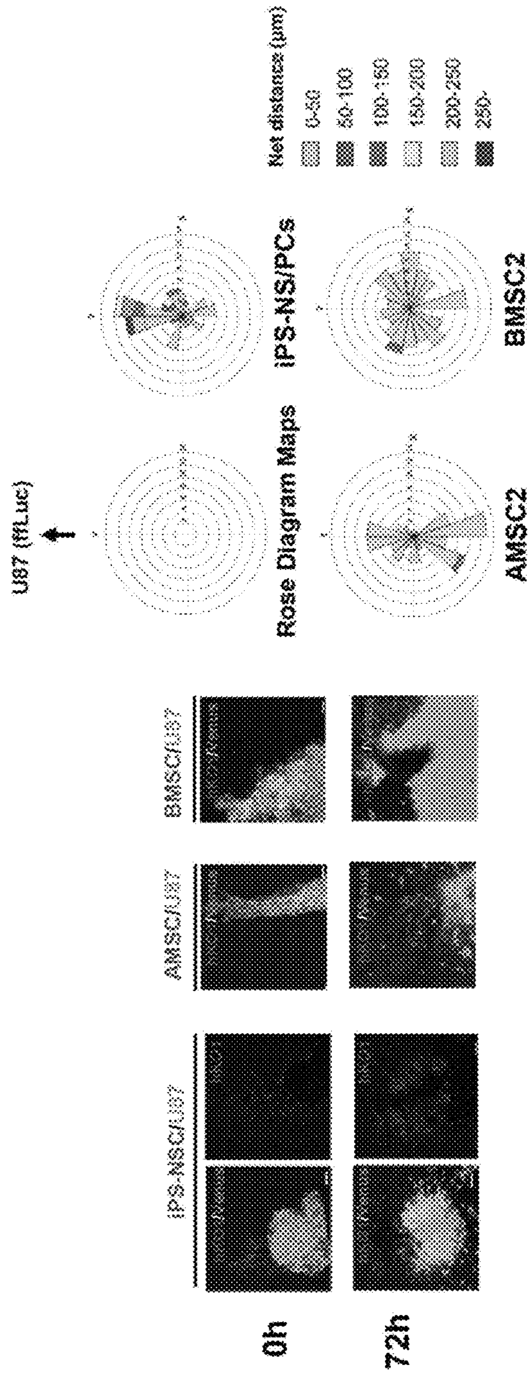
FIG. 2A shows the migratory property of therapeutic NSCs (yeast cytosine deaminase (yCD)-NSCs) towards malignant glioma.
Figure 2B:
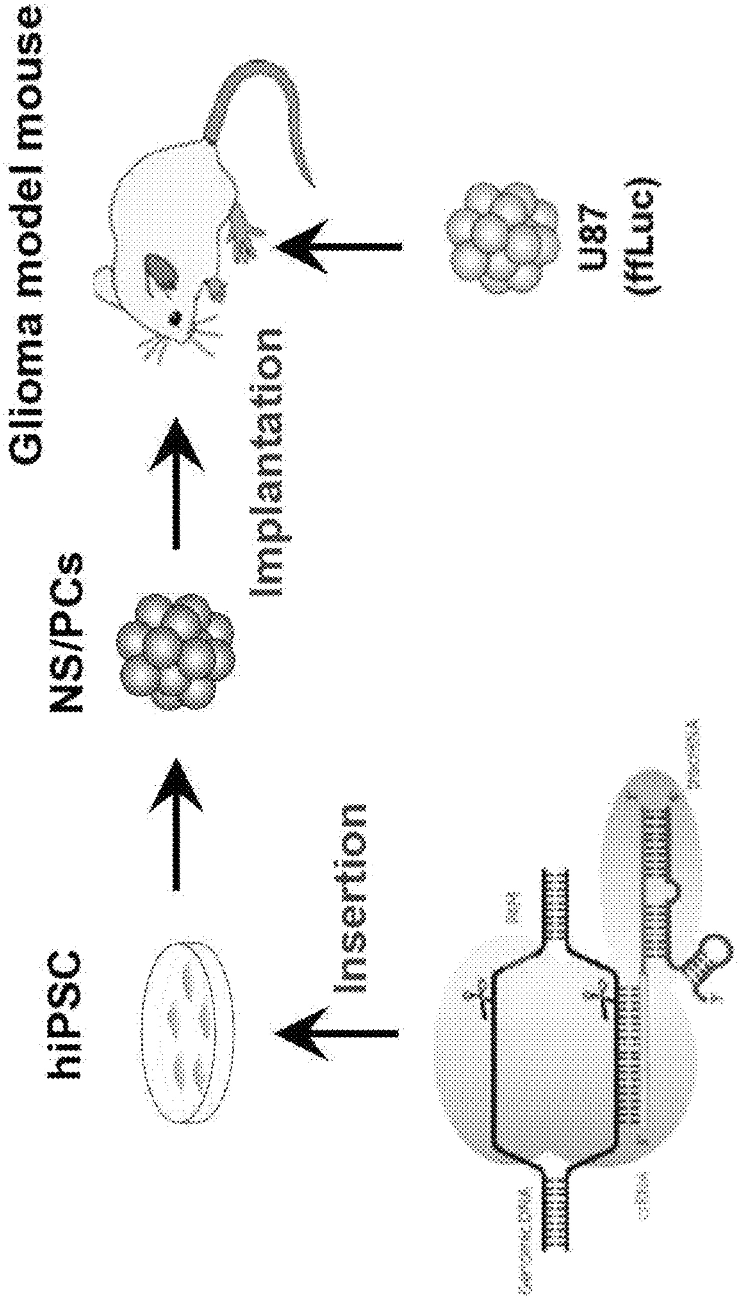
FIG. 2B shows the antitumor effect of therapeutic NSCs (yCD-NSCs) in a malignant glioma mouse model (1).
Figure 2C:
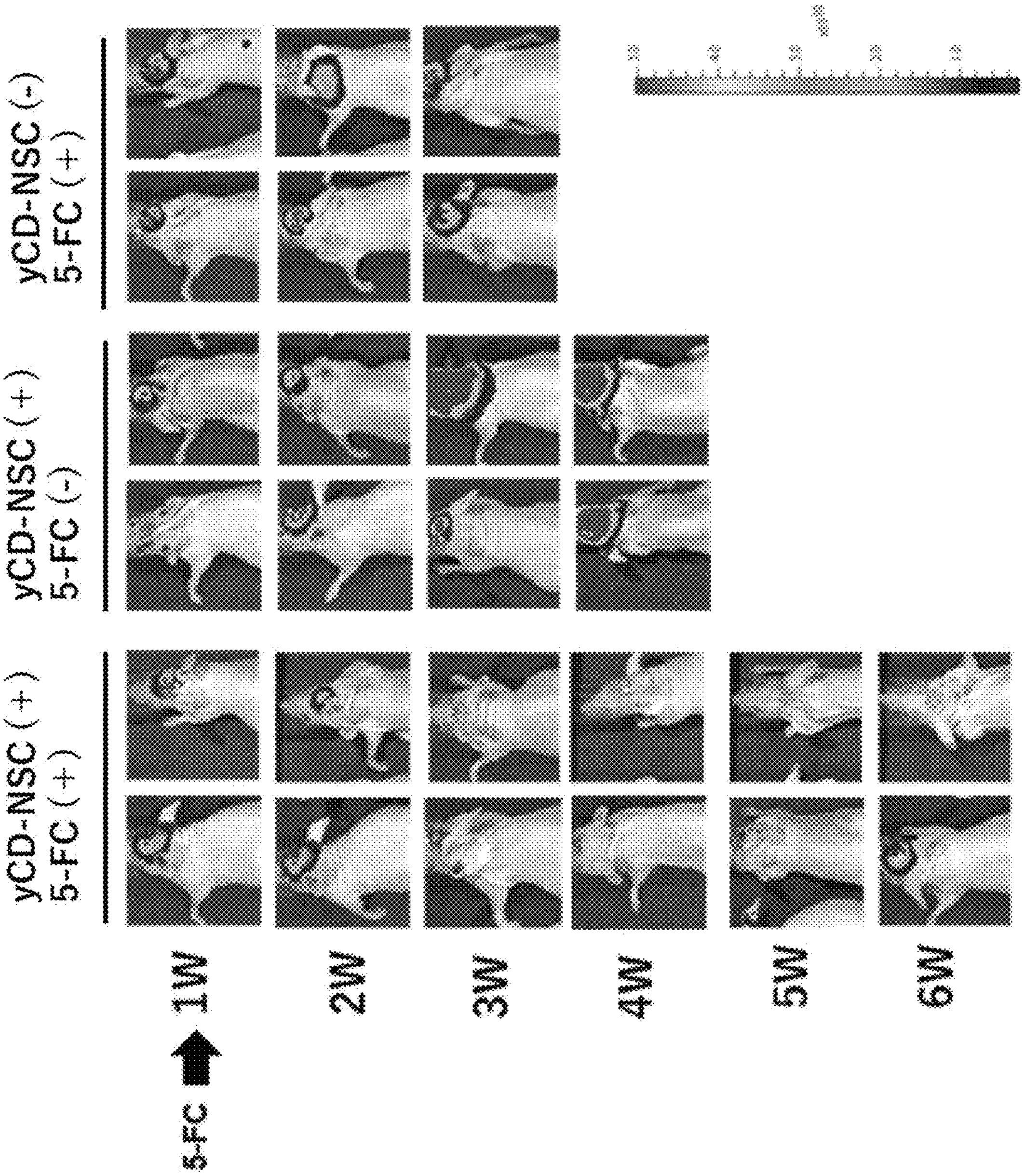
FIG. 2C shows the antitumor effect of therapeutic NSCs (yCD-NSCs) in a malignant glioma mouse model (2).

The present inventors imaged the NSCs derived from iPS cells migrating towards tumor in real time and established a unique method for assessing the anisotropic property quantitatively (see the Rose diagram map in FIG. 2A). The results showed that the iPS cells-derived NSCs had better anisotropic and migratory properties in the brain than those of other adipose-derived mesenchymal stem cells (AMSCs) and bone marrow-derived mesenchymal stem cells (BMSCs), which had been used as cell transplantation therapies, and also showed usefulness as a cellular delivery vehicle (FIG. 2A). The therapeutic NSCs (yCD-NSCs) established by the method shown in FIG. 1 were transplanted into a glioma mouse model (U87) (FIG. 2B). This is treatment utilizing the migratory property towards tumor. The results showed higher therapeutic effects due to administration of 5-FC compared with the controls (FIG. 2C). Two control groups were prepared: a group in which yCD-NSCs were transplanted, but 5-FC was not administered; and a group in which yCD-NSCs were not transplanted, but 5-FC was administered.

Figure 2D:
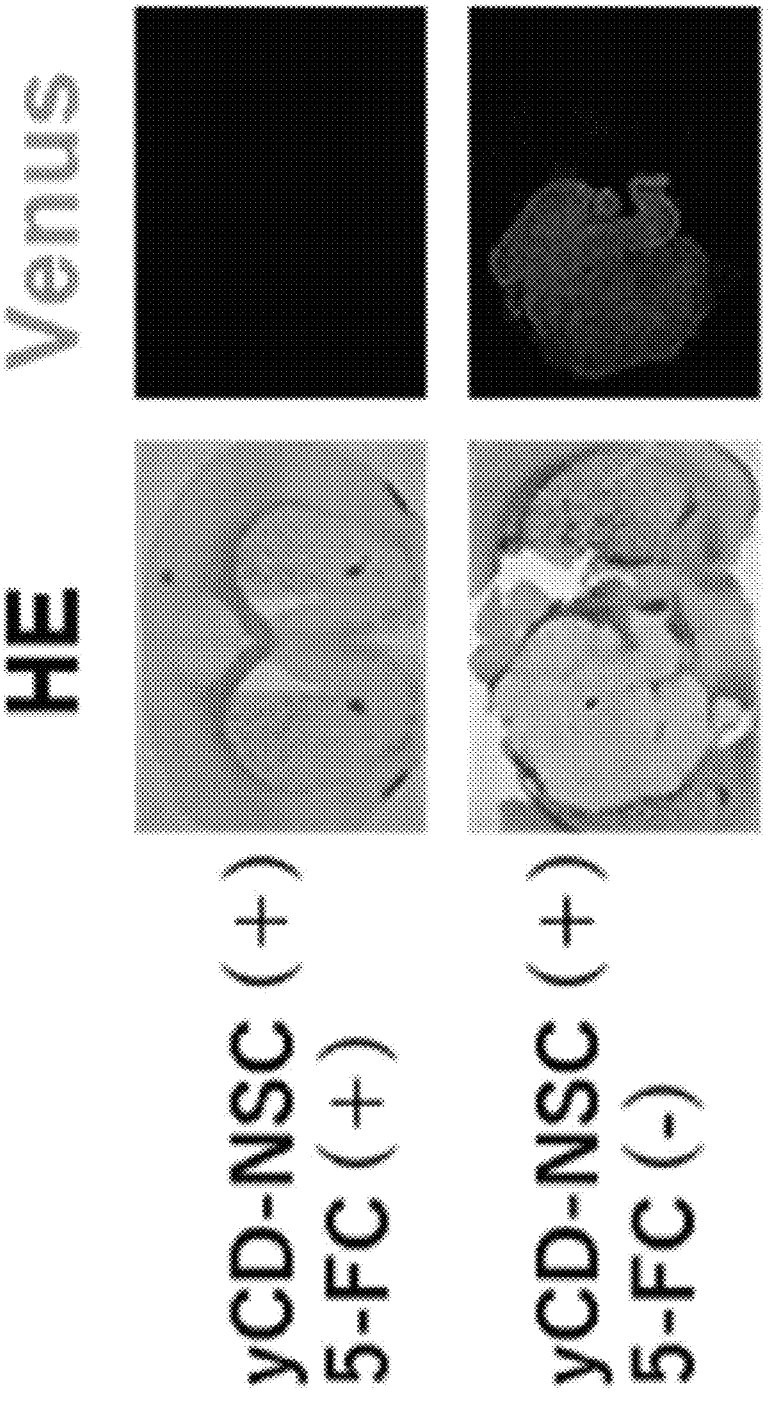
FIG. 2D shows the antitumor effect of therapeutic NSCs (yCD-NSCs) in a malignant glioma mouse model (3).
Figure 2E:
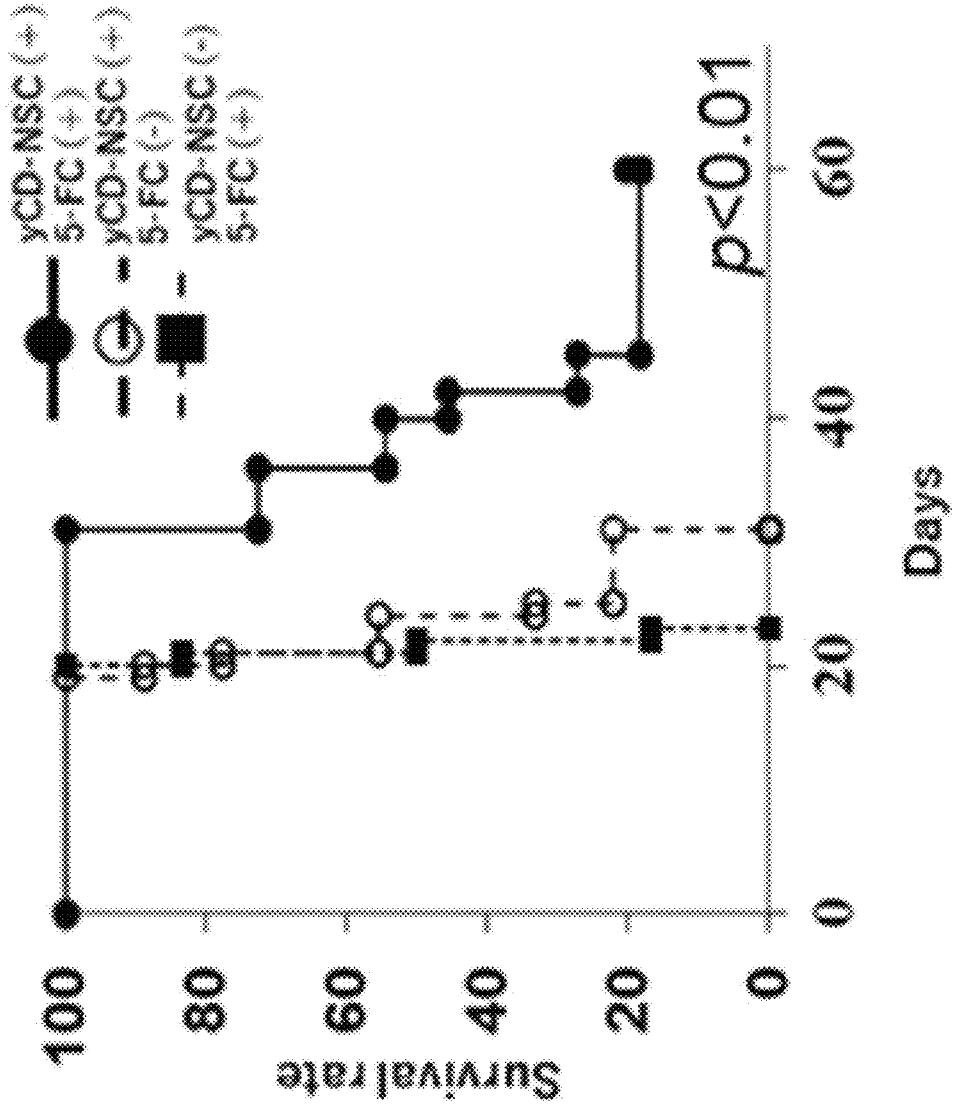
FIG. 2E shows the antitumor effect of therapeutic NSCs (yCD-NSCs) in a malignant glioma mouse model (4).

When brain tissues were assessed at 2 weeks after administration of 5-FC, marked tumor reduction and complete loss were observed compared with the controls (FIG. 2D). Tumors were labelled with a yellow Venus fluorescence protein. The survival time was markedly prolonged compared with both control groups (FIG. 2E).

<Brain Protecting Effect of Therapeutic NSCs (yCD-NSCs) Against Cerebral Contusion>

Figure 3A:
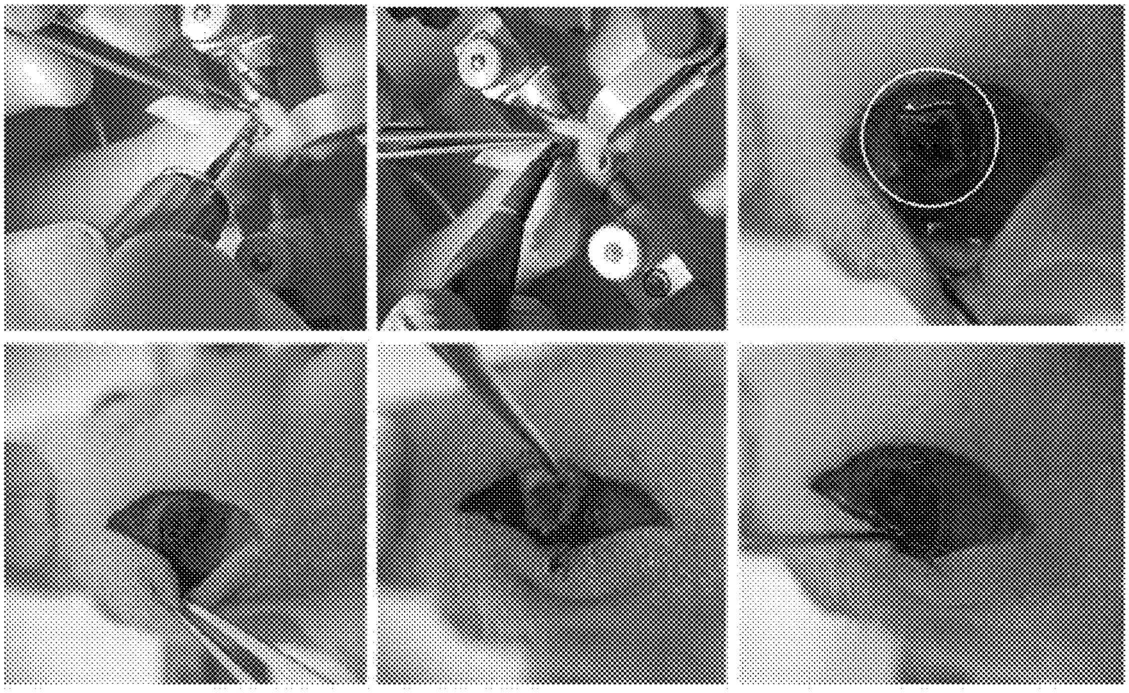
FIG. 3A shows the brain protecting effect of therapeutic NSCs (yCD-NSCs) against cerebral contusion (1).
Figure 3B:
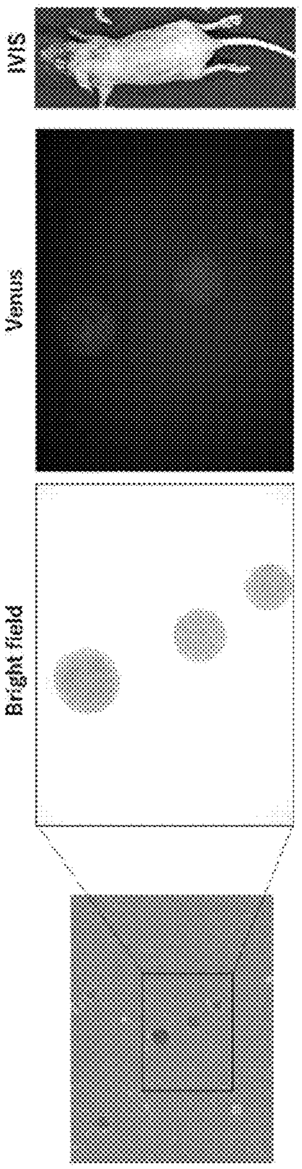
FIG. 3B shows the brain protecting effect of therapeutic NSCs (yCD-NSCs) against cerebral contusion (2).
Figure 3C:
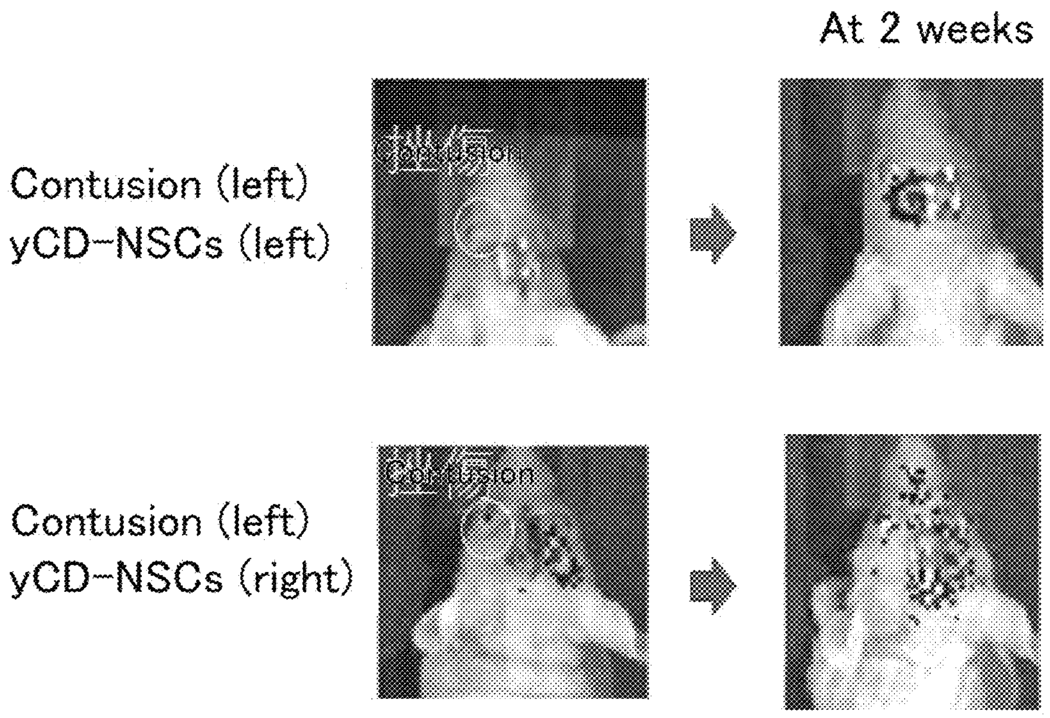
FIG. 3C shows the brain protecting effect of therapeutic NSCs (yCD-NSCs) against cerebral contusion (3).
Figure 3D:
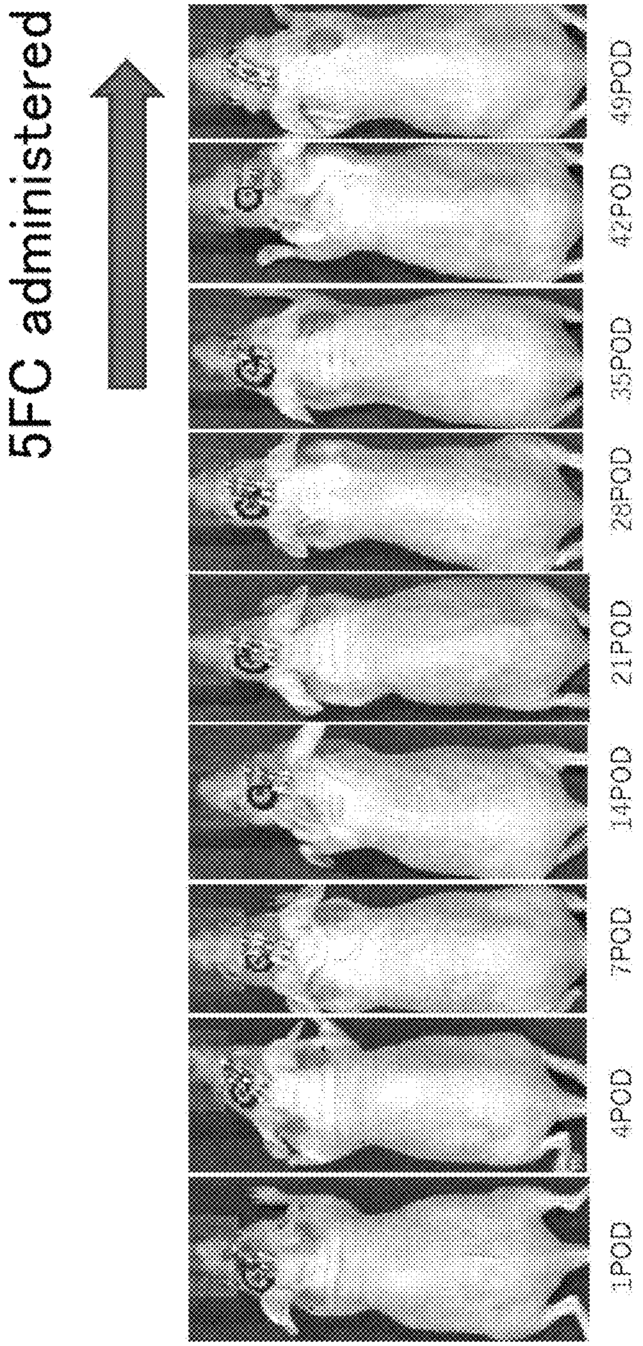
FIG. 3D shows the brain protecting effect of therapeutic NSCs (yCD-NSCs) against cerebral contusion (4).

The present inventors have reported establishment of a cerebral contusion model using a cooling system. A model with paresis of a right lower limb can be stably prepared by creating cerebral contusion in the left forebrain (FIG. 3A). yCD-NSCs were infected with the ffLuc (fusion gene of Venus fluorescence protein and Luc2 firefly luciferase) expression lentiviral vector, so that transplanted yCD-NSCs can be identified by using the IVIS (FIG. 3B). The glioma cell line was infected to assess the therapeutic effects in the method shown in FIG. 2. yCD-NSCs showed a marked migratory ability not only towards tumor cells but also the brain damage (cerebral contusion). yCD-NSCs transplanted contralaterally to cerebral contusion started showing signals thereof at the cerebral contusion site in less than 2 weeks (FIG. 3C).

yCD-NSCs were transplanted into the cerebral contusion site, engraftment was observed by using the IVIS, and 5-FC was administered at 35 days. As a result, the signals of yCD-NSCs completely disappeared (FIG. 3D). Tumorigenesis of transplanted cells is always mentioned as a problem in cellular therapies. However, since yCD-NSCs established by the present inventors are killed by administering 5-FC, which means that therapies have a safety mechanism against tumorigenesis, safe regenerative medicine can be realized.

Figure 3E:
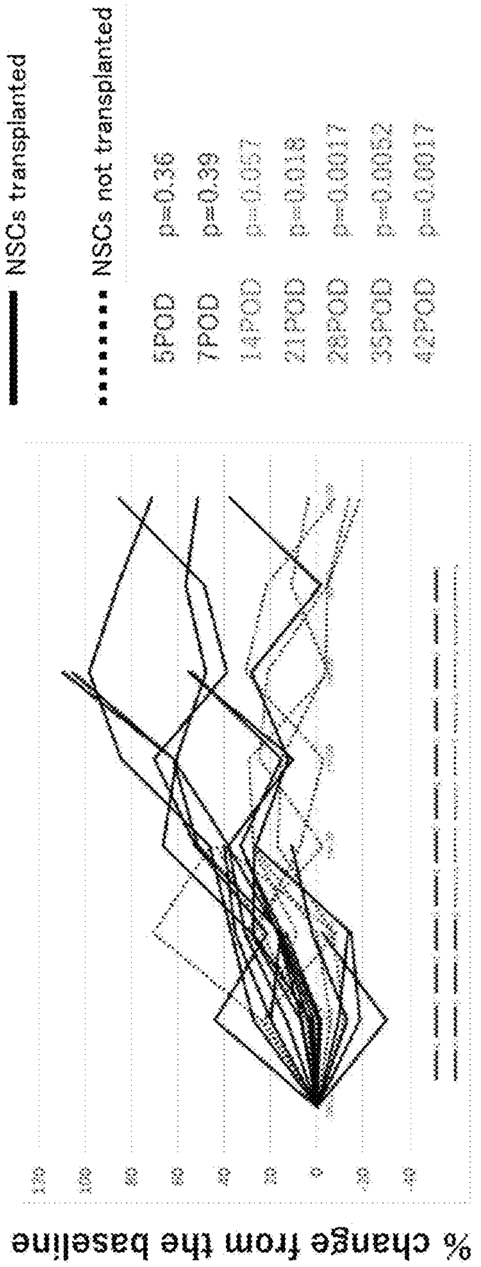
FIG. 3E shows the brain protecting effect of therapeutic NSCs (yCD-NSCs) against cerebral contusion (5).
Figure 3F:
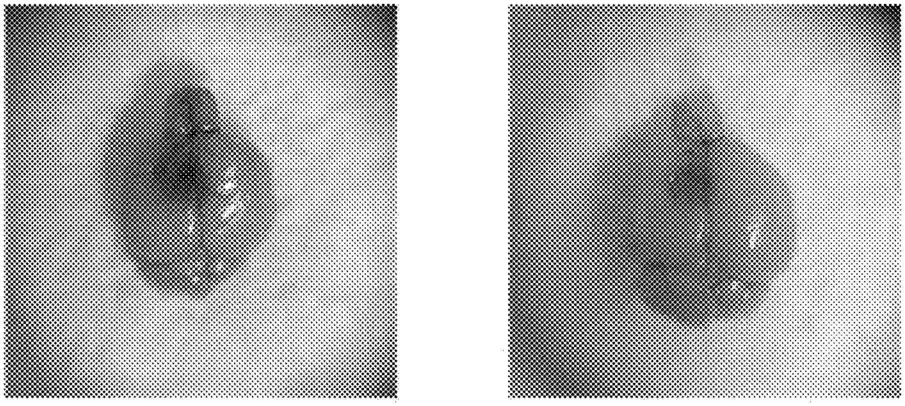
FIG. 3F shows the brain protecting effect of therapeutic NSCs (yCD-NSCs) against cerebral contusion (6).
Figure 3G:
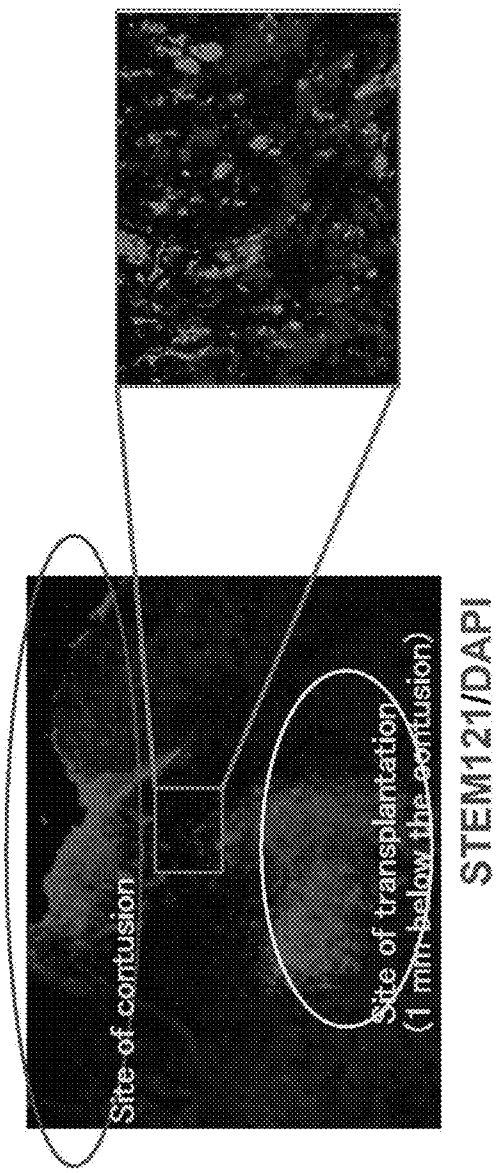
FIG. 3G shows the brain protecting effect of therapeutic NSCs (yCD-NSCs) against cerebral contusion (7).

Compared with the control groups, the motor function (grip strength) was significantly improved after cerebral contusion in the treatment group into which yCD-NSCs were transplanted (FIG. 3E). Additionally, the brain damage site was visualized using a dye (Evans blue), and marked reduction of the brain damage site was observed in tissues of the brain into which yCD-NSCs were transplanted at 14 days after cerebral contusion (FIG. 3F). This means that yCD-NSCs has a brain protecting effect against brain damage in the acute phase. Furthermore, when brain tissues were assessed at 42 days after yCD-NSCs were transplanted into a spot 1 mm below contusion, marked migration and accumulation were observed at the contusion site (FIG. 3G).

<Effect of Released 5-FU on Motor Function>

Figure 4A:
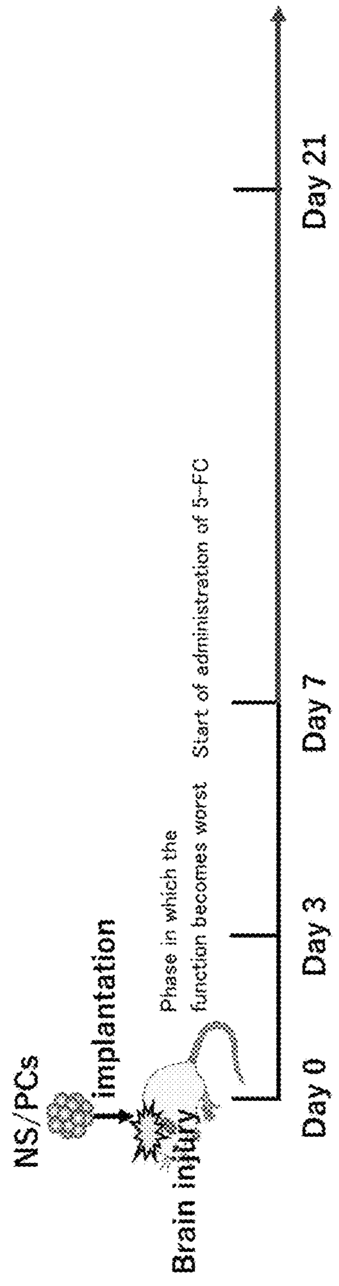
FIG. 4A shows the effect of released 5-FU on motor function (1).
Figure 4B:
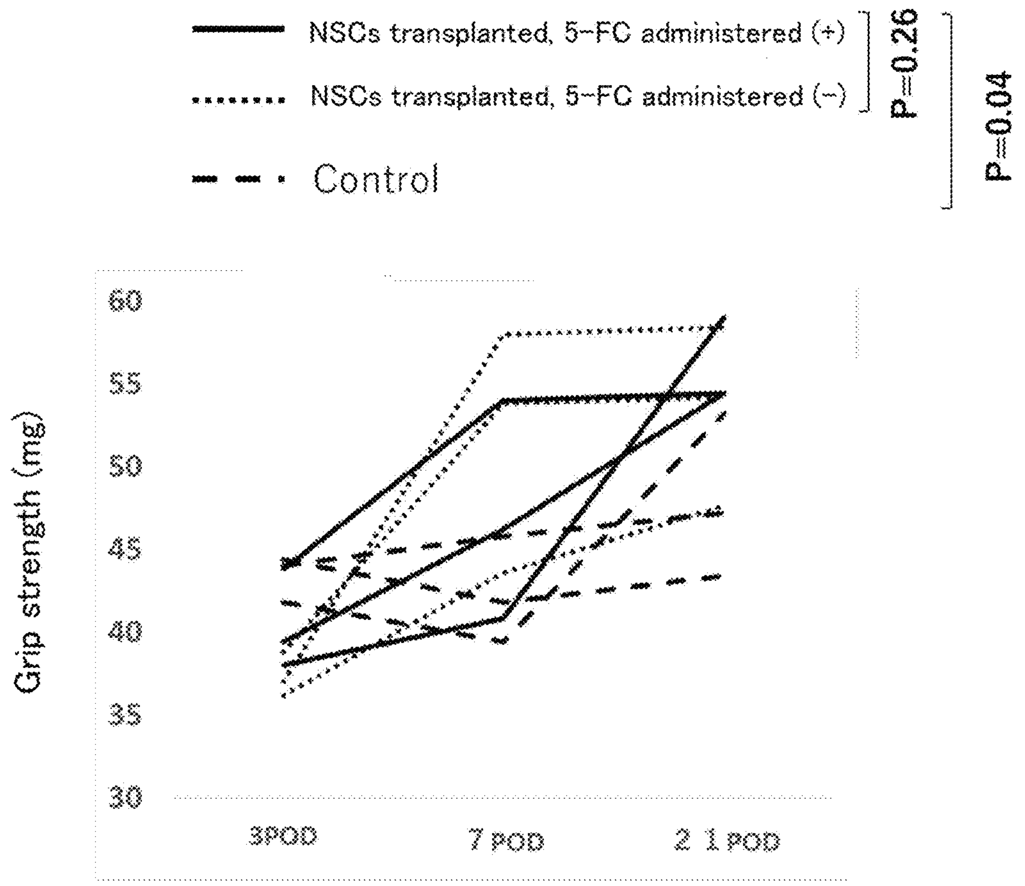
FIG. 4B shows the effect of released 5-FU on motor function (2).

The present inventors investigated whether brain functions were reduced or not when NSCs that had exhibited a brain protecting effect in the acute phase and remained in an undifferentiated form (having a risk of tumorigenesis) were killed by administering 5-FC. NSCs were transplanted in the hyperacute phase on the contusion creation day (Day 0), the brain protecting effect was allowed to be exhibited in the acute phase up to Day 7, and then 5-FC was administered for 2 weeks into the subacute phase (FIG. 4A). As a result, even when 5-FC was administered from day 7, the motor function was not reduced, and functional recovery was achieved as seen in the group untreated with 5-FC (FIG. 4B). Furthermore, the function significantly improved compared with the controls in which NSCs were not transplanted (FIG. 4B).

<Safety of Therapeutic NSCs (yCD-NSCs) (Differentiated Cells)>

Figure 5A:
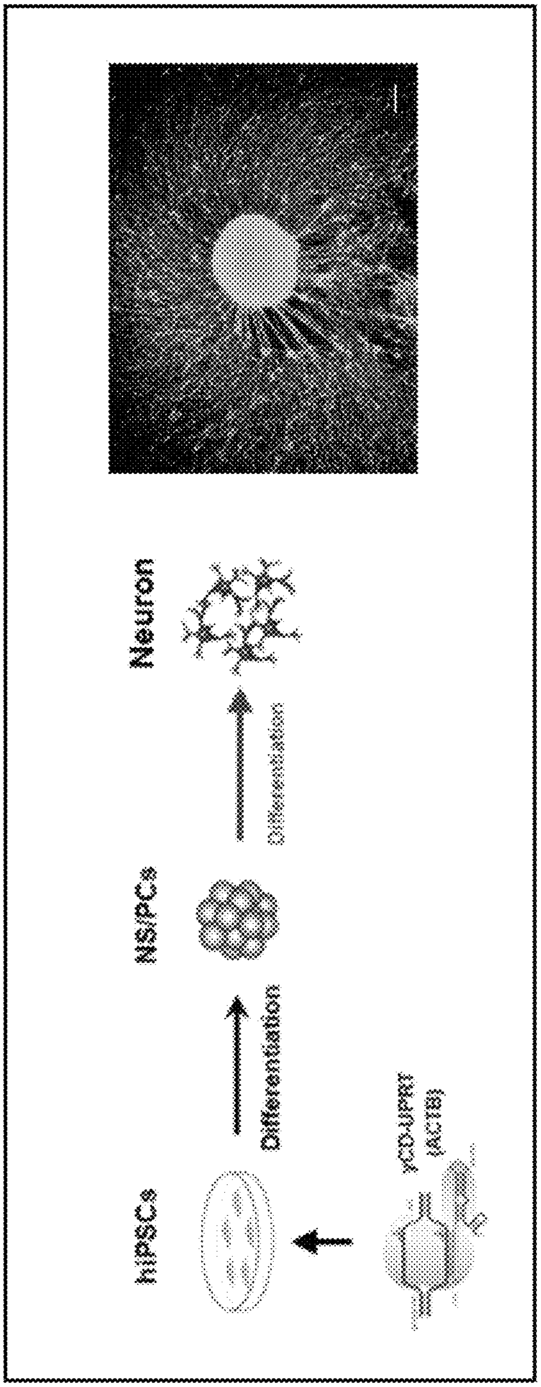
FIG. 5A shows the safety of therapeutic NSCs (yCD-NSCs) (differentiated cells) (1).
Figure 5B:
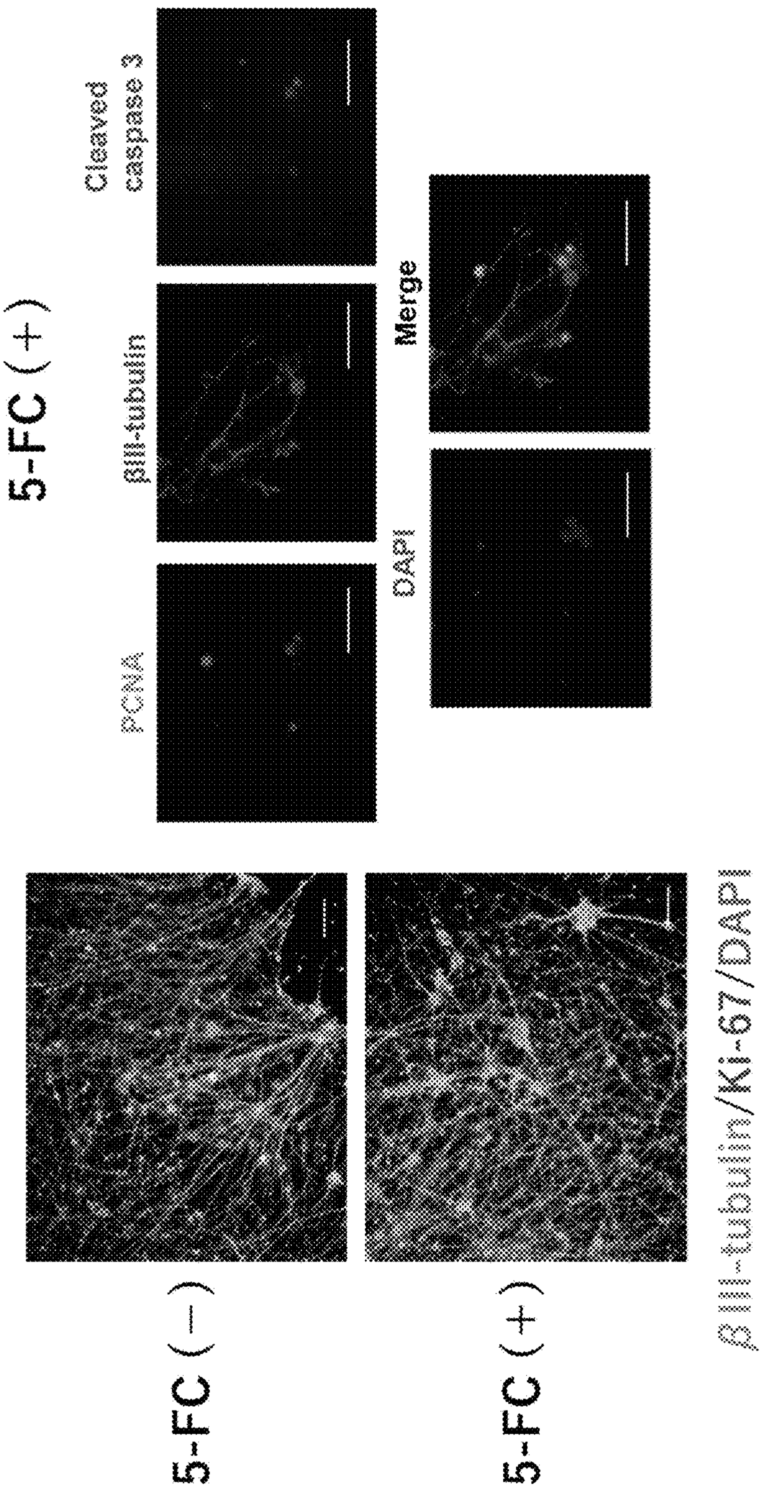
FIG. 5B shows the safety of therapeutic NSCs (yCD-NSCs) (differentiated cells) (2).

To show an evidence that differentiated cells are not affected by yCD-NSCs, an experiment was performed in which yCD-NSCs themselves were differentiated into neurons in vitro, and prodrug 5-FC was administered (FIG. 5A). It was expected that neurosphere would always show morphological differentiation into neurons with a very long projection. Cells with such a long extended projection were positive for βIII tubulin, a neuron marker (FIG. 5B). Thus, differentiation into neurons was shown. However, some Ki-67-positive proliferative cells still remained (FIG. 5B). It was shown that, when 5-FC was administered, only these Ki-67-positive proliferative cells were killed, and differentiated cells positive for βIII tubulin were not killed by the released 5-FU. It is shown that proliferative cells positive for PCNA were killed, and differentiated cells positive for βIII tubulin were not killed (FIG. 5B).

Figure 5C:
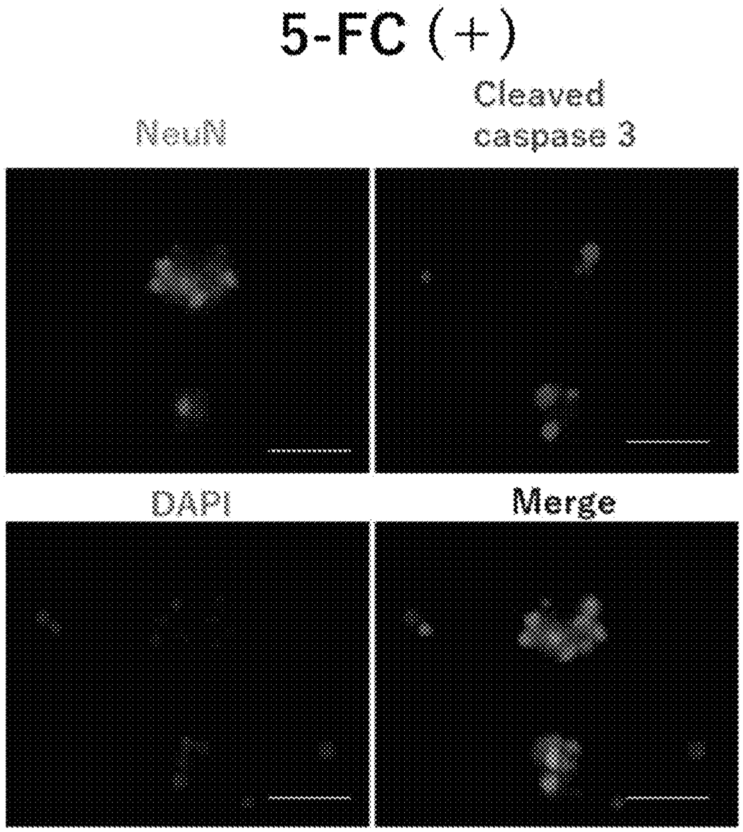
FIG. 5C shows the safety of therapeutic NSCs (yCD-NSCs) (differentiated cells) (3).

Additionally, it was clearly shown that there were some cells in which NeuN, a marker for mature neurons, was expressed, and such cells were not killed by 5-FU released after administration of 5-FC (FIG. 5C).

Figure 6A:
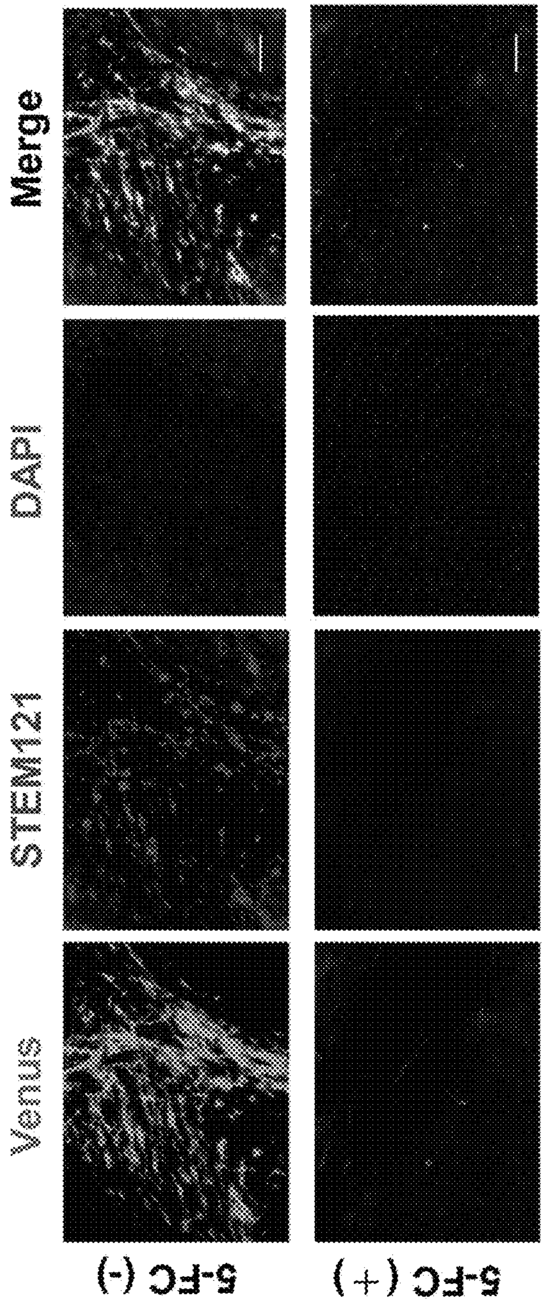
FIG. 6A shows the safety of therapeutic NSCs (yCD-NSCs) (mouse model) (1).

<Safety of Therapeutic NSCs (yCD-NSCs) (Mouse Model)> yCD-NSCs transplanted into a glioma stem cell hG008 mouse model migrated towards tumor cells and existed in the tumor. While yCD-NSCs killed tumor cells, they were also killed and did not remain after 5-FC was administered (FIG. 6A).

Figure 6B:
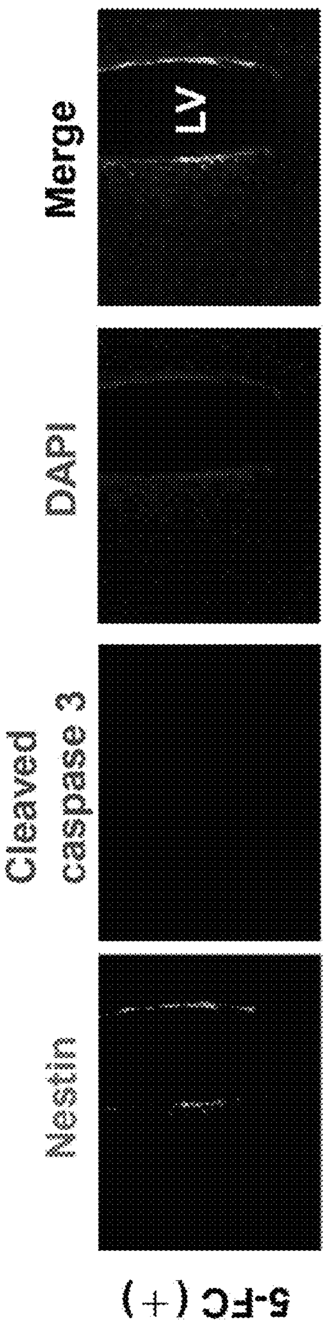
FIG. 6B shows the safety of therapeutic NSCs (yCD-NSCs) (mouse model) (2).
Figure 6C:
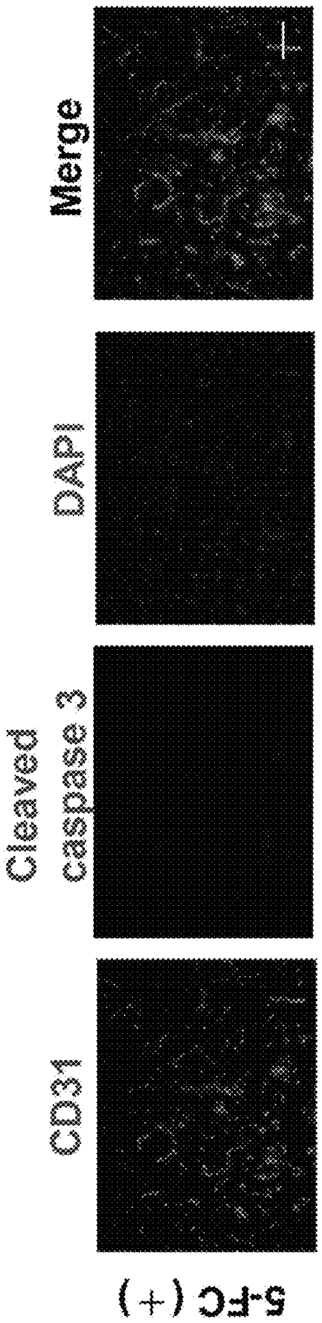
FIG. 6C shows the safety of therapeutic NSCs (yCD-NSCs) (mouse model) (3).
Figure 6D:
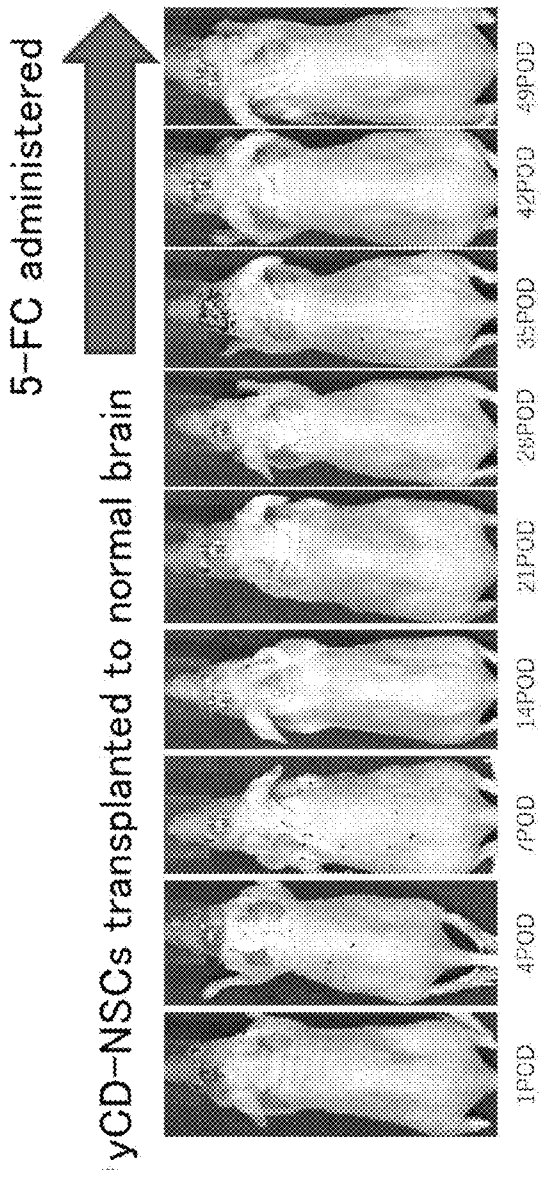
FIG. 6D shows the safety of therapeutic NSCs (yCD-NSCs) (mouse model) (4).
Figure 6E:
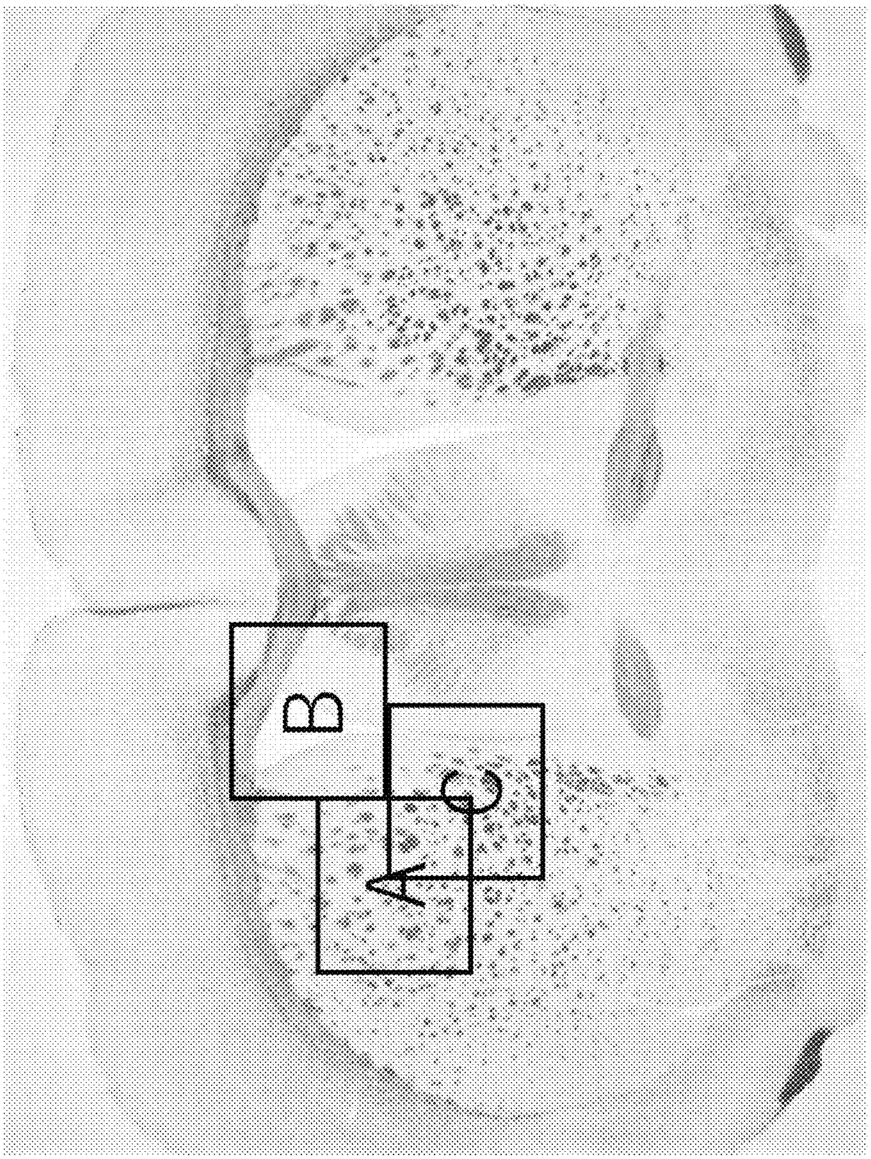
FIG. 6E shows the safety of therapeutic NSCs (yCD-NSCs) (mouse model) (5).

It is considered, in theory, that 5-FC does not affect cells in the brain occupied by terminally differentiated cells, but may affect neural precursor cells existing in the vicinity of the cerebral ventricle and slightly divided cells in the vascular endothelium and the like. Accordingly, in this experiment, yCD-NSCs were transplanted into the normal brain, and 5-FC was administered. As a result, no clear apoptosis was observed in cells among neural precursor cells at the cerebral ventricle wall (FIG. 6B) or vascular endothelial cells (FIG. 6C) in the vicinity of the transplantation site. It is indicated that yCD-NSCs do not show an anisotropic property particularly for the vicinity of these tissues since they are accumulated in the tumor or damaged brain. The time course after yCD-NSCs were transplanted into the normal brain was observed using the IVIS. The signals disappeared after administration of 5-FC, indicating their own death (FIG. 6D). A, B, and C in the brain tissue image of FIG. 6E correspond to the fluorescence tissue image at sites in FIGS. 6A, 6B and 6C.

<Biomarkers for Antitumor Effects of yCD-NSCs>

Figure 7A:
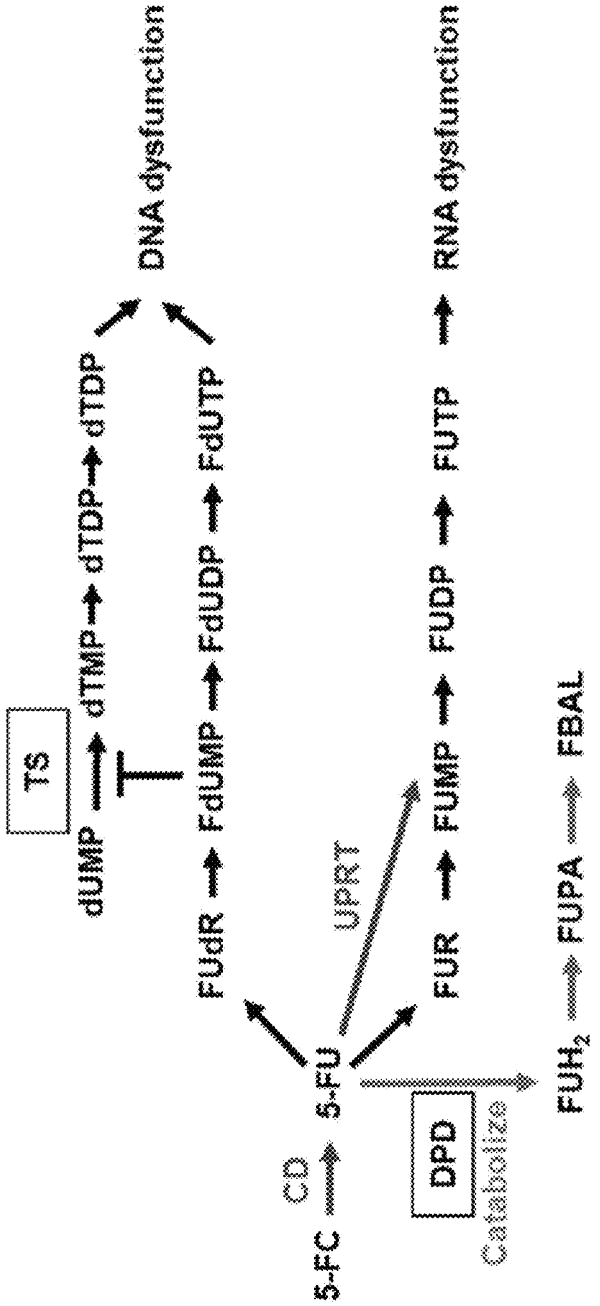
FIG. 7A shows biomarkers for the antitumor effect of yCD-NSCs (1).
Figure 7B:
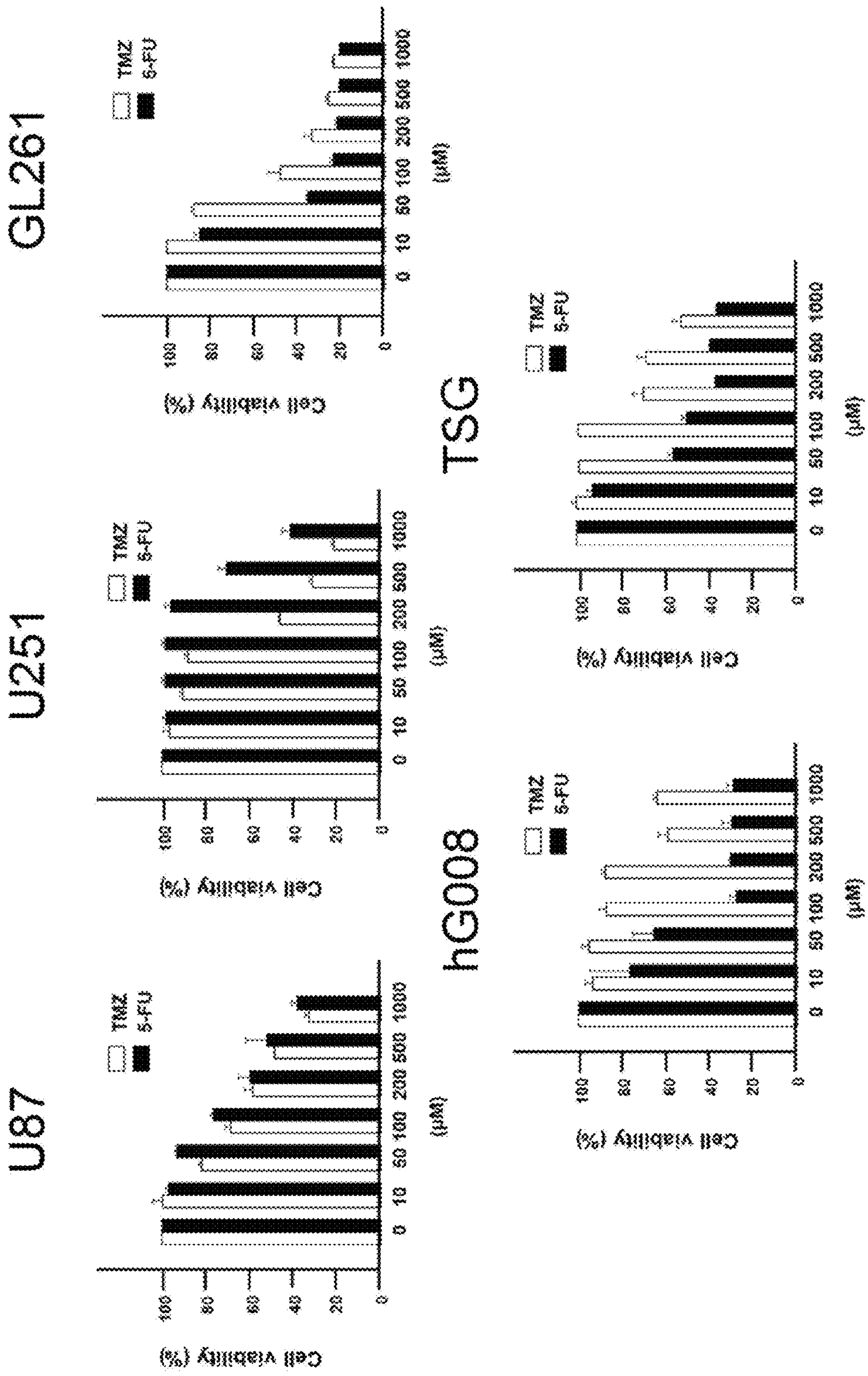
FIG. 7B shows biomarkers for the antitumor effect of yCD-NSCs (2).

FdUMP, an active metabolite of 5-FU, inhibits the enzymatic activity of thymidylate synthase (TS), which is a de novo-designed enzyme for DNA (FIG. 7A). Thus, the de novo synthesis system of DNA is inhibited, and DNA damage occurs time-dependently. Additionally, 5-FU taken up in the tumor is usually degraded with a degrading enzyme dihydropyrimidine dehydrogenase (DPD) (FIG. 7A). Therefore, it is expected that, when the DPD activity is lower, the concentration of 5-FU in the tumor becomes higher, and when the TS activity of the target enzyme is lower, the TS activity is more efficiently inhibited by FdUMP, enhancing the antitumor effects. It was therefore considered that the expressions of TS and DPD would serve as biomarkers for the antitumor effects of yCD-NSCs of the present inventors. The susceptibility of each glioma cell line to 5-FU was assessed by CCK-8 assay. The results showed that the susceptibility was (favorable) GL261, TSG, hG008, U87 and U251 (unfavorable) (FIG. 7B).

Figure 7C:
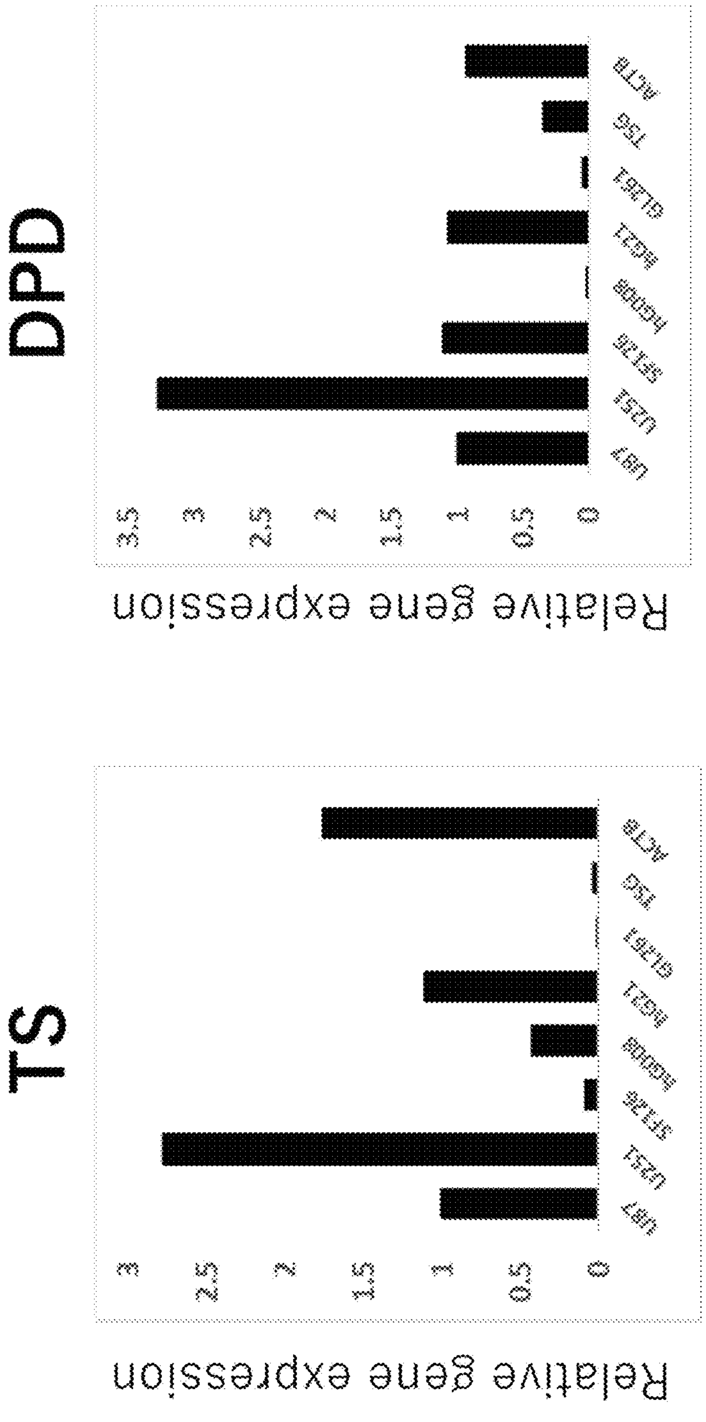
FIG. 7C shows biomarkers for the antitumor effect of yCD-NSCs (3).
Figure 7D:
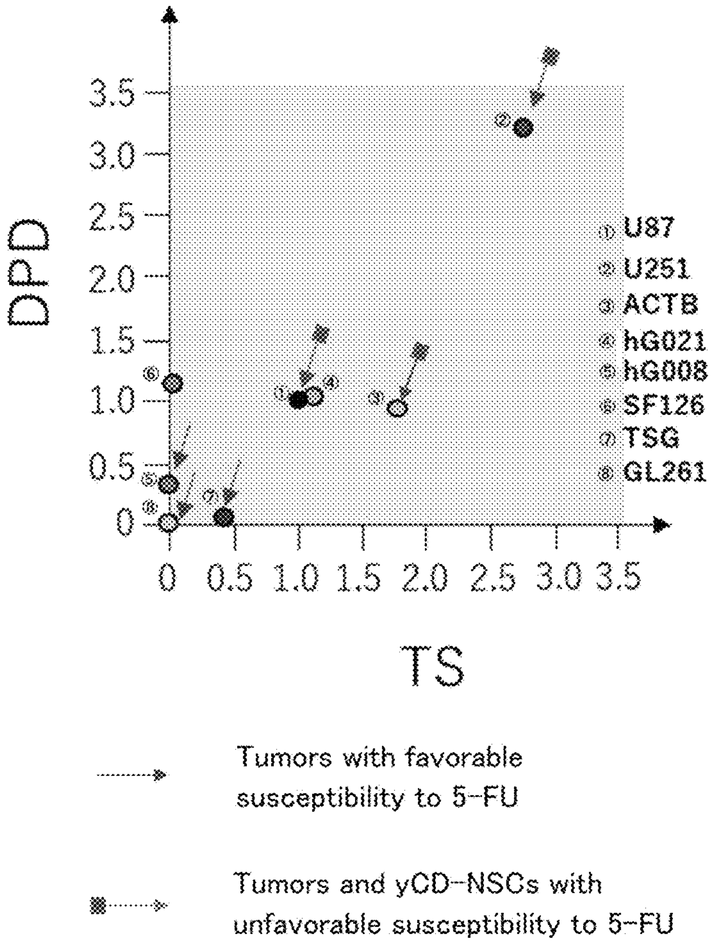
FIG. 7D shows biomarkers for the antitumor effect of yCD-NSCs (4).

The gene expressions of TS and DPD at the mRNA level were analyzed quantitatively by RT-qPCR. In U251, the expression levels of both TS and DPD were found to be high (FIG. 7C). Similar results were obtained by western blotting. A graph plotting in FIG. 7C shows that the relative gene expressions of both enzymes in hG008, TSG, and GL261 showing marked effect on 5-FU were 0.5 or lower (assessed assuming the expression in U87 as 1). Additionally, the relative gene expressions of both enzymes in U251, which was the most resistant to 5-FU, were approximately 3.0 (FIG. 7D). From these results, TS and DPD could be biomarkers for this treatment. Additionally, ACTB (yCD-NSCs) had a particularly high TS activity, and the response to 5-FU was not favorable (FIG. 7D). Specifically, determination of a suicide gene insertion site which has a favorable susceptibility to 5-FC is required all the more, and the ACTB region assessed by the present inventors is applicable. Additionally, the not favorable susceptibility of NSCs to 5-FU also means a result indicating "safety," in which endogenous neural stem cells are less affected.

Example 2

<Background>

Since neural stem cells (NSCs) and mesenchymal stem cells (MSCs) have a property of migrating towards a tumor or damage site, they have been used as cellular delivery vehicles (CDV) of therapeutic genes (References 1 and 2). NSCs can be collected from fetus-derived tissues and the like, use thereof is not easy because of problems of the low proliferative ability thereof and ethical aspects. The present inventors solved these problems by inducing differentiation of human induced pluripotent stem cells (iPS cells) into NSCs. Additionally, the present inventors have been studying a treatment strategy using NSCs as a CDV of a therapeutic gene for glioblastoma (cytosine deaminase-uracil phosphoribosyl transferase: CD-UPRT). Meanwhile, which of NSCs and MSCs can be an excellent CDV for glioblastoma is not clearly answered.

The present inventors assessed the migratory property of NSCs and MSCs (derived from adipose tissue and bone marrow) transplanted into the brain towards glioblastoma cells using brain section culture (Tamura R. Mol Brain. 2019 [Japanese Patent Application No. 2019-052704]). The results showed that NSCs exhibited significantly favorable migratory and anisotropic properties for MSCs. Accordingly, in this example, a key molecule that makes differences between migrations of NSCs and MSCs was identified by performing RNA-Seq analysis for the NSC line, the MSC line, and the glioblastoma cell line possessed by the present inventors.

<Method>

Glioma stem cells (GSCs) have been reported to make malignant neuroglioma refractory. Unlike Glioma cells (GCs), GSCs have a self-replicating ability and a tumorigenic potential as well as highly infiltrative property and high resistance to chemotherapy and radiotherapy, which are considered to cause recurrence.

RNAs were extracted from human iPS cell-derived NSCs (iPSC-NSCs), human fetal cortex-derived NSCs (FcNSCs), human fetal hippocampus-derived NSCs (FhNSCs), 2 human adipose tissue-derived MSC lines (AMSC1, AMSC2), 2 human bone marrow-derived MSC lines (BMSC1, BMSC2), human GC lines (U87, U251, SF126), and human GSC lines (hG008, hG021) (Reference 3) by the QIA cube automated system (QIAGEN) using miRNeasy Serum/Plasma Kit (QIAGEN). RNA-Seq analysis was outsourced to Macrogen Inc.

Additionally, the already reported RNA-Seq data of resected glioblastoma were collected using the database of NCBI Short Read Archive (SRR359290 and SRR359291) (Reference 4).

For differences in gene expressions, p=0.001 and 10-fold by log 2 fold-change ratio as a cutoff value were assumed by the Benjamini-Hochberg method using DESeq2 suite of bioinformatics tools.

Ligand-Receptor Pairing Analysis

Figure 8:
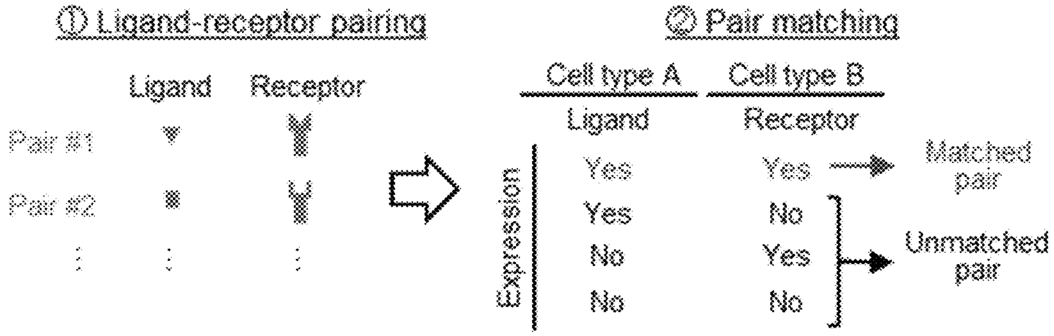
FIG. 8 shows the summary of a ligand-receptor pairing analysis.

Ligand-receptor pairing was performed using the previously reported database as reference (Reference 5). A total of 2552 ligand-receptor pairs were carefully selected (Reference 6), and when expressions of both ligand and receptor were found between certain cells, they were selected as matched pairs (see FIG. 8).

Single-Cell RNA-Seq

The previously reported single-cell RNA-Seq data of resected glioblastoma were re-examined (Reference 7).

<Results>

Figure 9:
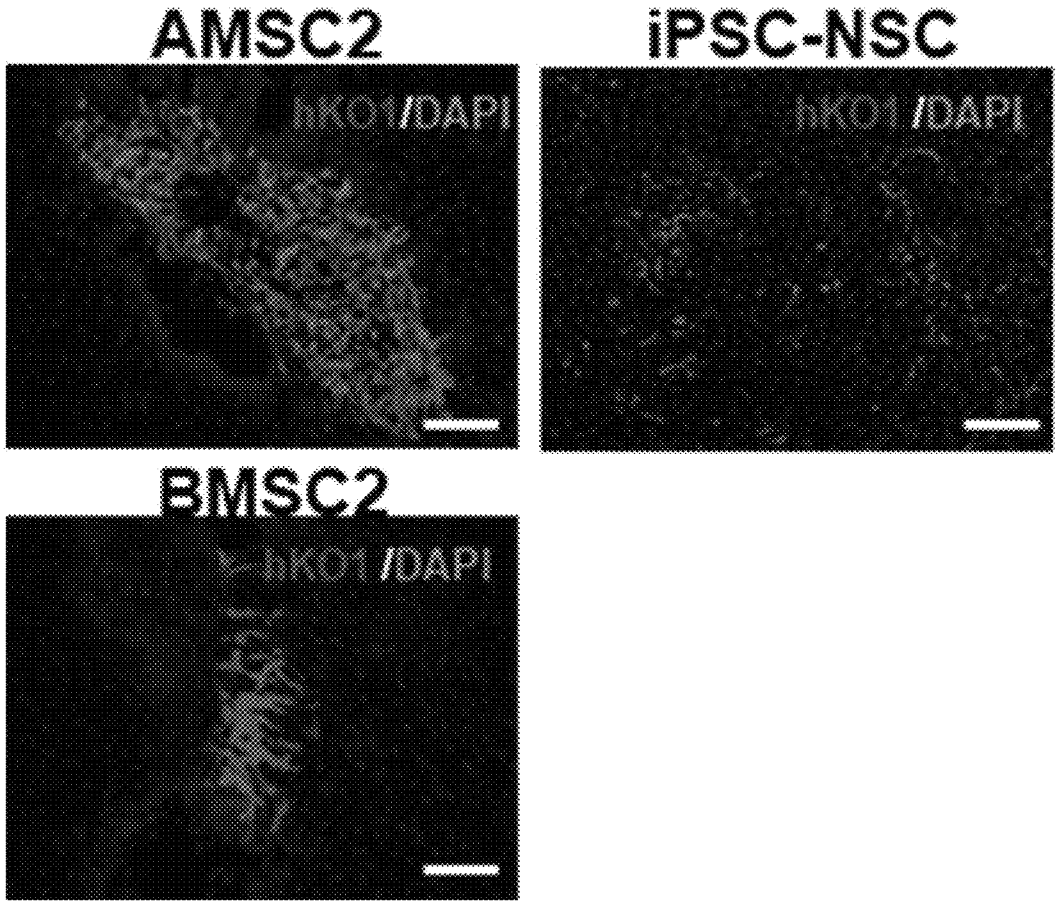
FIG. 9 shows photographs of neural stem cells (NSCs) and mesenchymal stem cells (MSCs) that were transplanted into the brain.
Figure 10:
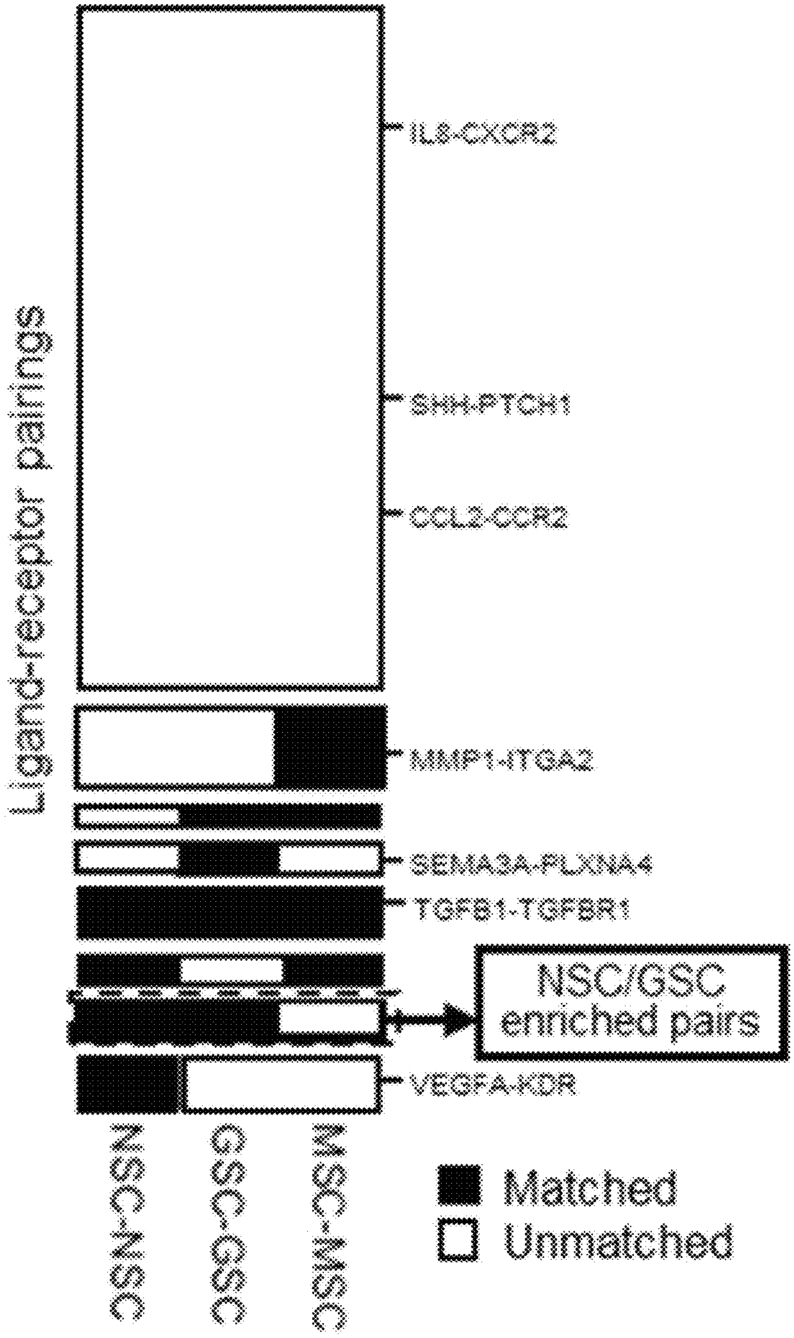
FIG. 10 is a heat map showing interactions between autocrine cells.
Figure 11:
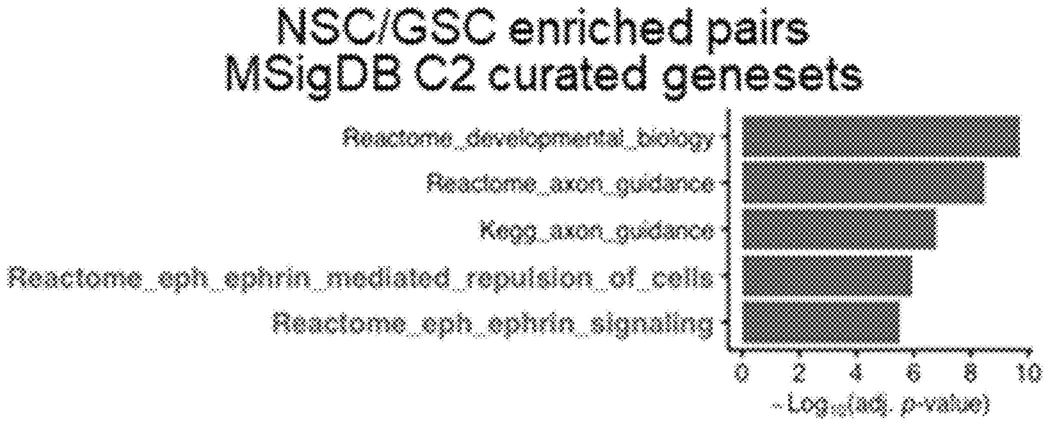
FIG. 11 shows NSC and GSC-specific autocrine ligand-receptor pairs indicated by an enrichment analysis.
Figure 12:
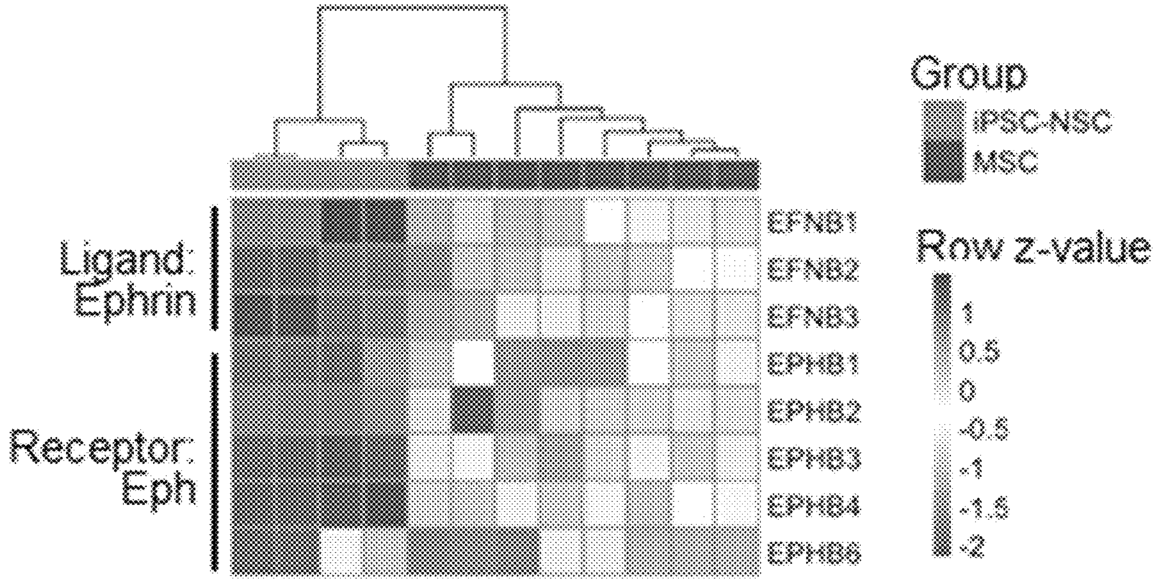
FIG. 12 shows a heat map showing the expressions of the EphB and ephrin B genes.
Figure 13:
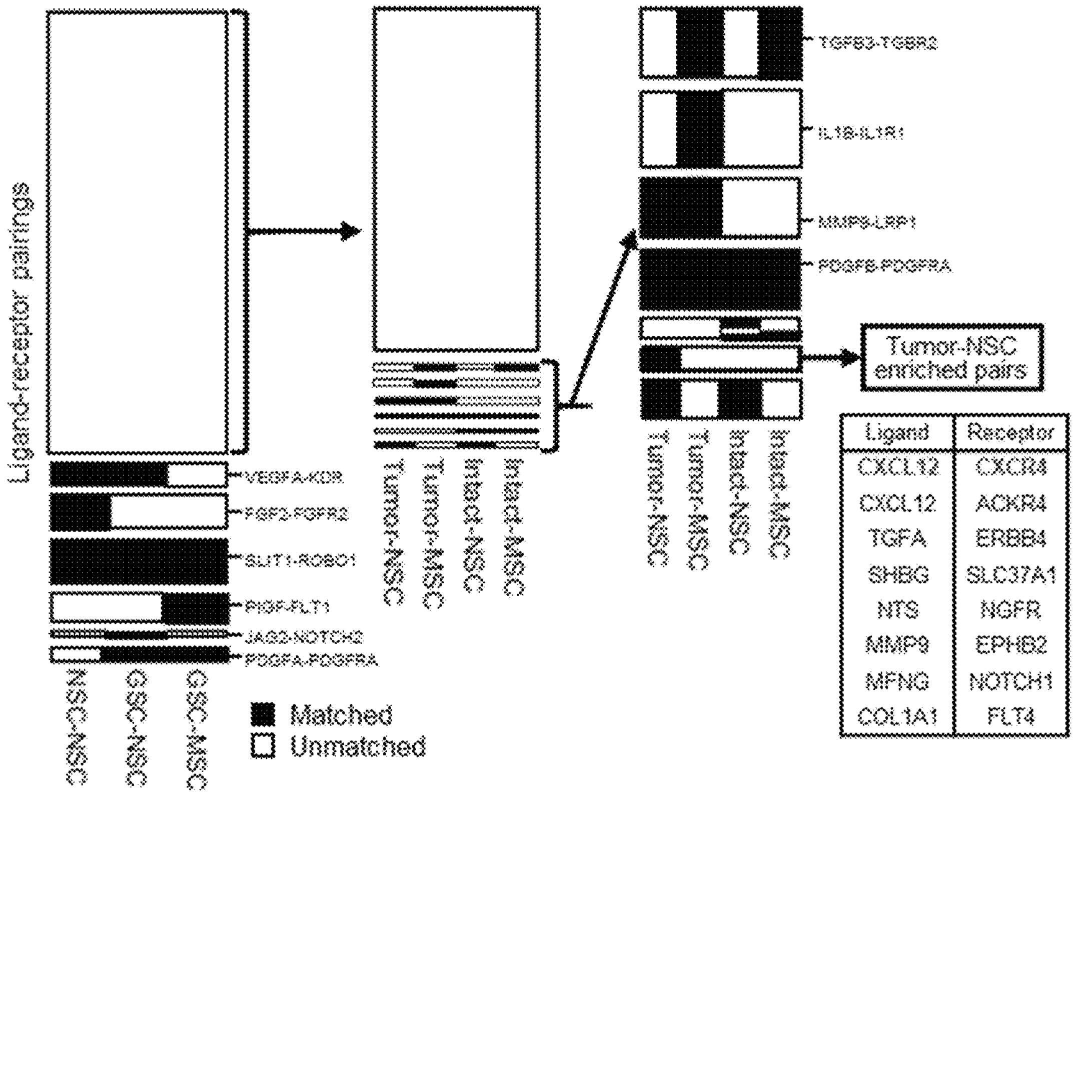
FIG. 13 shows a heat map showing interactions between paracrine cells.
Figure 14:
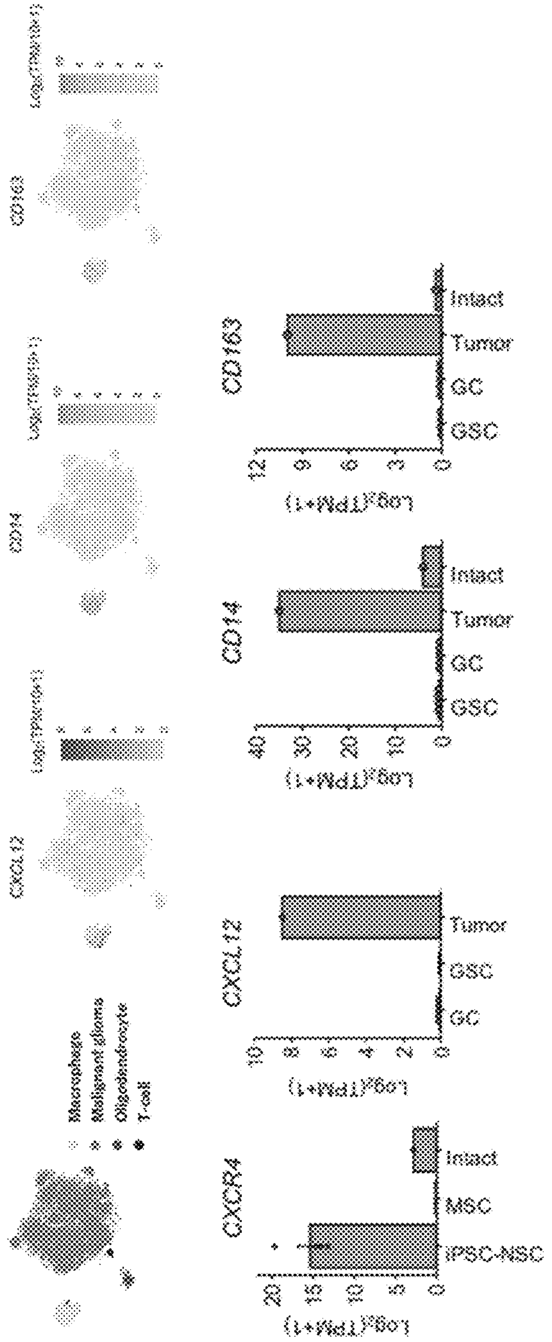
FIG. 14 shows the previously reported t-SNE plot using single-cell RNA-Seq (an analysis method that can analyze gene expressions of single cells comprehensively and visualize the similarity of cells on a two-dimensional plot) of resected glioblastoma.

First, autocrine interactions were assessed to extract the self-repulsion signaling pathway. The reason for paying attention to self-repulsion is that NSCs and MSCs show different behaviors in the brain without tumor when transplanted solely. NSCs are diffused when engrafted, and MSCs form a cell aggregate (FIG. 9). Furthermore, since occurrence of these engraftments is comparable to GSCs (diffused engraftment) and GCs (cell aggregate formation) [Tamura R. Mol Brain. 2019], differences between GSCs and GCs were considered as useful information. As a result, 92 ligand-receptor pairs were identified between NSC-NSC and between GSC-GSC (FIG. 10). These were not identified for MSCs.

An enrichment analysis (analysis to determine whether there is a correlation between a specific gene set and the expression ratio) indicated that these pairs were related to the Eph/ephrin repulsion signaling. In particular, EphB/ephrinB was upregulated in NSCs compared with MSCs. In fact, it has been reported that EphB/ephrinB is involved in infiltration of GSCs (Reference 8). Therefore, it was suggested that, in particular, EphB/ephrinB causes self-repulsion between NSCs and is involved in diffused engraftment.

Subsequently, paracrine signaling interactions between GSCs and NSCs or MSCs were assessed. Specifically, it was considered that a ligand was released by GSCs, that NSCs had a receptor which sensed it, and that this pair was involved in the anisotropic property. A total of 27 ligand-receptor pairs were identified between NSCs and GSCs. However, the expression levels of these pairs did not increase in the glioma cell line of the present inventors in vitro. This result suggested a possibility that GSCs cultured in vitro could not completely reflect glioblastoma in the brain. Accordingly, the present inventors performed an in silico ligand-receptor pairing analysis, using the previously reported RNA-Seq data of resected glioblastoma. The results showed 8 ligand-receptor pairs between the resected glioblastoma and NSCs. The present inventors paid attention to the CXCL12/CXCR4 signal, which has been reported frequently so far (Reference 2). CXCR4 was highly expressed in NSCs, but not expressed in MSCs. CXCL12 was expressed more highly in the resected glioblastoma than in GSCs cultured in vitro.

Additionally, the present inventors re-examined the previously reported RNA-Seq data of single-cells of glioblastoma. The results also showed high expression of CXCL12 in tumor-infiltrating macrophages known to be accumulated in the microenvironment surrounding the glioblastoma. The expression levels of macrophage markers, such as CD14 and CD163, were low in GSCs cultured in vitro. These data suggest that CXCL12 in intracerebral tumor-infiltrating macrophages can also be involved in the anisotropic property of NSCs expressing CXCR4 (not expressed in MSCs).

From the above, it was concluded that self-repulsion reactions by EphB-ephrinB and the anisotropic property by CXCL12-CXCR4 were involved, and both these factors induced migration with the anisotropic property of NSCs towards glioblastoma. Neither differences in the migratory and anisotropic properties of NSCs and MSCs for glioblastoma nor key molecules causing the differences have been reported so far. Additionally, since the high expression of CXCL12 in other malignant tumors (pancreatic cancer and the like) is pointed out, a migratory property towards tumors other than glioblastoma is also expected.

REFERENCES

1. Kim, S. U., Jeung, E. B., Kim, Y. B., Cho, M. H., Choi, K. C. Potential tumor-tropic effect of genetically engineered stem cells expressing suicide enzymes to selectively target invasive cancer in animal models. Anticancer Res. 31:1249-1258 (2011).
2. Vescovi, A. L., Galli, R., Reynolds, B. A. Brain tumour stem cells. Nat Rev Cancer. 6:425-436 (2006).
3. Fukaya, R. et al. MIF Maintains the Tumorigenic Capacity of Brain Tumor-Initiating Cells by Directly Inhibiting p53. Cancer Res. 76, 2813-2823 (2016).
4. Chen, L. Y. et al. RNASEQR—a streamlined and accurate RNA-seq sequence analysis program. Nucleic Acids Res. 40, e42 (2012).
5. Camp, J. G. et al. Multilineage communication regulates human liver bud development from pluripotency. Nature. 546, 533-538 (2017).
6. Ramilowski, J. A. et al. A draft network of ligand-receptor-mediated multicellular signalling in human. Nat Commun. 22, 7866 (2015).
7. Neftel, C. et al. An Integrative Model of Cellular States, Plasticity, and Genetics for Glioblastoma. Cell. 178, 835-849 (2019).
8. Nakada, M. et al. The phosphorylation of ephrin-B2 ligand promotes glioma cell migration and invasion. Int J Cancer. 126:1155-1165 (2010).

Example 3

(A) Background

Since induced pluripotent stem cells (iPS cells)-derived neural stem/progenitor cells (NSCs) have a high migratory ability towards a tumor tissue and a damage in the brain, the present inventors developed a therapy using the cells as a cellular delivery vehicle of therapeutic genes. Constantly stable expression was realized by inserting yeast cytosine deaminase (yCD)-uracil phosphoribosyl transferase (UPRT) fusion gene (yCD-UPRT) into a housekeeping gene locus (ACTB) of iPS cells as a therapeutic gene by a genome editing technique.

After gene introduction into iPS cells, cells have been selected using a drug resistance gene or a fluorescence gene so far. However, it is desirable in clinical application to remove a foreign gene such as a drug resistance gene. Furthermore, genome editing techniques with CRISPR-Cas9 or the like have a safety concern of off-target effect, in which a mutation is inserted into a non-targeted site. A new genome editing technique using CRISPR/Cas3 was developed recently, and it has been reported that off-target effect occurs infrequently because CRISPR/Cas3 has a recognition target sequence longer than that of CRISPR/Cas9.

(B) Summary of Invention

To prepare highly safe therapeutic stem cells, a new technique was developed in which the therapeutic gene is introduced into iPS cells using a genome editing technique having a low off-target effect, and then a foreign gene used for cell selection is removed.

Specifically, iPS cells are prepared in which the yCD-UPRT fusion gene, a drug resistance gene, and a fluorescence gene have been inserted into a housekeeping gene locus (ACTB) by a genome editing technique using CRISPR/Cas3. After selection using fluorescence and a drug, foreign genes (the drug resistance genes or the fluorescence genes) are removed using the Cre/loxP system. Cells into which a suicide gene (a gene coding for an enzyme that metabolize a prodrug and convert it to a tumoricidal substance) has been introduced kill themselves by administering a prodrug [Tamura R. Neurosurgical review. 2019].

(C) Method

<Human iPS Cells>

The human iPS cells (1210B2) used were obtained from the Center for iPS Cell Research and Application (CiRA), Kyoto University. 1210B2 was established by a method for introducing a reprogramming factor using an episomal vector for human peripheral blood mononuclear cells (Okita K, Yamakawa T, Matsumura Y, Sato Y, Amano N, Watanabe A, Goshima N, Yamanaka S. An efficient nonviral method to generate integration-free human-induced pluripotent stem cells from cord blood and peripheral blood cells. Stem Cells. 2013 March; 31(3):458-66.). Human iPS cells were inoculated on a plastic culture dish coated with iMatrix-511 (produced by Nippi, Incorporated) and subjected to maintenance culture using Stem Fit AK03 or AK03N medium (produced by Ajinomoto Co., Inc.) by a known feeder-free method (Nakagawa M, Taniguchi Y, Senda S, Takizawa N, Ichisaka T, Asano K, Morizane A, Doi D, Takahashi J, Nishizawa M, Yoshida Y, Toyoda T, Osafune K, Sekiguchi K, Yamanaka S. A novel efficient feeder-free culture system for the derivation of human induced pluripotent stem cells. Sci Rep. 2014 Jan. 8; 4:3594.).

<Differentiation Induction from Human iPS Cells into Neural Stem/Precursor Cells (NSCs)>

Differentiation induction from human iPS cells into NSCs was performed by a known method (Sugai K, Fukuzawa R, Shofuda T, Fukusumi H, Kawabata S, Nishiyama Y, Higuchi Y, Kawai K, Isoda M, Kanematsu D, Hashimoto-Tamaoki T, Kohyama J, Iwanami A, Suemizu H, Ikeda E, Matsumoto M, Kanemura Y, Nakamura M, Okano H. Pathological classification of human iPSC-derived neural stem/progenitor cells towards safety assessment of transplantation therapy for CNS diseases. Mol Brain. 2016 Sep. 19; 9(1):85.). First, a 10 M ROCK inhibitor Y276352 (FUJIFILM Wako Pure Chemical Corporation) was added to a medium of iPS cells, the iPS cells were incubated for 1 to 3 hours, then washed with PBS, and dissociated into single cells using TrypLE Select (produced by Life Technologies Corporation). The human iPS cells dissociated into the single cells were suspended in an EB (embryoid body)-forming medium to which a 10 μM ROCK inhibitor Y276352 was added (10 μM SB431542 and 100 nM LDN-193189 were added to Stem Fit medium not containing C liquid), inoculated at a concentration of $9.0\times10^3$ cells/75 μl per well of a low adhesive 96-well culture plate (Prime Surface 96V, manufactured by Sumitomo Bakelite Co., Ltd.) and cultured. Then, 75 μl of an EB-forming medium was added 1 day later, a half amount of the EB-forming medium was replaced every day thereafter, and the human iPS cells were cultured for 13 to 14 days to obtain EBs. The EBs were collected from each well and cultured in a neurosphere (NS) medium (to D-MEM/Ham's F-12 medium (containing HEPES) (produced by Wako Pure Chemical Industries, Ltd.) were added a 20 ng/ml recombination human epidermal growth factor (produced by PeproTech, Inc.), a 20 ng/ml recombination human fibroblast growth factor-2 (produced by PeproTech, Inc.), a $1\times10^3$ units/ml recombination human leukemia inhibitory factor (produced by NACALAI TESQUE, INC.), a 2% B-27 supplement (produced by Thermo Fisher Scientific K.K.), and 1 unit/ml heparin sodium (produced by AY PHARMACEUTICALS CO., LTD.)) for 7 days. The medium was replaced once every 3 or 4 days during culture. Cell aggregates were collected by centrifugation, dissociated into single cells using TrypLE Select, and then suspended in an NS medium. The single cells were inoculated into a low adhesive flask (manufactured by Corning Incorporated) at a concentration of $1\times10^5$ cells/ml and cultured for 10 days, with the medium replaced every 3 to 4 days, to obtain primary NSCs. Similarly, the primary NSCs were collected by centrifugation, dissociated into single cells using TrypLE Select, and suspended in an NS medium. The single cells were inoculated into a low adhesive flask at a concentration of $1\times10^5$ cells/ml and cultured for 7 to 10 days, with the medium replaced every 3 to 4 days, to obtain secondary, tertiary, quaternary, and quinary NSCs.

<Introduction of yCD-UPRT Gene into ACTB Gene Region with CRISPR/Cas3—Preparation of Therapeutic Stem Cells (TSCs)>

Figure 15A:
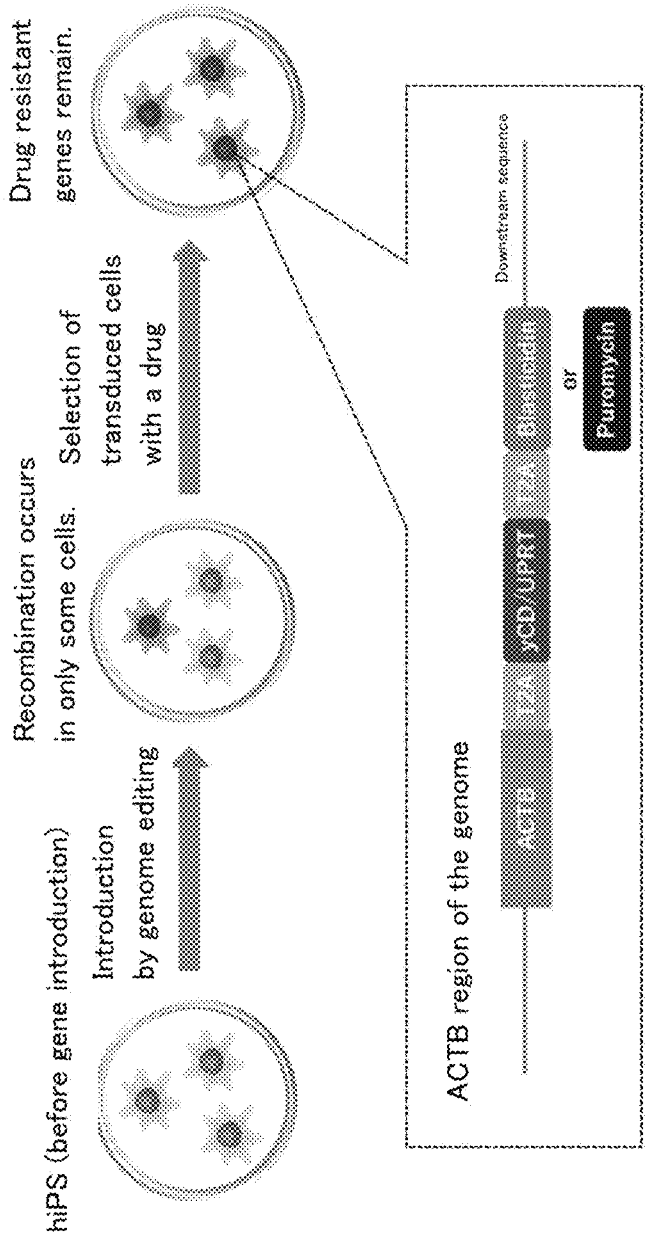
FIG. 15A shows a previous method for preparing therapeutic stem cells schematically.
Figure 15B:
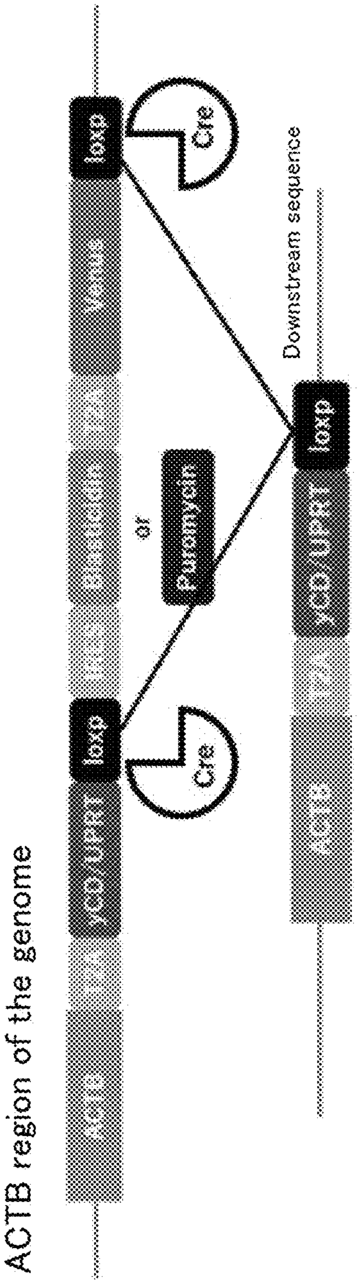
FIG. 15B shows a method for removing a selection marker gene with Cre/loxP schematically.
Figure 15C:
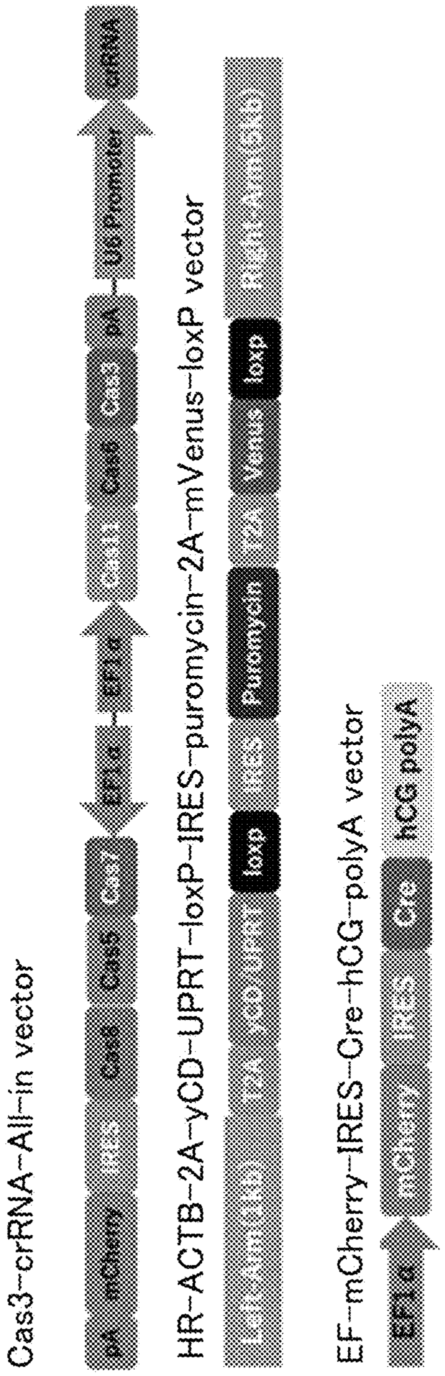
FIG. 15C shows the structures of various vectors used in Example 3.
Figure 16A:
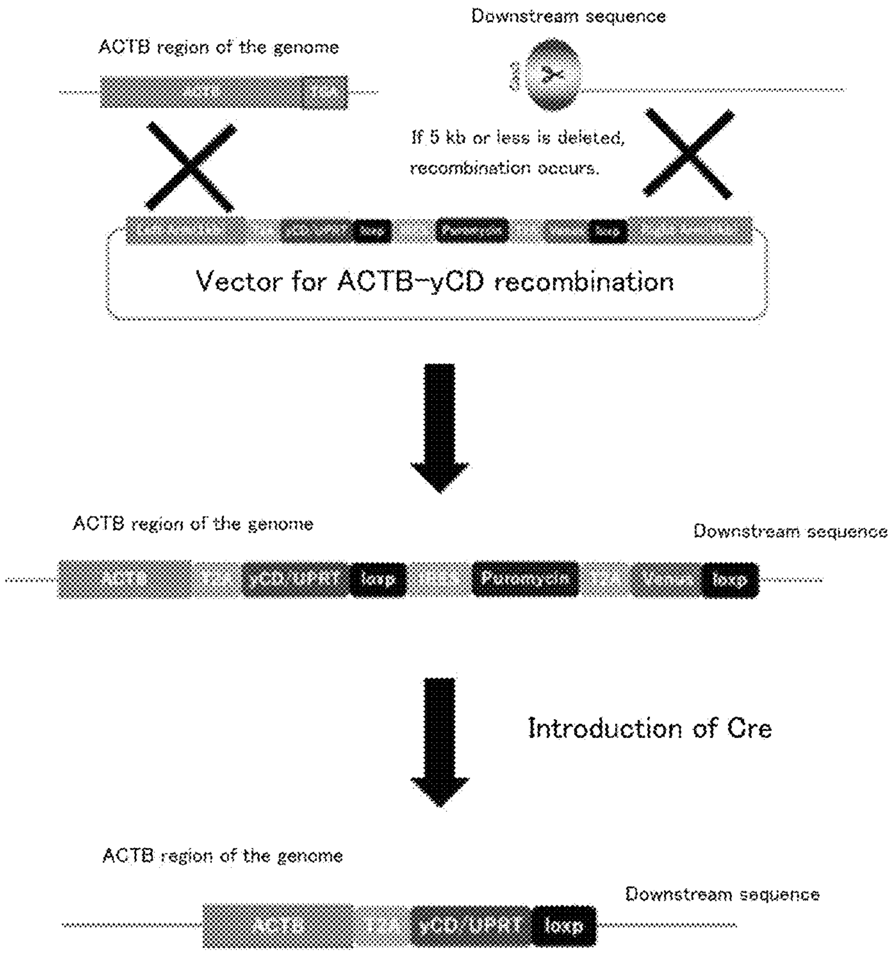
FIG. 16A shows the method for removing the puromycin gene and the Venus gene in Example 3 schematically.
Figure 16B:
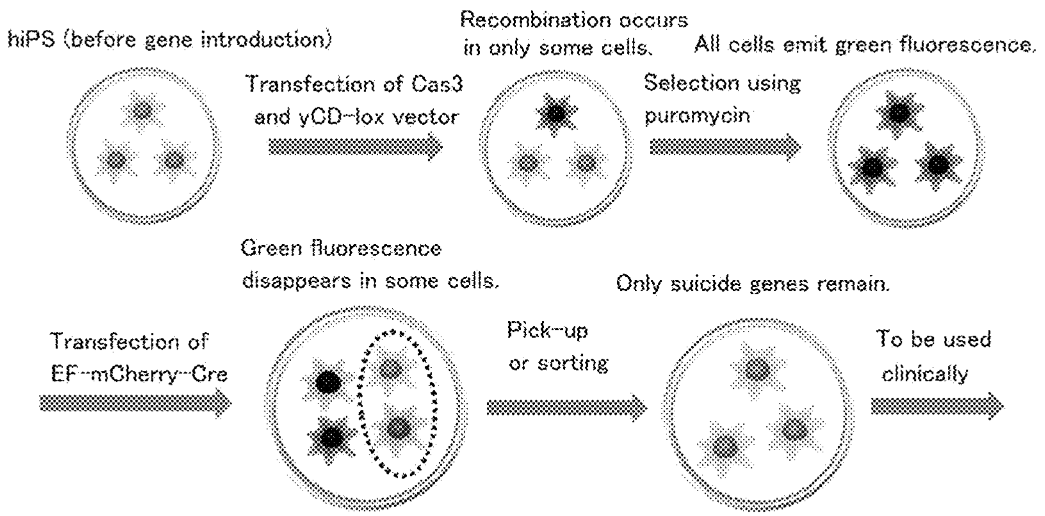
FIG. 16B shows the procedure of cloning in Example 3 schematically.
Figure 16C:
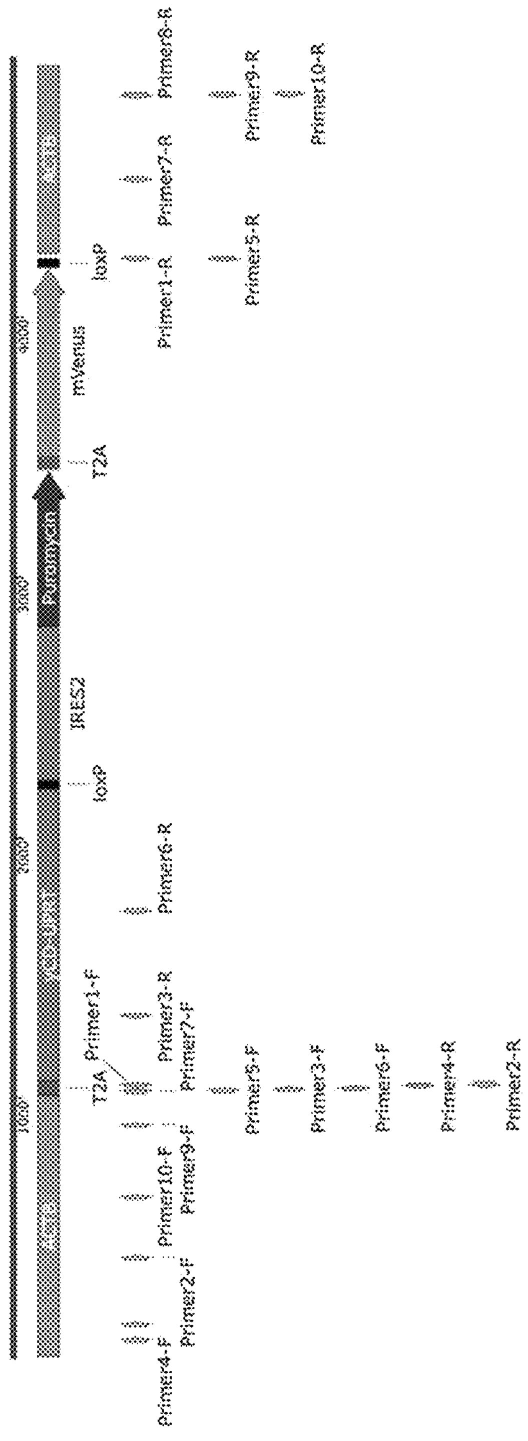
FIG. 16C shows the results of the genomic PCR in Example 3 (1).
Figure 16D:
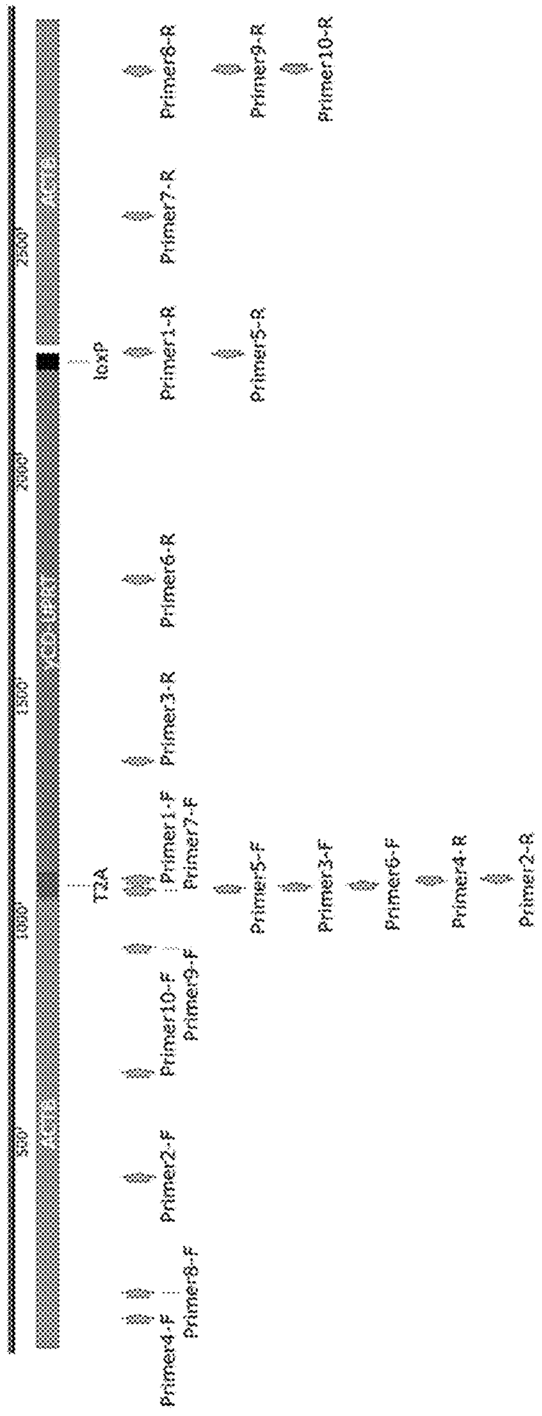
FIG. 16D shows the results of the genomic PCR in Example 3 (2).
Figure 16E:
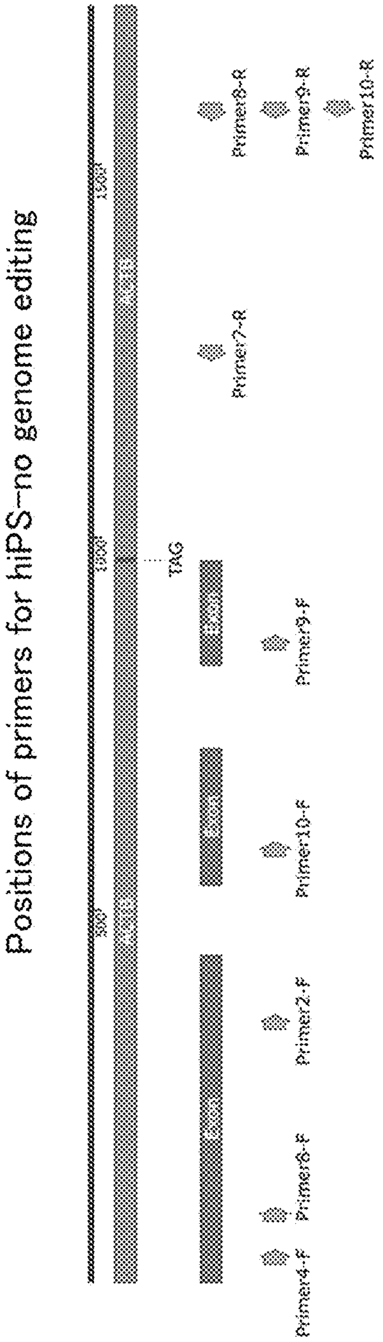
FIG. 16E shows the results of the genomic PCR in Example 3 (3).

Preparation of iPS Cells in which yCD-UPRT Gene has been Introduced into ACTB Gene Region (TiPS1 and TiPS2)

iPS cells were prepared in which the yCD-UPRT fusion suicide gene had been inserted into a housekeeping gene region ACTB (β-actin) by using the CRISPR/Cas3 genome editing technique. As a homologous recombination vector for genome editing, a construct (HR-ACTB-2A-yCD-UPRT-loxP-IRES-puromycin-2A-Venus-loxP) in which ACTB and yCD-UPRT that were being connected by a 2A peptide sequence, and downstream of these sequences, the IRES sequence, the puromycin resistance gene, 2A peptide, and a fluorescence protein Venus that were being connected and flanked by loxP sequences were inserted was prepared to incorporate yCD-UPRT into the ACTB (β-actin) gene region. As a vector for cleaving the genome, a construct (Cas3-crRNA-All-in) which expresses crRNA targeting the vicinity of the stop codon of ACTB and a series of Cas3-related proteins was prepared. These constructs were introduced into the human iPS cell line (1210B2) by electroporation and cultured in the presence of puromycin S, and the cloning was performed by colony pickup. The iPS cell line with homologous recombination (TiPS1) was confirmed by nucleotide sequence confirmation by the genomic PCR and the genomic sequencing of clones. As a vector for Cre/loxP recombination, a construct (EF-mCherry-IRES-Cre-hCGpolyA) was prepared in which a fluorescence protein mCherry, an IRES sequence, Cre protein, and a human growth hormone polyadenylation signal are connected downstream of the EF promoter. This construct was introduced into TiPS1 by electroporation, and cells in which fluorescence of mCherry was observed, and fluorescence of Venus disappeared were cloned by sorting (FIGS. 15 and 16). The iPS cell line from which the selection marker was removed (TiPS2) was confirmed by nucleotide sequence confirmation by the genomic PCR and the genomic sequencing of clones.

Preparation of yCD-UPRT-Expressing NSCs (TSC1 and TSC2)

Differentiation into NSCs of iPS cells into which yCD-UPRT had been incorporated into ACTB (TiPS1 and TiPS2) was induced to obtain secondary to quinary NSCs. TSC1 is therapeutic NSCs into which TiPS1 has been differentiated and in which the selection marker sequence is remaining, and TSC2 is therapeutic NSCs into which TiPS2 has been differentiated and in which the selection marker sequence has been removed (FIG. 17). To show that cell proliferation, CD expression level, and the like are not changed even after removal of the selection marker (TSC2), TSC1 was cultured for comparison. Cells were cultured while adding 1 μg/ml puromycin S to the TSC1 medium at all times. It was confirmed that cell deaths of TSC1 and TSC2 were induced by adding 1 to 7 g/ml 5-fluorocytosine (5-FC) to the medium. Cell deaths were assessed using a cell proliferation/cytotoxicity assay kit Cell Counting Kit-8 (CCK-8) (Dojindo Molecular Technologies, Kumamoto, Japan).

Analysis of Gene Expressions of TiPSC1, TiPSC2, TSC1, and TSC2

By real time qPCR, the mRNA expressions of iPS cell line not subjected to genome editing (iPS-nega), TiPSC1, TSC1, TiPSC2, TSC2, iPS-Cas9 subjected to genome editing using CRISPR/Cas9, and NSC-Cas9 subjected to genome editing using CRISPR/Cas9 were compared. The mRNA expression levels of GAPDH, ACTB, yCD-UPRT, the puromycin resistance gene, and the Venus gene were measured using TB Green (registered trade name) Premix Ex Tag™ II (Takara Bio Inc.), and the expression level of each gene was normalized by the expression level of ACTB.

Confirmation of Antitumor Effects of TSC1 and TSC2 (TSC1 and TSC2)

Glioma cell line U87 ($1\times10^4$ cells) or glioma stem cell line hG008 ($1\times10^4$ cells) and TSC1 or TSC2 ($5\times10^3$ cells) were co-cultured for 1 day using a low adhesive 96-well culture plate (Prime Surface 96V, manufactured by Sumitomo Bakelite Co., Ltd.), then 5-FC (2 g/ml) was added, and cell deaths were assessed using a cell proliferation/cytotoxicity assay kit Cell Counting Kit-8 (CCK-8) 5 days later.

(D) Results

<Differentiation Induction into NSCs>

Figure 17A:
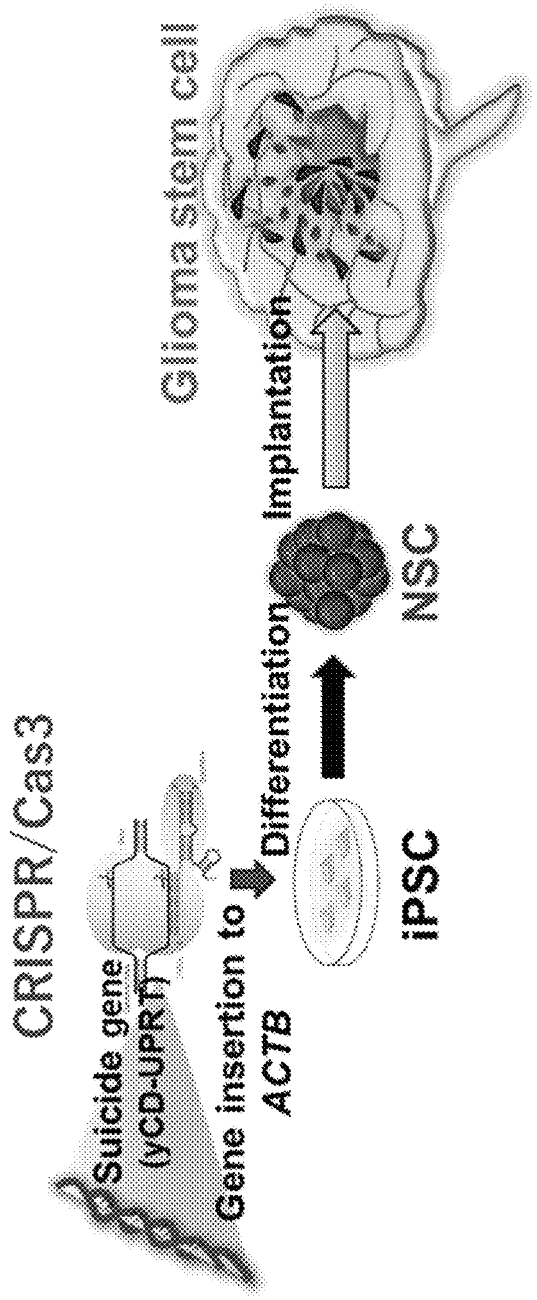
FIG. 17A shows a method for treating brain tumor using a suicide gene schematically.
Figure 17B:
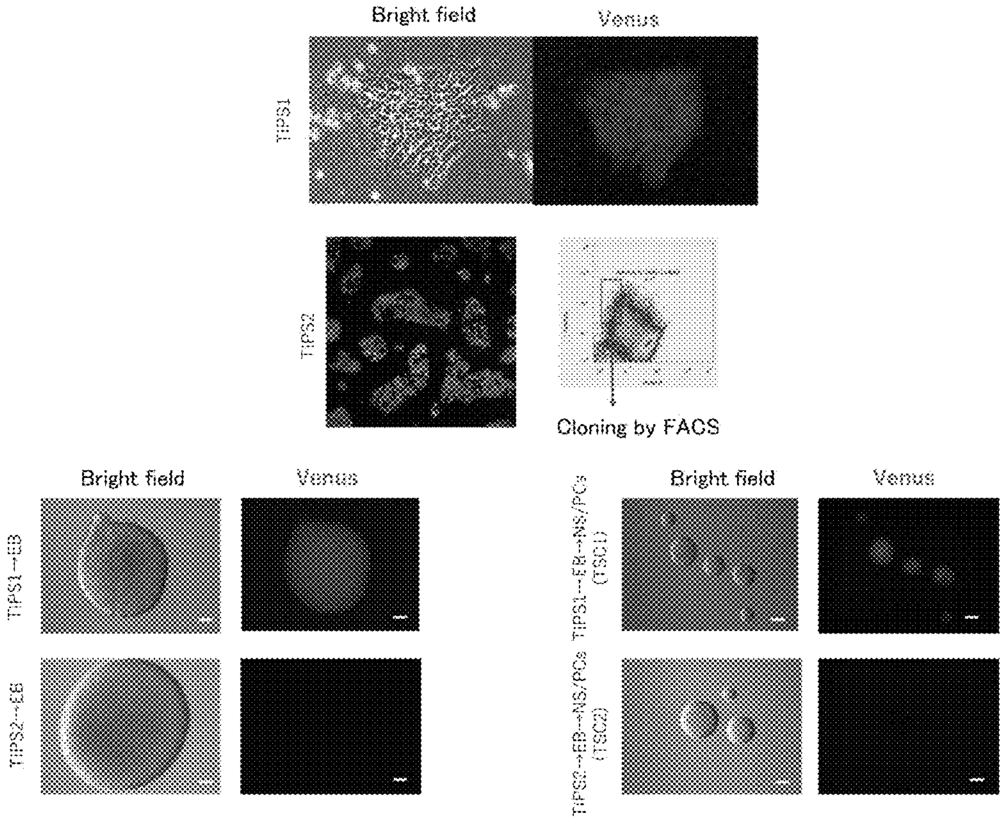
FIG. 17B shows microscopic photographs of iPS cells (upper row), embryoid bodies (left in the lower row), and neural stem cells (right in the lower row) used in Example 3.
Figure 17C:
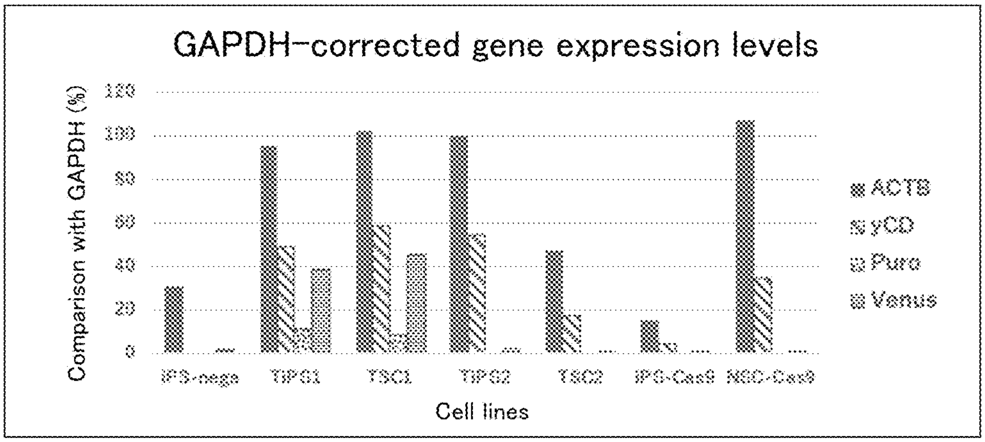
FIG. 17C shows the gene expression levels of the cell lines used in Example 3. The bars in each bar graph show the expression levels of GAPDH, yCD, puromycin, and Venus from the left.
Figure 17C:
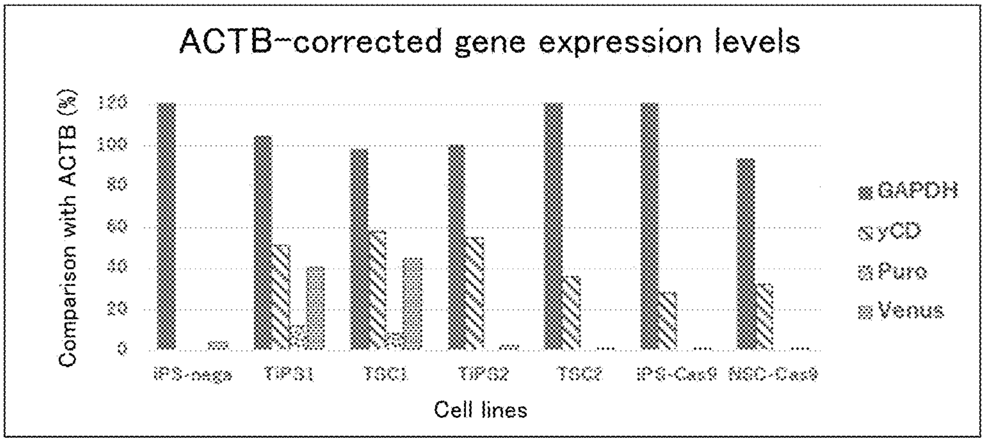

Differentiation induction from TiPS1 and TiPS2 into NSCs (TSC1 and TSC2) could be performed by the above-described method without problems. TSC1 was confirmed by the label with the Venus fluorescence protein (FIG. 17B). For gene expression, the expressions of yCD-UPRT and the selection marker were confirmed in TiPS1 and TSC1, and the expression of yCD-UPRT and the absence of expression of the selection marker were confirmed in TiPS2 and TSC2 (FIG. 17C). Furthermore, the expression level of yCD-UPRT corrected by the expression level of GAPDH or ACTB did not differ greatly from those in iPS-Cas9 and NSC-Cas9 (FIG. 17C). The expression level of yCD-UPRT was approximately 25% to 50% of that of ACTB because yCD-UPRT was inserted in a heterogeneous form.

<Resistance of TSC1 and TSC2 to Puromycin>

Figure 18:
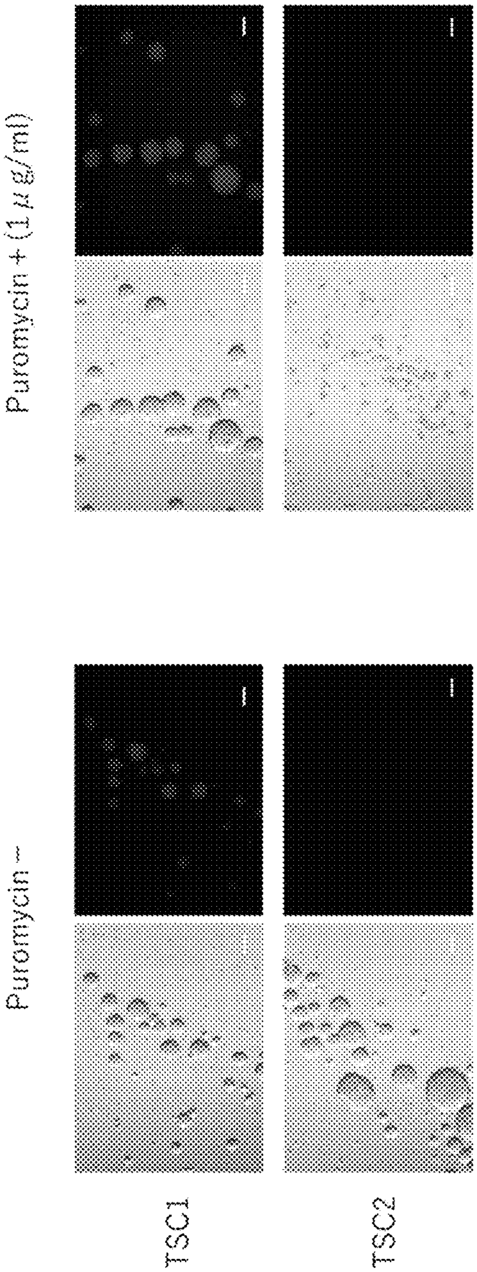
FIG. 18 shows microscopic photographs of the neural stem cells used in Example 3 in the presence or absence of puromycin.

After the addition of puromycin, TSC1 could be selected without problems by the puromycin resistance gene. TSC2 was killed by puromycin immediately, confirming that the puromycin resistance gene passed through by the Cre/loxP system as predicted (FIG. 18).

<Susceptibility of TSC1 and TSC2 to 5-FC>

Figure 19:
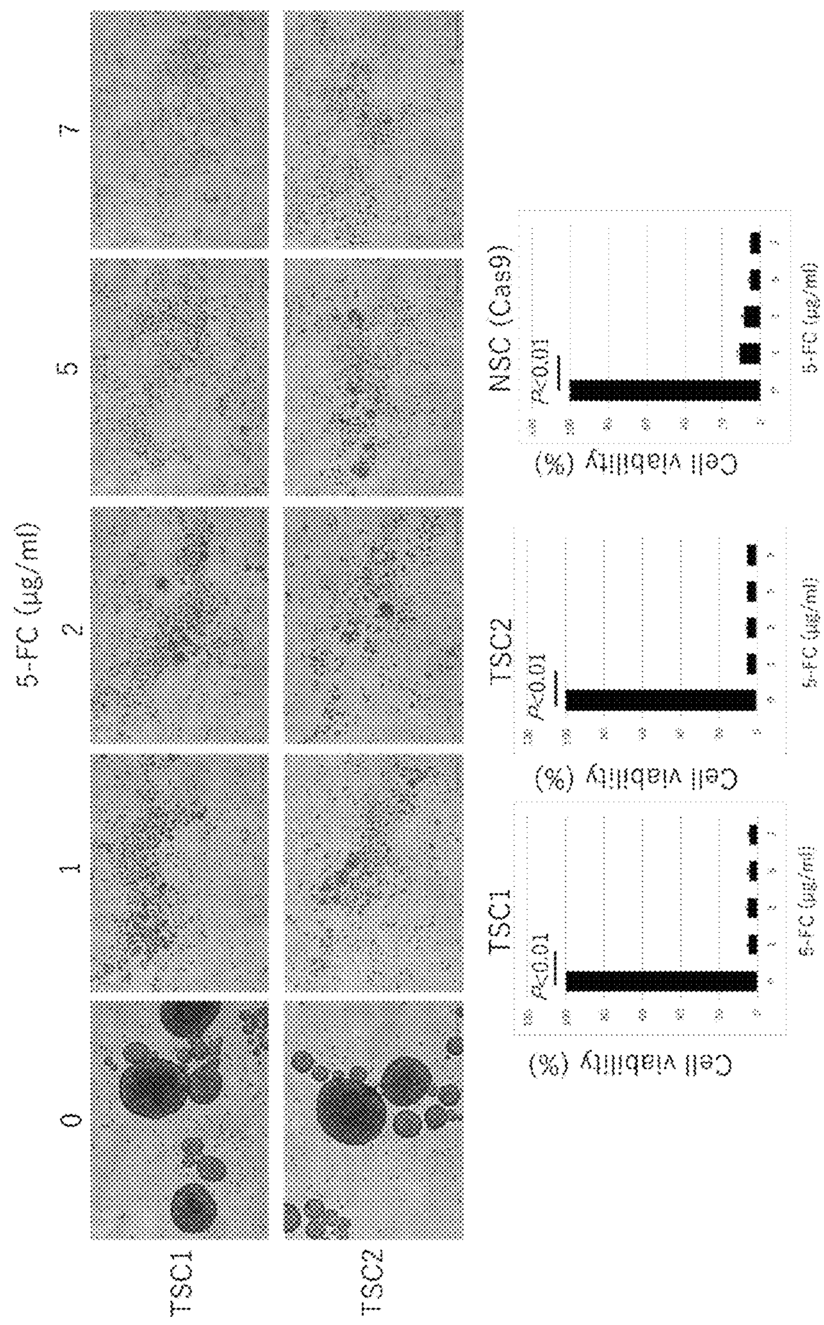
FIG. 19 shows microscopic photographs of the neural stem cells used in Example 3 at various 5-FC concentrations (upper row) and graphs of cell viability (lower row).

Both TSC1 and TSC2 had a favorable susceptibility to 5-FC and were completely killed at a concentration of 1 g/ml (FIG. 19). NSCs similarly prepared by introducing yCD-UPRT into the ACTB locus with CRISPR/Cas9 had an equivalent susceptibility (FIG. 19).

<Antitumor Effects of TSC1 and TSC2>

Figure 20:
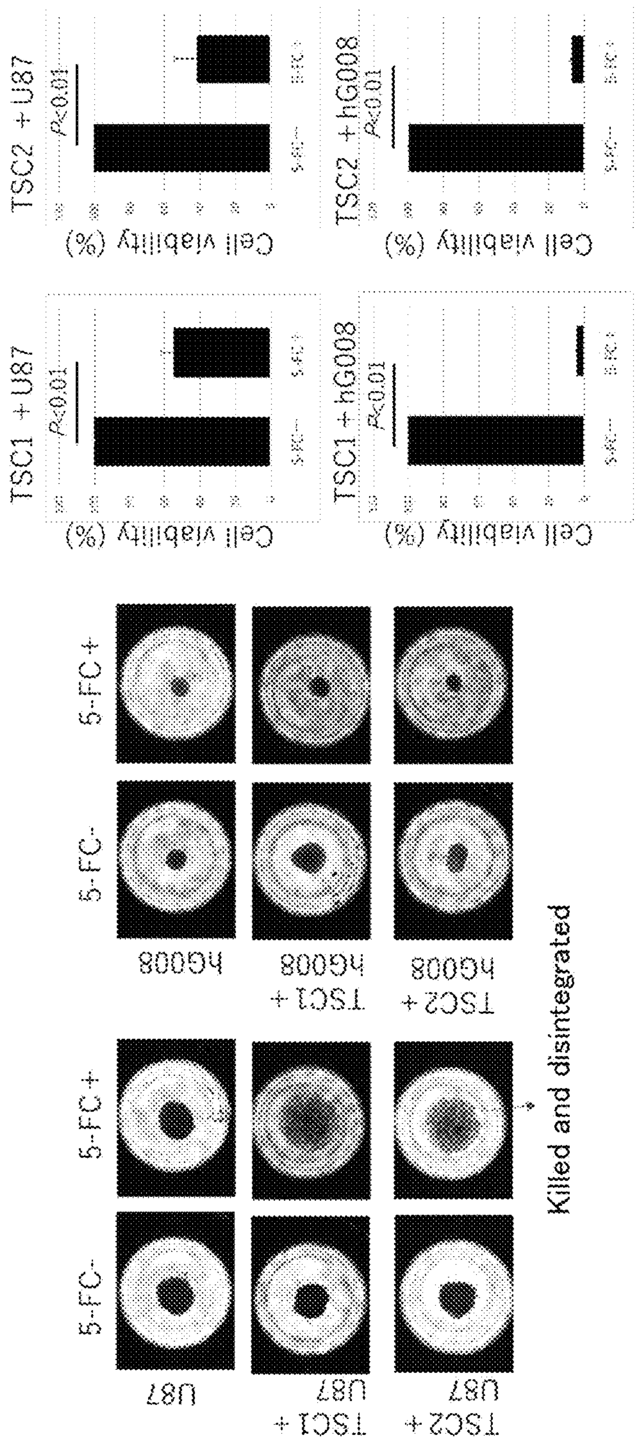
FIG. 20 shows photographs (left) and graphs (right) of antitumor effects of the neural stem cells used in Example 3 in the presence or absence of 5-FC.

TSC1 and TSC2 were co-cultured with glioma cell line U87 and glioma stem cell line hG008, and 5-FC (2 μg/ml) was administered. Cell deaths were assessed by CCK-8 assay. Significant tumor cell deaths occurred in both cells after the administration of the prodrug (FIG. 20). When 5-FC was administered with either U87 or hG008 alone, no particular tumor cell death was observed (FIG. 20).

Example 4

(A) Summary of Mutant loxP Sequences

Figure 21:
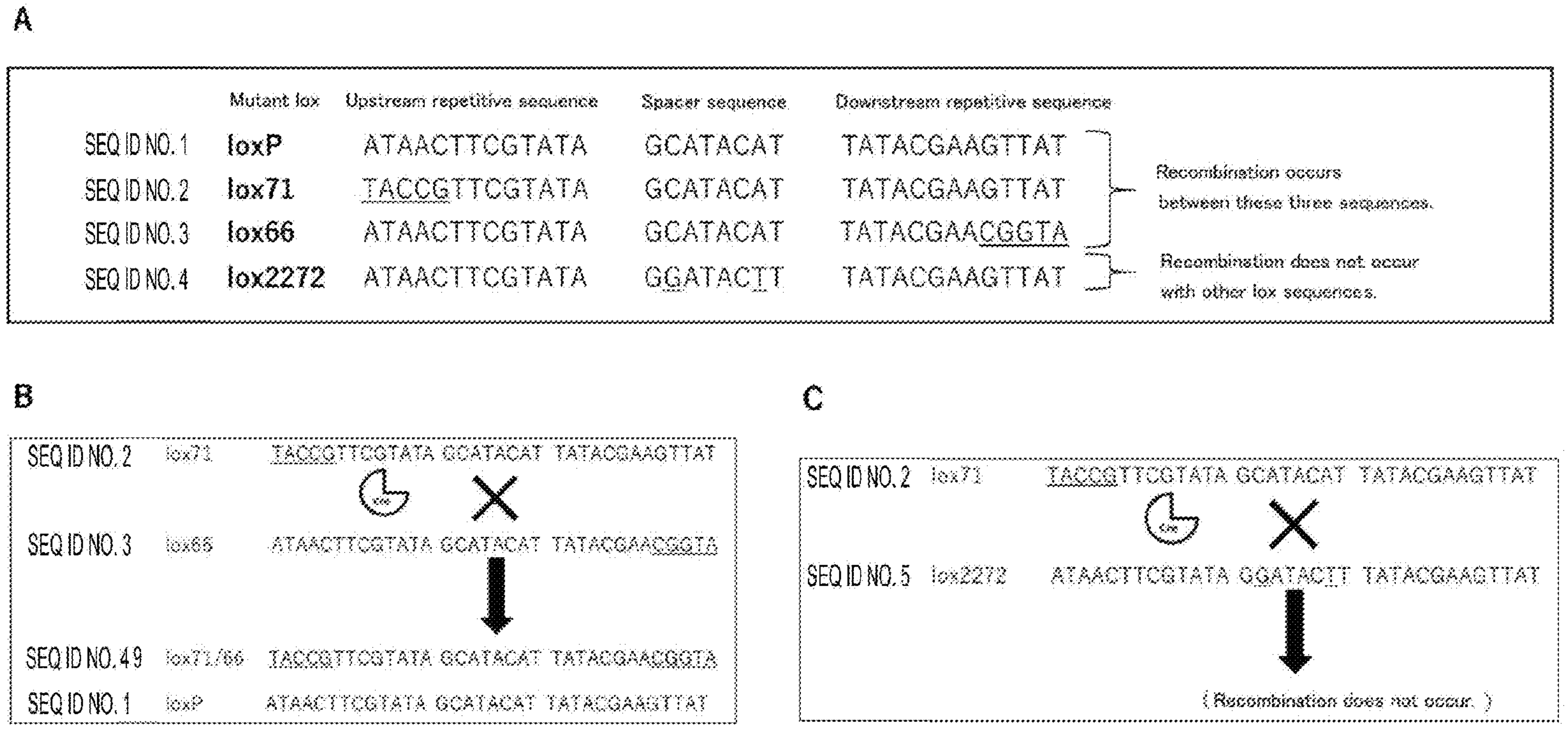
FIG. 21 shows nucleotide sequences of the loxP sequence and mutant lox sequences.

As shown in FIG. 21A, a lox sequence consist of an upstream repetitive sequence, a spacer sequence, and a downstream repetitive sequence. Mutant lox sequences with a mutation at each site have already been developed (the mutation sites are underlined in FIG. 21A).

When lox71 and lox66 are recombined, one becomes lox71/66, and the other one becomes loxP (FIG. 21B). Because lox71/66 has a mutation at either end, the sequence is hardly recognized by Cre. Therefore, safety can be increased if lox71/66 is allowed to remain in the genome. Furthermore, lox2272, which has a mutation in the spacer sequence, recombines only with the same lox2272 (FIG. 21C).

(B) Background (1) Method for Removing Antibiotic Resistance Gene Using Cre/Mutation Lox System To increase the safety of the method for removing a drug resistance gene or a fluorescence gene described in Example 3, a method for removing a drug resistance gene or a fluorescence gene using mutant loxP sequences (mutation in an arm region) instead of loxP was developed.

The Cre/loxP system can remove a DNA sequence (for example, a drug resistance gene) flanked by loxP sequences by expressing Cre protein. However, one loxP sequence remains eventually, and thus there is a risk that it may react with Cre. Accordingly, to reduce the risk, a method for flanking a DNA sequence to be removed (for example, a drug resistance gene) by loxP sequences which have a mutation in the repetitive sequence (lox71 and lox66) was developed. A mutant loxP sequence lox71 has a mutation incorporated in the upstream repetitive sequence portion, and lox66 has a mutation incorporated in the downstream repetitive sequence portion. As a result, because the lox71/66 fusion sequence remaining after removal of the flanked gene has a mutation at either end, the risk of reacting with Cre becomes minimal, enabling a safer gene treatment (FIG. 22B).

(2) Method for Inserting Second Gene Using Cre/Mutant Lox System

A method for inserting a second gene and removing a drug resistance gene or a fluorescence gene using a mutant loxP sequence (mutation in the spacer sequence) was developed.

Since lox2272, a mutant loxP sequence, has a mutation in the spacer sequence, it has a property of reacting with the same mutant lox sequence by Cre. Making use of this property, loxP with a mutation in the spacer sequence enables homologous recombination of the target genes (in the example, recombination of the region flanked by lox71 and lox2272 and the region flanked by lox66 and lox2272). As a result, another therapeutic gene (the second gene) can be inserted in addition to the suicide gene, and the drug gene can be removed. The Cre/mutation lox system has a high introduction efficiency and is safe with a minimal off-target problem in genome editing techniques using Cas3 or the like (FIG. 22C).

(C) Method (1) Removing Drug Resistance/Marker Genes

Figure 23:
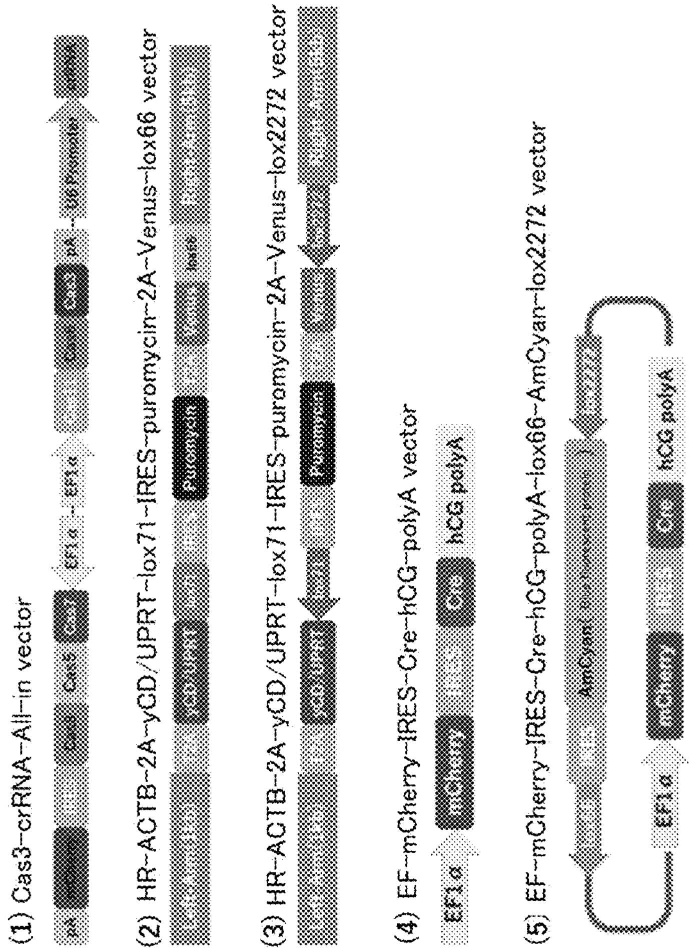
FIG. 23 shows the structures of the vectors used in Example 4.

A Cas3-expression plasmid (FIG. 23 (1)) and an ACTB recombination plasmid (FIG. 23 (2)) were introduced into human iPS cells by electroporation to replace the stop codon of ACTB in the genome of human iPS cells with 2A-yCD/UPRT-lox71-IRES-puromycin resistance gene-2A-Venus-lox66. 1 g/ml puromycin was added to the medium, cells were cultured, and cells showing recombination were selected. The EF-mCherry-IRES-Cre plasmid (FIG. 23 (4)) was introduced into these cells by electroporation again, and Venus-/mCherry+ cells were cloned 72 hours later. The genome was extracted from the cloned cells, and the DNA at the insertion site was amplified by PCR to confirm the band lengths, and then the sequences were confirmed. Then, differentiation into NS/PCs was induced.

(2) Insertion of Second Gene

A Cas3 expression plasmid (FIG. 23 (1)) and an ACTB recombination plasmid (FIG. 23 (3)) were introduced into human iPS cells by electroporation to replace the stop codon of ACTB in the genome of human iPS cells with 2A-yCD/UPRT-lox71-IRES-puromycin resistance gene-2A-Venus-lox2272. 1 μg/ml puromycin was added to the medium, cells were cultured, and cells showing recombination were selected. A plasmid containing EF-mCherry-IRES-Cre and lox66-IRES-AmCyan-lox2272 sequences (FIG. 23 (5)) was introduced into these cells by electroporation again, and Venus-/AmCyan+/mCherry+ cells were cloned 72 hours later. The genome was extracted from the cloned cells, and the DNA at the insertion site was amplified by PCR to confirm the band lengths, and the gene sequences were confirmed. Then, differentiation into NS/PCs was induced.

(3) Confirmation of Gene Expression

The mRNA expressions of the cells selected in (1) and (2) were compared by real time qPCR. The mRNA expression levels of the genes of GAPDH, ACTB, yCD-UPRT, puromycin resistance gene, Venus, and AmCyan were measured using TB Green (registered trade name) Premix Ex Taq™ II (Takara Bio Inc.). The expression level of each gene was normalized by the expression level of ACTB or GAPDH.

(4) Confirmation of Antitumor Effects

Glioma stem cell line hG008 ($6\times10^3$ cells) and NS/PCs ($3\times10^3$ cells) established in (1) or (2) were co-cultured for 1 day using a low adhesive 96-well culture plate (Prime Surface 96V, manufactured by Sumitomo Bakelite Co., Ltd.), then 5-FC (5 g/ml) was added, and an assay was performed using cell proliferation/cytotoxicity assay kit Cell Counting Kit-8 (CCK-8) 5 days later.

Figure 24:
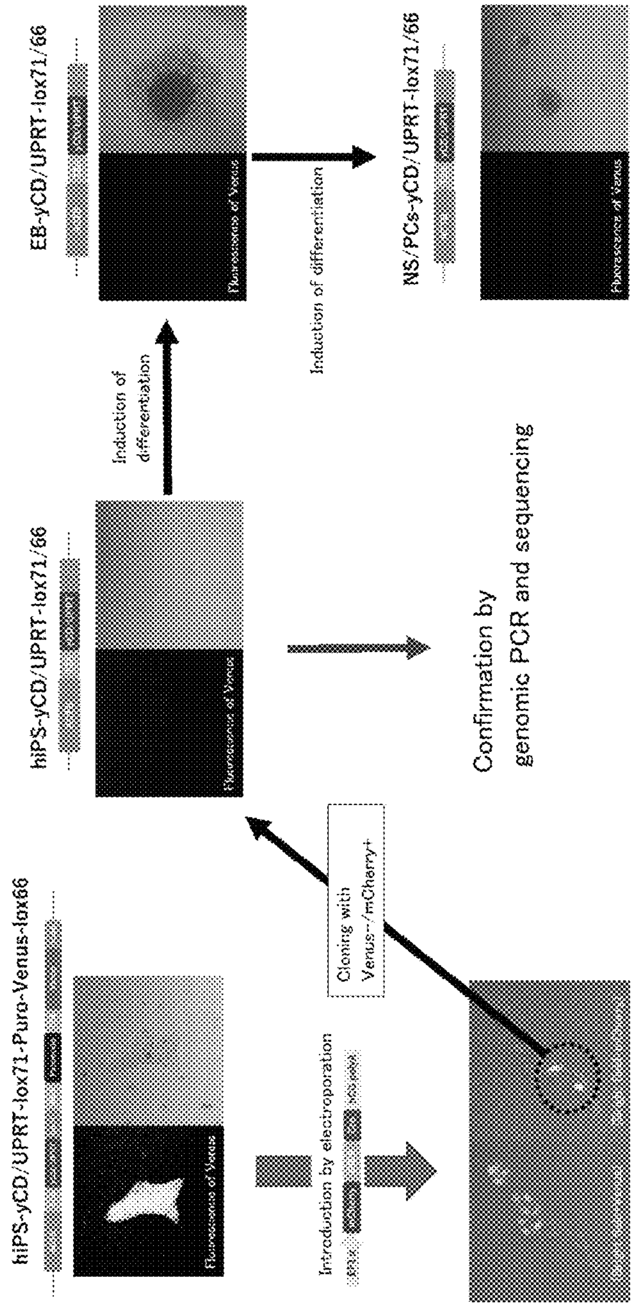
FIG. 24 shows a method for removing the drug resistance or fluorescence gene (1).
Figure 25B:
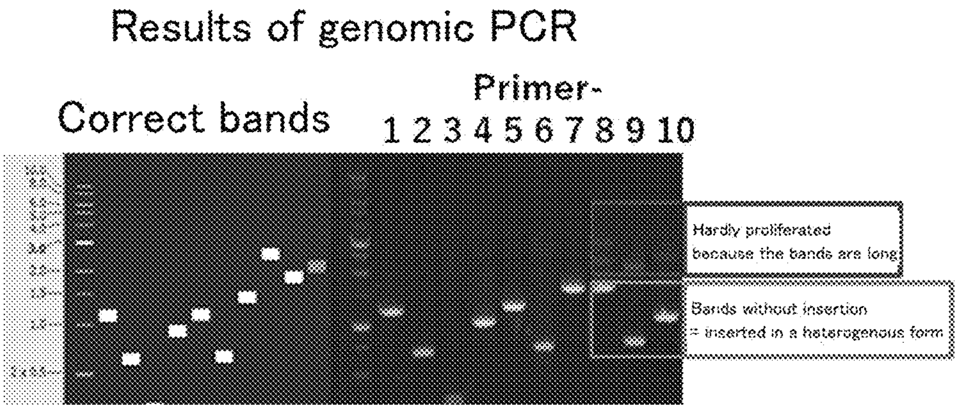
FIG. 25B shows a method for removing the drug resistance or fluorescence gene (3).
Figure 25C:
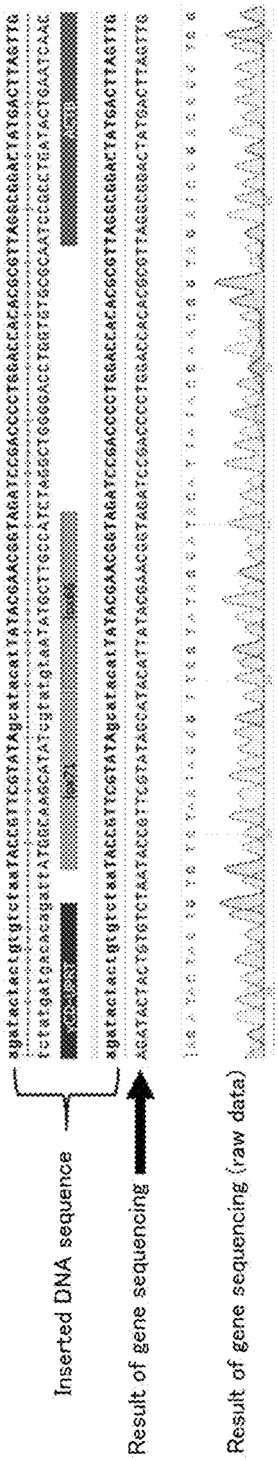
FIG. 25C (SEQ ID NOS: 45 and 46) shows a method for removing the drug resistance or fluorescence gene (4).

(D) Results (1) Removal of Drug Resistance/Marker Genes iPS cells into which the suicide gene had been inserted and from which the drug resistance/marker gene had been removed (ACTB-2A-yCD/UPRT-lox71/66 had been incorporated) were established, and differentiation into embryoid bodies (EBs) and NS/PCs could be induced (FIG. 24). It was confirmed by the genome by genome PCR and gene sequencing analysis that the sequences were correctly incorporated (FIGS. 25A to 25C).

Figure 26:
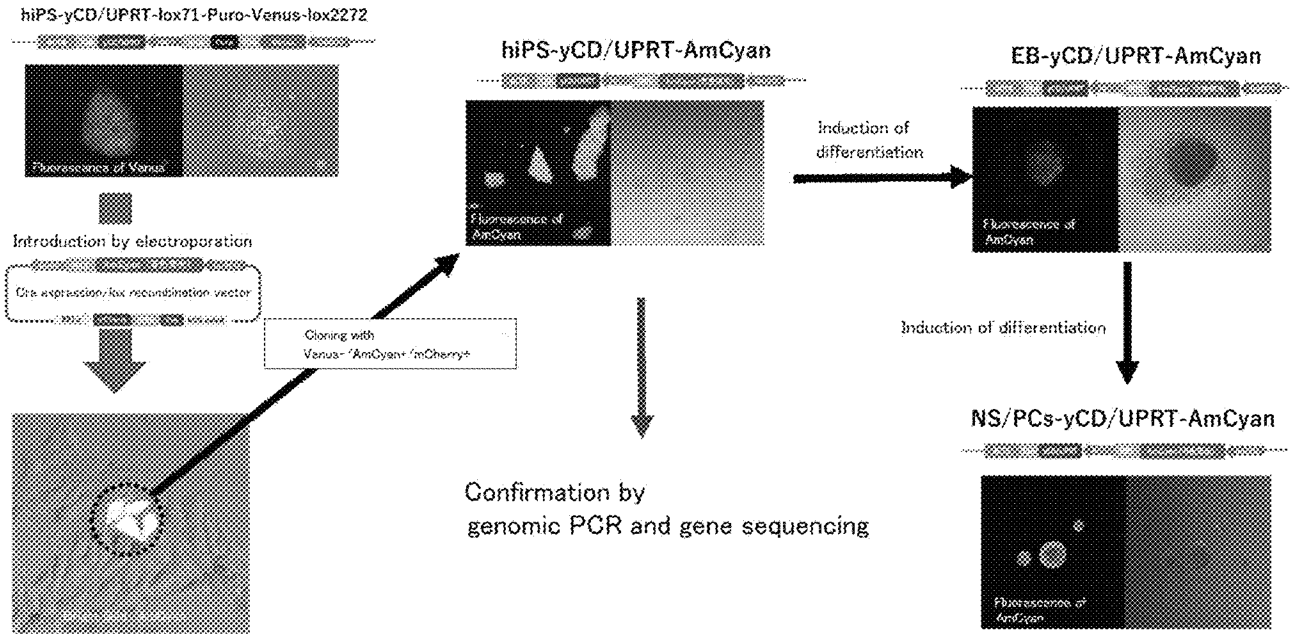
FIG. 26 shows a method for inserting the second gene (1).
Figure 27B:
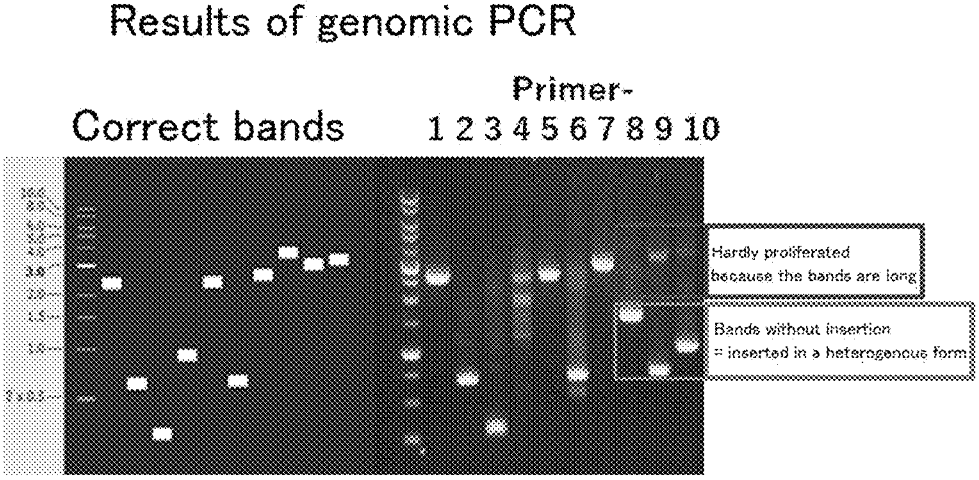
FIG. 27B shows a method for inserting the second gene (3).
Figure 27C:
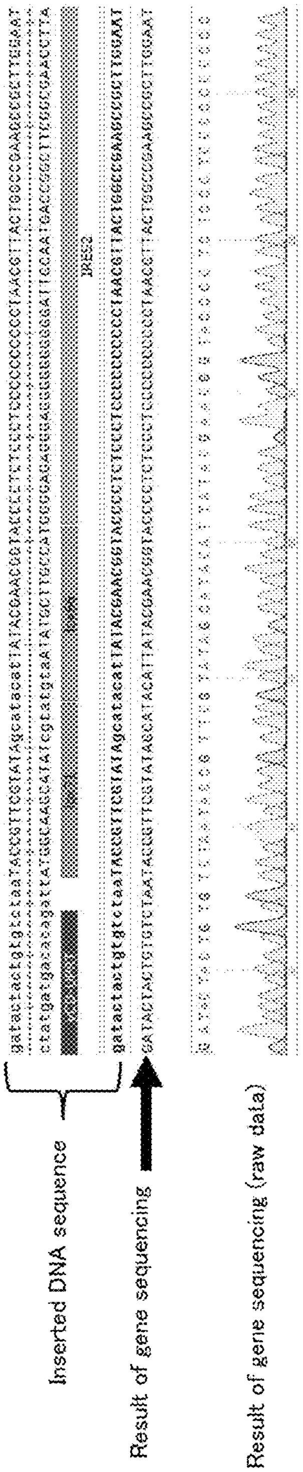
FIG. 27C (SEQ ID NOS: 47 and 48) shows a method for inserting the second gene (4).

(2) Insertion of Second Gene iPS cells into which a suicide gene and a second gene had been inserted and from which the drug resistance/marker gene had been removed (ACTB-2A-yCD/UPRT-lox71/66-IRES-AmCyan-lox2272 had been incorporated) were established, and differentiation into NS/PCs could be induced. Fluorescence of the second gene (AmCyan) was confirmed in the embryoid bodies (EBd) and NS/PCs (FIG. 26). It was confirmed by genome PCR and gene sequencing analysis that the sequences were correctly incorporated in the genome (FIGS. 27A to 27C).

(3) Confirmation of Gene Expressions

Figure 28:
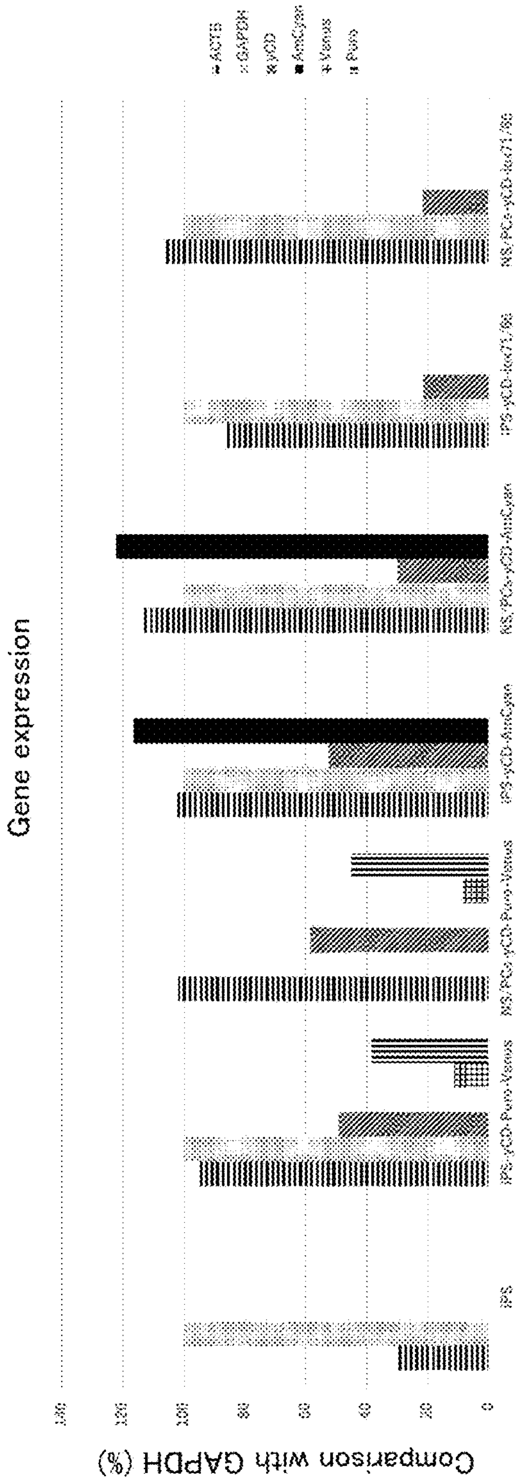
FIG. 28 shows the expressions of various genes in iPS cells and neural stem cells established by the method for removing a drug resistance or fluorescence gene.

Expression of yCD and loss of Venus and puromycin resistance genes were confirmed in iPS cells and NS/PCs established in (1) (FIG. 28). Expression of yCD and the second gene (AmCyan) and loss of the Venus and puromycin resistance genes were confirmed in iPS cells and NS/PCs established in (2) (FIG. 28).

Figure 29:
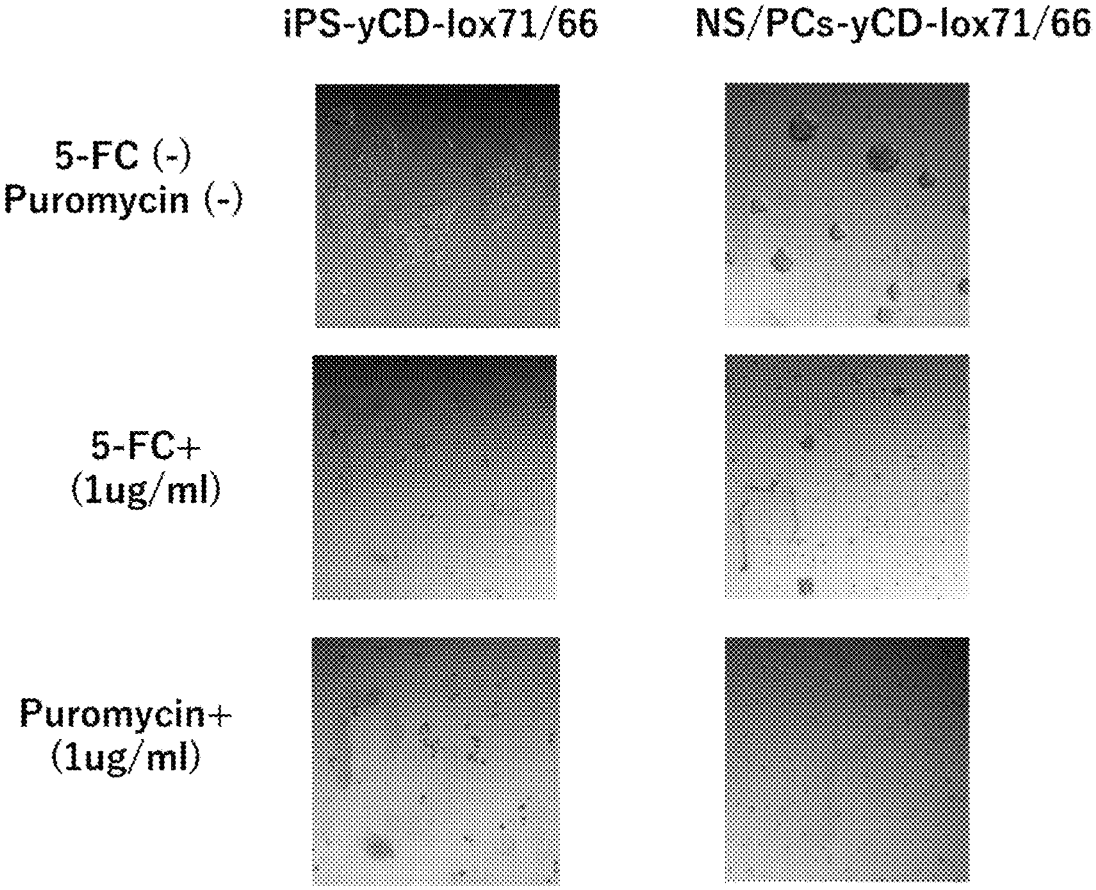
FIG. 29 shows responses to 5-FC and puromycin of iPS cells and neural stem cells established by the method for removing a drug resistance or fluorescence gene.
Figure 30:
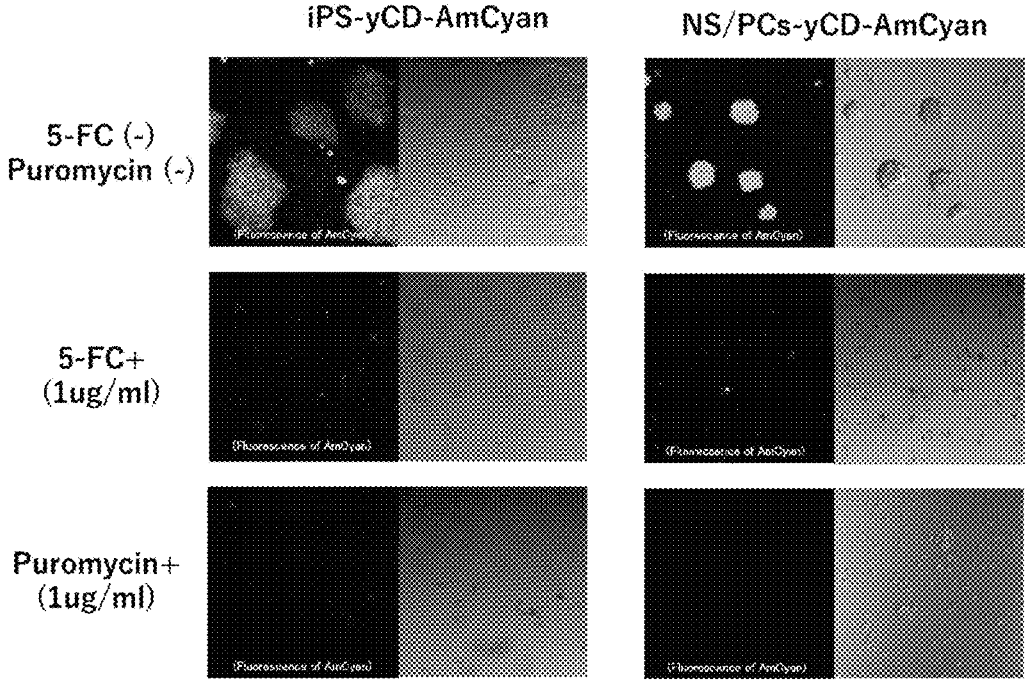
FIG. 30 shows responses to 5-FC and puromycin of iPS cells and neural stem cells established by a method for inserting the second gene.

Furthermore, it was confirmed that cells were killed by administering 5-FC and puromycin in iPS cells and NS/PCs established in (1) (FIG. 29). It was confirmed that cells were killed by administering 5-FC and puromycin in iPS cells and NS/PCs established in (2) (FIG. 30)

(4) Confirmation of Antitumor Effects

Figure 31:
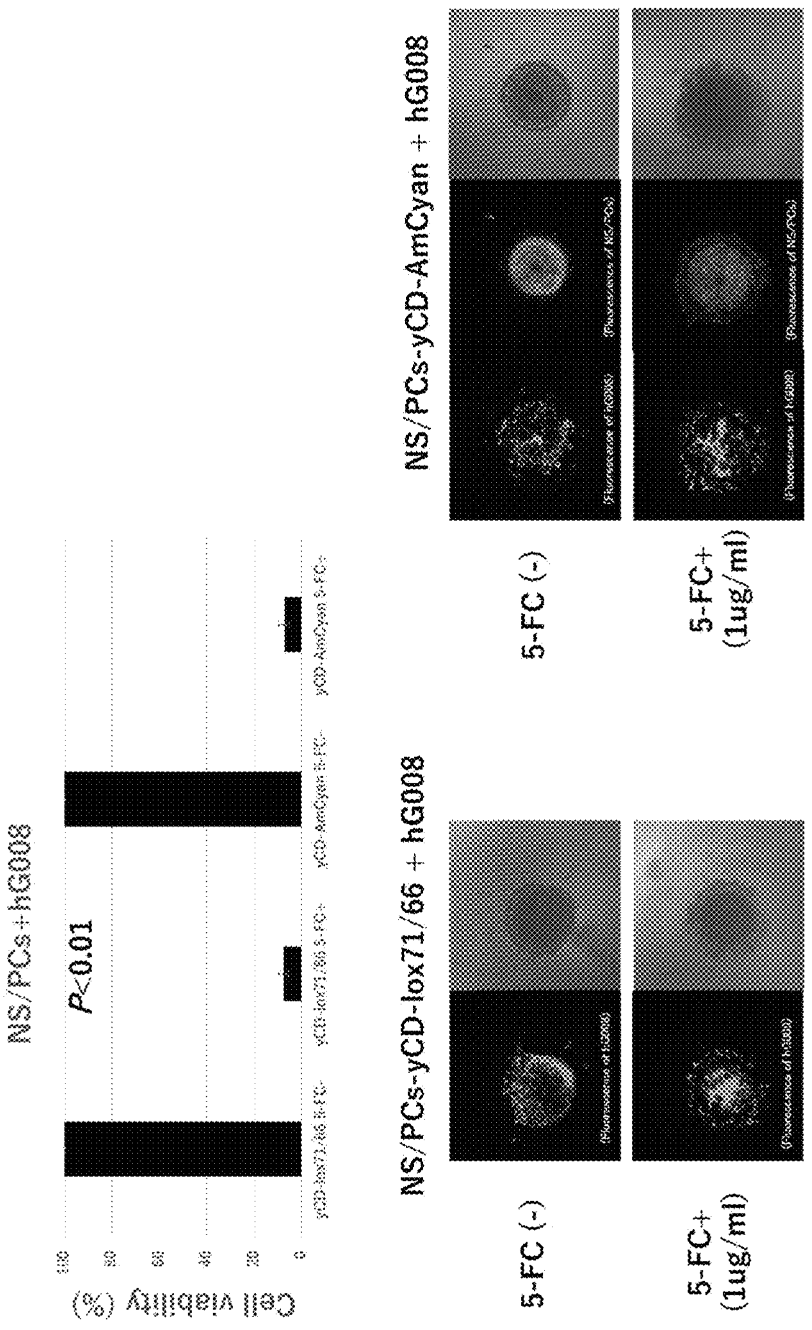
FIG. 31 shows antitumor effects of neural stem cells established by the method for removing a drug resistance or fluorescence gene or the method for inserting the second gene.

NS/PCs established in (1) or (2) and glioma stem cell line hG008 were co-cultured, and 5-FC (5 μg/ml) was administered. Cell deaths were assessed by CCK-8 assay. Significant tumor cell deaths occurred in both cells after administration of the prodrug (FIG. 31).

[Example 5] Effects Against Tumors Other than Brain Tumor

Effects against pancreatic cancer as one example of tumors other than brain tumor are described hereinafter, but similar effects are exhibited against other tumors.

(A) Background

The morbidity of cancer of the digestive system is high. In particular, pancreatic cancer was the fifth most common cause of cancer death in men (17,060 deaths) and the third most common cause in women (16,415 deaths) in 2016, which means that there were more deaths from pancreatic cancer than those from stomach cancer in women [refer to National Cancer Center Cancer Information Service]. The 5-year relative survival rate for pancreatic cancer was 7.9% in men and 7.5% in women, and pancreatic cancer has the worst prognosis compared with cancers of other organs [10-year relative survival rates by each site and clinical stage of Japanese Association of Clinical Cancer Centers]. Multidisciplinary treatment is performed making full use of surgical therapy, chemotherapy, and radiotherapy. In the current situation, however, since systemically administered chemotherapeutic drugs cause severe adverse drug reactions, and many patients have a condition considered to be already unresectable or refractory even with resection at the time of diagnosis because of a property of developing distant metastasis easily, tumor infiltration into arteries, and the like. Therefore, there is an unmet need for development of new therapies. 5-FU is used as one of common chemotherapeutic agents for pancreatic cancer. Since NS/PCs derived from suicide gene-introduced iPS cells established by the present inventors exhibit the anisotropic and migratory properties for malignant tumors, the anticancer agent 5-FU can be administered at a high concentration to the site of tumor.

(B) Method

Figure 32:
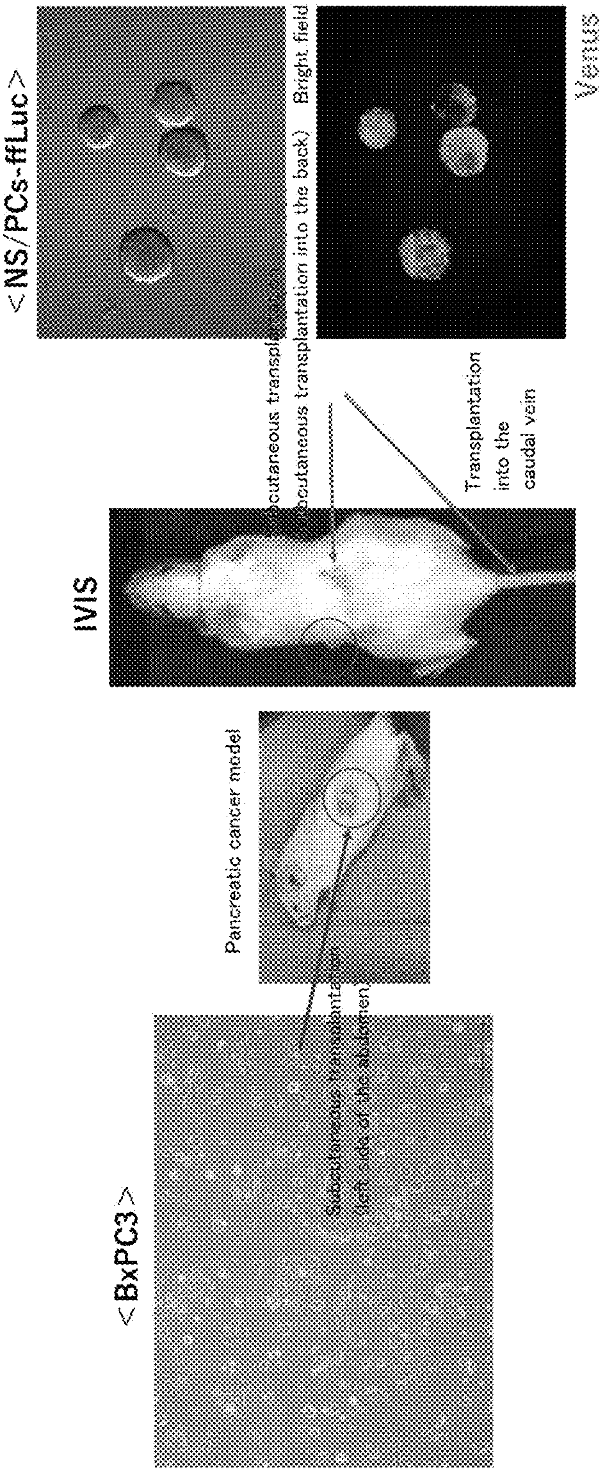
FIG. 32 shows the summary of the experiment method of Example 5.

Human pancreatic cancer cell line BxPC3 ($5\times10^6$ cells) was transplanted subcutaneously into the left side of the abdomen of a NOD/SCID mouse (6 w, female). A suicide gene yCD-UPRT-introduced iPS-NS/PCs (ffLuc) ($5\times10^5$ cells) was subcutaneously transplanted into the back or administered into the caudal vein 7 days later (FIG. 32). The NS/PCs were infected with the ffLuc (fusion gene of Venus fluorescence protein and Luc2 firefly luciferase) expression lentiviral vector (CSII-EF-ffLuc) (Takahashi Y, Tsuji O, Kumagai G, Hara C M, Okano H J, Miyawaki A, Toyama Y, Okano H, Nakamura M. Comparative study of methods for administering neural stem/progenitor cells to treat spinal cord injury in mice. Cell Transplant. 2011; 20(5):727-39.) beforehand to obtain NS/PCs with stably high expression of ffLuc.

Changes with time in NS/PCs were observed in the identical individual using the in vivo imaging system (IVIS). 200 μl of 30 mg/ml VivoGlo™ Luciferin was intraperitoneally administered under anesthesia with isoflurane inhalation, and imaging was performed using the IVIS for 10 minutes until the peak was reached (FIGS. 33A and 33B).

(C) Results

In a mouse model in which iPS-NS/PCs (ffLuc) were subcutaneously transplanted into the back, the IVIS showed accumulation of signals at the pancreatic cancer transplantation site (left side of the abdomen) 18 days later. In a mouse model in which iPS-NS/PCs were transplanted into the caudal vein, signals were trapped in the lungs on the day of administration, but began to be gradually accumulated at the pancreatic cancer transplantation site (abdomen on the left side) after day 3, and very strong accumulation was observed at day 18.

The above results showed that iPS-NS/PCs had strong anisotropic and migratory properties for pancreatic cancer as well, and that iPS-NS/PCs could be used as a favorable cellular delivery vehicles for pancreatic cancer (FIGS. 33A and 33B).

All of the publications, patents and patent applications cited herein are incorporated herein as reference as they are.

INDUSTRIAL APPLICABILITY

Since a cell preparation for treating tumors and a cell preparation for treating central nervous system diseases/damages of the present invention can be used as a pharmaceutical, the present invention can be used in industries such as manufacture of a pharmaceutical.

The invention claimed is:

1. A cell preparation for treating central nervous system diseases/damages, which comprises neural stem cells differentiated from pluripotent stem cells into which two suicide genes have been introduced, wherein the suicide genes are inserted 3' to a translation region of a β-actin gene in the pluripotent stem cell, and wherein the suicide genes are a cytosine deaminase gene and an uracil phosphoribosyltransferase gene.

2. The cell preparation for treating central nervous system diseases/damages according to claim 1, wherein a sequence coding for a 2A peptide is linked 3' to the translation region of the β-actin gene in the pluripotent stem cell, and the suicide genes are linked 3' to the sequence coding for the 2A peptide.

3. The cell preparation for treating central nervous system diseases/damages according to claim 1, wherein the neural stem cells do not comprise a selection marker gene in the genome thereof.

4. The cell preparation for treating central nervous system diseases/damages according to claim 3, wherein the neural stem cells are obtained by a method comprising the following steps (A) to (D):

(A) inserting a gene construct into the genome of pluripotent stem cells by genome editing, wherein the gene construct is a gene construct which comprises suicide genes, a selection marker gene, and two target sequences of Cre protein, and in which the selection marker gene is flanked by the two target sequences of Cre protein;

(B) selecting pluripotent stem cells in which the suicide genes have been inserted into the genome thereof from the pluripotent stem cells obtained in the step (A) using the selection marker gene;

(C) removing the selection marker gene from the genome of the pluripotent stem cells obtained in the step (B) by using Cre protein; and (D) differentiating the pluripotent stem cells obtained in the step (C) into neural stem cells.

5. The cell preparation for treating central nervous system diseases/damages according to claim 4, wherein the two target sequences of Cre protein are loxP sequences.

6. The cell preparation for treating central nervous system diseases/damages according to claim 4, wherein the two target sequences of Cre protein included in the gene construct are a mutant loxP sequence having a mutation in an upstream repetitive sequence and a mutant loxP sequence having a mutation in a downstream repetitive sequence, wherein the mutant loxP sequence having a mutation in the upstream repetitive sequence is located upstream of the selection marker gene, and the mutant loxP sequence having a mutation in the downstream repetitive sequence is located downstream of the selection marker gene in the gene construct.

7. The cell preparation for treating central nervous system diseases/damages according to claim 3, wherein the neural stem cells are obtained by a method comprising the following steps (a) to (d):

(a) inserting a gene construct into the genome of pluripotent stem cells by genome editing, wherein the gene construct is a gene construct which comprises suicide genes, a selection marker gene, a mutant loxP sequence having a mutation in a repetitive sequence, and a mutant loxP sequence having a mutation in a spacer sequence, and in which the selection marker gene is flanked by the two mutant loxP sequences;

(b) selecting pluripotent stem cells in which the suicide genes have been inserted in the genome from the pluripotent stem cells obtained in the step (a) by using the selection marker gene;

(c) removing the selection marker gene from the genome of the pluripotent stem cells obtained in the step (b) by using Cre protein and a homologous recombination vector and inserting a second gene into the genome, wherein the homologous recombination vector comprises the second gene, the mutant loxP sequence having a mutation in a repetitive sequence, and the mutant loxP sequence having a mutation in a spacer sequence, and the second gene is flanked by the two mutant loxP sequences; and (d) differentiating the pluripotent stem cells obtained in the step (c) into neural stem cells.

8. The cell preparation for treating central nervous system diseases/damages according to claim 4, wherein the genome editing uses CRISPR/Cas3.

9. The cell preparation for treating central nervous system diseases/damages according to claim 1, which is used in combination with a prodrug that is capable of being converted to 5-fluorouracil by cytosine deaminase.

10. The cell preparation for treating central nervous system diseases/damages according to claim 1, wherein the neural stem cells are neural stem cells in which the expression level of at least one selected from ephrin A receptor, ephrin A, ephrin B receptor, ephrin B, and CXC motif chemokine receptor 4 is overexpressed relative to unmodified neural stem cells.

11. The cell preparation for treating central nervous system diseases/damages according to claim 10, wherein the neural stem cells are neural stem cells in which the expression levels of ephrin A, ephrin A receptor, ephrin B receptor, ephrin B, and CXC motif chemokine receptor 4 are overexpressed relative to unmodified neural stem cells.

* * * * *

SEQUENCE LISTING

```
<160> NUMBER OF SEQ ID NOS: 49

<210> SEQ ID NO 1
<211> LENGTH: 34
```

<212> TYPE: DNA
<213> ORGANISM: Artificial Sequence
<220> FEATURE:
<223> OTHER INFORMATION: loxP

<400> SEQUENCE: 1
ataacttcgt atagcataca ttatacgaag ttat 34

<210> SEQ ID NO 2
<211> LENGTH: 34
<212> TYPE: DNA
<213> ORGANISM: Artificial Sequence
<220> FEATURE:
<223> OTHER INFORMATION: lox71

<400> SEQUENCE: 2
taccgttcgt atagcataca ttatacgaag ttat 34

<210> SEQ ID NO 3
<211> LENGTH: 34
<212> TYPE: DNA
<213> ORGANISM: Artificial Sequence
<220> FEATURE:
<223> OTHER INFORMATION: lox66

<400> SEQUENCE: 3
ataacttcgt atagcataca ttatacgaac ggta 34

<210> SEQ ID NO 4
<211> LENGTH: 34
<212> TYPE: DNA
<213> ORGANISM: Artificial Sequence
<220> FEATURE:
<223> OTHER INFORMATION: lox2272

<400> SEQUENCE: 4
ataacttcgt ataggatact ttatacgaag ttat 34

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
gacgtggagg aaaatcccg 19

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
gggtcggatc taccgttcg 19

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ccctggagaa gagctacgag 20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
cgggattttc ctccacgtca 20

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
aagtcttcta acatgcggtg ac 22

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ggtgtacaga gtggtgtcct 20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
cagccatgta cgttgctatc 20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
attttcctcc acgtcaccgc 20

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
aggaagtctt ctaacatgcg gt 22

<210> SEQ ID NO 14
<211> LENGTH: 19
<212> TYPE: DNA
<213> ORGANISM: Artificial Sequence
<220> FEATURE:
<223> OTHER INFORMATION: primer

<400> SEQUENCE: 14
ggtcggatct accgttcgt 19

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
ttctaacatg cggtgacgtg g 21

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
gtcagtctcc acaatctgct t 21

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17
gcagaggaag tcttctaaca tgc 23

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
aagggacttc ctgtaacaac g 21

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
ctggcatcgt gatggactc 19

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
acacttggcc tcatttttaa ggt 23

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
aagtactccg tgtggatcgg 20

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
gtcacacttg gcctcatttt taag 24

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
tccatcatga agtgtgacgt g 21

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
tcacacttgg cctcattttt aagg 24

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
gacgtggagg aaaatcccg 19

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
gggtcggatc cataacttcg 20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ccctggagaa gagctacgag 20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
cgggattttc ctccacgtca 20

<210> SEQ ID NO 29
<211> LENGTH: 22
<212> TYPE: DNA
<213> ORGANISM: Artificial Sequence
<220> FEATURE:
<223> OTHER INFORMATION: primer

<400> SEQUENCE: 29
aagtcttcta acatgcggtg ac 22

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
ggtgtacaga gtggtgtcct 20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
cagccatgta cgttgctatc 20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
attttcctcc acgtcaccgc 20

<210> SEQ ID NO 33
<211> LENGTH: 22
<212> TYPE: DNA
<213> ORGANISM: Artificial Sequence
<220> FEATURE:
<223> OTHER INFORMATION: primer

<400> SEQUENCE: 33
aggaagtctt ctaacatgcg gt 22

<210> SEQ ID NO 34

<211> LENGTH: 20
<212> TYPE: DNA
<213> ORGANISM: Artificial Sequence
<220> FEATURE:
<223> OTHER INFORMATION: primer

<400> SEQUENCE: 34
ggtcggatcc ataacttcgt 20

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
ttctaacatg cggtgacgtg g 21

<210> SEQ ID NO 36
<211> LENGTH: 21
<212> TYPE: DNA
<213> ORGANISM: Artificial Sequence
<220> FEATURE:
<223> OTHER INFORMATION: primer

<400> SEQUENCE: 36
gtcagtctcc acaatctgct t 21

<210> SEQ ID NO 37
<211> LENGTH: 23
<212> TYPE: DNA
<213> ORGANISM: Artificial Sequence
<220> FEATURE:
<223> OTHER INFORMATION: primer

<400> SEQUENCE: 37
gcagaggaag tcttctaaca tgc 23

<210> SEQ ID NO 38
<211> LENGTH: 21
<212> TYPE: DNA
<213> ORGANISM: Artificial Sequence
<220> FEATURE:
<223> OTHER INFORMATION: primer

<400> SEQUENCE: 38
aagggacttc ctgtaacaac g 21

<210> SEQ ID NO 39
<211> LENGTH: 19
<212> TYPE: DNA
<213> ORGANISM: Artificial Sequence
<220> FEATURE:
<223> OTHER INFORMATION: primer

<400> SEQUENCE: 39
ctggcatcgt gatggactc 19

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
acacttggcc tcatttttaa ggt 23

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
aagtactccg tgtggatcgg 20

<210> SEQ ID NO 42
<211> LENGTH: 24
<212> TYPE: DNA
<213> ORGANISM: Artificial Sequence
<220> FEATURE:
<223> OTHER INFORMATION: primer

<400> SEQUENCE: 42
gtcacacttg gcctcatttt taag 24

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
tccatcatga agtgtgacgt g 21

<210> SEQ ID NO 44
<211> LENGTH: 24
<212> TYPE: DNA
<213> ORGANISM: Artificial Sequence
<220> FEATURE:
<223> OTHER INFORMATION: primer

<400> SEQUENCE: 44
tcacacttgg cctcattttt aagg 24

<210> SEQ ID NO 45
<211> LENGTH: 99
<212> TYPE: DNA
<213> ORGANISM: Artificial Sequence
<220> FEATURE:
<223> OTHER INFORMATION: Synthetic

<400> SEQUENCE: 45
agatactact gtgtctaata ccgttcgtat agcatacatt atacgaacgg tagatccgac 60
ccctggacca cacgcgttag gcggactatg acttagttg 99

<210> SEQ ID NO 46
<211> LENGTH: 99
<212> TYPE: DNA
<213> ORGANISM: Artificial Sequence
<220> FEATURE:
<223> OTHER INFORMATION: Synthetic

<400> SEQUENCE: 46
caactaagtc atagtccgcc taacgcgtgt ggtccagggg tcggatctac cgttcgtata 60
atgtatgcta tacgaacggt attagacaca gtagtatct 99

-continued

```
<210> SEQ ID NO 47
<211> LENGTH: 101
<212> TYPE: DNA
<213> ORGANISM: Artificial Sequence
<220> FEATURE:
<223> OTHER INFORMATION: Synthetic

<400> SEQUENCE: 47

gatactactg tgtctaatac cgttcgtata gcatacatta tacgaacggt acccctctcc     60

ctccccccc cctaacgtta ctggccgaag ccgcttggaa t                         101


<210> SEQ ID NO 48
<211> LENGTH: 101
<212> TYPE: DNA
<213> ORGANISM: Artificial Sequence
<220> FEATURE:
<223> OTHER INFORMATION: Synthetic

<400> SEQUENCE: 48

attccaagcg gcttcggcca gtaacgttag ggggggggga gggagagggg taccgttcgt     60

ataatgtatg ctatacgaac ggtattagac acagtagtat c                        101


<210> SEQ ID NO 49
<211> LENGTH: 34
<212> TYPE: DNA
<213> ORGANISM: Artificial Sequence
<220> FEATURE:
<223> OTHER INFORMATION: Synthetic

<400> SEQUENCE: 49

taccgttcgt atagcataca ttatacgaac ggta                                 34
```